US008524766B2

(12) United States Patent
Sonesson et al.

(10) Patent No.: US 8,524,766 B2
(45) Date of Patent: Sep. 3, 2013

(54) MODULATORS OF DOPAMINE NEUROTRANSMISSION

(75) Inventors: Clas Sonesson, Billdal (SE); Peder Svensson, Göteborg (SE); Jonas Karlsson, Göteborg (SE)

(73) Assignee: NSAB, Filial af Neurosearch Sweden AB, Sverige, Ballerup (DK)

( * ) Notice: Subject to any disclaimer, the term of this patent is extended or adjusted under 35 U.S.C. 154(b) by 127 days.

(21) Appl. No.: 12/990,048

(22) PCT Filed: Apr. 28, 2009

(86) PCT No.: PCT/EP2009/055137
§ 371 (c)(1),
(2), (4) Date: Dec. 17, 2010

(87) PCT Pub. No.: WO2009/133107
PCT Pub. Date: Nov. 5, 2009

(65) Prior Publication Data
US 2011/0105461 A1    May 5, 2011

Related U.S. Application Data

(60) Provisional application No. 61/049,059, filed on Apr. 30, 2008.

(30) Foreign Application Priority Data

Apr. 29, 2008 (DK) .................................. 2008 00598

(51) Int. Cl.
A61K 31/357 (2006.01)
C07D 319/20 (2006.01)
(52) U.S. Cl.
USPC .......................................... 514/452; 549/362
(58) Field of Classification Search
None
See application file for complete search history.

(56) References Cited

U.S. PATENT DOCUMENTS

| | | | |
|---|---|---|---|
| 2,887,484 A | 5/1959 | Funke | |
| 2,906,757 A | 9/1959 | Mills | |
| 3,058,980 A | 10/1962 | Berg | |
| 5,126,366 A | 6/1992 | Stack et al. | |
| 5,166,367 A | 11/1992 | Stack et al. | |
| 5,189,171 A | 2/1993 | Stack et al. | |
| 5,235,055 A | 8/1993 | Stack et al. | |
| 5,245,051 A | 9/1993 | Stack et al. | |
| 5,318,988 A | 6/1994 | Schohe-Loop et al. | |
| 5,663,194 A | 9/1997 | Mewshaw | |
| 5,750,724 A | 5/1998 | Kang et al. | |
| 6,903,120 B2 | 6/2005 | Sonesson et al. | |
| 6,924,374 B2 | 8/2005 | Sonesson et al. | |
| 2004/0039023 A1 | 2/2004 | Birch et al. | |
| 2005/0250943 A1 | 11/2005 | Berger et al. | |
| 2005/0282887 A1 | 12/2005 | McComsey et al. | |
| 2006/0041008 A1 | 2/2006 | McComsey et al. | |
| 2006/0069094 A1 | 3/2006 | Bonhaus et al. | |
| 2006/0241172 A1 | 10/2006 | Zhou et al. | |
| 2007/0149542 A1 | 6/2007 | Sonesson et al. | |
| 2007/0155822 A1 | 7/2007 | Smith-Swintosky et al. | |
| 2007/0155823 A1 | 7/2007 | Smith-Swintosky et al. | |
| 2007/0155825 A1 | 7/2007 | Smith-Swintosky et al. | |
| 2007/0155826 A1 | 7/2007 | Smith-Swintosky et al. | |
| 2007/0155827 A1 | 7/2007 | Smith-Swintosky et al. | |
| 2007/0208166 A1 | 9/2007 | Baly et al. | |
| 2007/0244179 A1 | 10/2007 | Greenfield et al. | |
| 2007/0255065 A1 | 11/2007 | Yu et al. | |
| 2007/0293440 A1 | 12/2007 | Smith-Swintosky et al. | |
| 2008/0027131 A1 | 1/2008 | Smith-Swintosky et al. | |
| 2008/0234321 A1 | 9/2008 | Sonesson | |
| 2009/0209634 A1 | 8/2009 | Smith-Swintosky | |
| 2010/0216836 A1 | 8/2010 | Din Belle et al. | |
| 2011/0105462 A1 | 5/2011 | Sonesson et al. | |
| 2011/0112065 A1 | 5/2011 | Sonesson et al. | |

FOREIGN PATENT DOCUMENTS

| | | | |
|---|---|---|---|
| JP | 55-124781 | * | 9/1980 |
| WO | WO 97/17343 A1 | | 5/1997 |
| WO | WO 00/58301 A1 | | 10/2000 |
| WO | WO 01/72741 A2 | | 10/2001 |
| WO | WO 03/029238 A1 | | 4/2003 |
| WO | WO 2005/105776 A1 | | 11/2005 |
| WO | WO 2006/007435 A1 | | 1/2006 |
| WO | WO 2006/116158 A1 | | 11/2006 |
| WO | WO 2009/013390 A1 | | 1/2009 |
| WO | WO 2009/133109 A1 | | 11/2009 |
| WO | WO 2009/133110 A1 | | 11/2009 |

OTHER PUBLICATIONS

Avner et al., "1,4-Benzodioxanes as Reversible and Irreversible Antagonists at Adrenergic Receptors", Journal of Medicinal Chemistry, vol. 17, No. 2, pp. 197-200, (1974).
Database Beilstein, Accession No. 278932, Acta Polytechnica Scandinavica, Chemistry Metallurgy Series, 6, pp. 1-48, (1960). XP002541489.
Funke et al., Synthesis of 7-substituted-2-aminomethyl-1,4-bensodioxans, Gazzetta Chimica Italiana, vol. 91, pp. 1268-1281, (1961). XP002541487.
Grafe et al., "Substances synthesized on purpose for antiviral chemotherapy.1. Benzodioxzanes and 2-amino-4-phenylthiazoles", Arzneimittel-Forschung, vol. 24, No. 2, pp. 153-157, (1974).
Itazaki et al., "Synthesis of 2, 3-dihydro-1, 4-benzodioxin derivatives. I. 2-substituted-5(and 6)-sulfamoyl-2,3-dihydro-1,4-benzodioxins", Chemical & Pharmaceutical Bulletin, vol. 36, No. 9, pp. 3387-3403, (1988).
Marini-Bettolo et al., "Benzodioxans. VII. 7-Substituted-2-aminomethyl-1,4-benzodioxans", Croatica Chemica Acta, vol. 29, pp. 363-367, (1957). XP002541486.
Marini-Bettolo et al., "Benzodioxans. VII. Amino alcohols of the 1, 4-benzodioxan series", Gazzetta Chimica Italiana, vol. 87, pp. 1303-1305, (1957). XP002541488.

(Continued)

Primary Examiner — Michael Barker
(74) Attorney, Agent, or Firm — Birch, Stewart, Kolasch & Birch, LLP.

(57) ABSTRACT

The present invention relates to novel 1-(2,3-dihydro-1,4-benzodioxin-2-yl)-methanamine derivatives, useful as modulators of dopamine neurotransmission, and more specifically as dopaminergic stabilizers. In other aspects the invention relates to the use of these compounds in a method for therapy and to pharmaceutical compositions comprising the compounds of the invention.

9 Claims, No Drawings

(56) References Cited

OTHER PUBLICATIONS

Marini-Bettolo et al., DataBase Caplus, Accession No. 1958:92883, Chemical Abstracts Service, Columbus, al., "Benzodioxane series. VIII. Amino alcohols of the 1,4-benzodioxan series", (1957). XP002541490.

Mewshaw et al., "New Generation Dopaminergic Agents. Discovery of a Novel Scaffold which Embraces the D2 Agonist Pharmacophore. Structure-Activity Relationships of a Series of 2-(Aminomethyl) chromans", Journal of Medicinal Chemistry, vol. 40, No. 26, pp. 4235-4256, (1997). XP-002155829.

Timmermans et al., "Identical Antagonist Selectivity of Central and Peripheral Alpha1-Adrenoceptors", Molecular Pharmacology, vol. 20, No. 2, pp. 295-301, (1981).

Timmermans et al., Selectivity of Benzodioxane a-Adrenoceptor Determined by Binding Affinity, Pharmacology, vol. 26, No. 5, pp. 258-269, (1983).

* cited by examiner

MODULATORS OF DOPAMINE NEUROTRANSMISSION

This application is the National Phase of PCT/EP2009/055137 filed on Apr. 28, 2009, which claims the benefit under 35 U.S.C. 119(e) of U.S. Provisional Application No. 61/049,059 filed on Apr. 30, 2008, and claims priority under 35 U.S.C. 119 (a) to Patent Application No. PA 200800598 filed in Denmark on Apr. 29, 2008, all of which are hereby expressly incorporated by reference into the present application.

FIELD OF THE INVENTION

The present invention relates to novel 1-(2,3-dihydro-1,4-benzodioxin-2-yl)-methanamine derivatives, useful as modulators of dopamine neurotransmission, and more specifically as dopaminergic stabilizers.

In other aspects the invention relates to the use of these compounds in a method for therapy and to pharmaceutical compositions comprising the compounds of the invention.

BACKGROUND OF THE INVENTION

Dopamine is a neurotransmitter in the brain. Since this discovery, made in the 1950's, the function of dopamine in the brain has been intensely explored. To date, it is well established that dopamine is essential in several aspects of brain function including motor, cognitive, sensory, emotional and autonomous functions (e.g. regulation of appetite, body temperature, sleep). Thus, modulation of dopaminergic function may be beneficial in the treatment of a wide range of disorders affecting brain functions. In fact, drugs that act, directly or indirectly at central dopamine receptors are commonly used in the treatment of neurological and psychiatric disorders, e.g. Parkinson's disease and schizophrenia. However, currently available dopaminergic pharmaceuticals can have severe side effects. One class of compounds acting through the dopamine systems of the brain are dopaminergic stabilizers, which have shown to be useful in the treatment of both neurologic and psychiatric disorders.

The typical pharmacological effects which are characteristic for dopaminergic stabilizers can be summarised as: 1) Increased turnover of dopamine in the terminal areas of the ascending dopaminergic projections of the mammalian brain; 2) No or only weak behavioural effects in otherwise untreated rats; and 3) Inhibition of behavioural effects induced by psychostimulants or psychotomimetic compounds in the rat. In the present invention this is referred to as a dopaminergic stabilizer profile.

DESCRIPTION OF PRIOR ART

WO 2005/105776 discloses arylsulfonyl benzodioxanes useful as modulators of 5-HT6 and 5-HT2A receptors.

WO 2006/116158 discloses benzodioxane and benzodioxolane derivatives useful as partial agonists or agonists at 5-HT2C receptors.

Avner et al. in *Journal of Medicinal Chemistry* 1974 17 (2)197-200 disclose substituted 1,4-benzodioxanes as reversible and irreversible antagonists at adrenergic receptors.

Various chlorinated 1,4-benzodioxanes have been disclosed as ligands for α1 and α2-receptors, see e.g. *Pharmacology* 1983 26 (5) 258-69; *Molecular Pharmacology* 1981 20 (2) 295-301; *Croatica Chemica Acta* 1957 29 363-367; and *Gazzetta Chimica Italiana* 1957 87 1303-1305.

The compound 3-morpholin-4-ylmethyl-2,3-dihydro-benzo[1,4]dioxine-6-carbonitrile is disclosed as a synthesis intermediate by Funke et al.: Synthesis of 7-substituted-2-aminomethyl-1,4-benazodioxanes; *Gazzetta Chimica Italiana* 1961 91 1268-1281.

Finally U.S. Pat. No. 5,126,366 describes certain aminophenoxyalkyl derivatives of benzodioxan; U.S. Pat. No. 5,166,367 and U.S. Pat. No. 5,189,171 describe certain antipsychotic benzodioxan derivatives; U.S. Pat. No. 5,235,055 describes certain antipsychotic quinoline derivatives of benzodioxanmethylamine; U.S. Pat. No. 5,245,051 describes certain antipsychotic chroman derivatives of benzodioxanmethylamine; and U.S. Pat. No. 5,318,988 describes certain 2-aminomethyl-chromans.

However, the 1-(2,3-dihydro-1,4-benzodioxin-2-yl) methanamine derivatives of the present invention and their use as dopaminergic stabilizers have never been reported.

SUMMARY OF THE INVENTION

The object of the present invention is to provide novel pharmaceutically active compounds, especially useful in treatment of disorders in the central nervous system. A further object is the provision of compounds for modulation of dopaminergic systems in the mammalian brain, including human brain. A still further object is the provision of novel compounds with a dopaminergic stabilizer profile. A further object is to provide compounds with therapeutic effects after oral administration. A still further object is the provision of compounds with more optimal pharmacodynamic properties such as e.g. kinetic behaviour, bioavailability, solubility and efficacy. A further object is to provide compounds being superior to presently known dopaminergic compounds in the treatment of several disorders related to dysfunctions of the CNS, in terms of efficacy or side effects.

The present invention concerns the unexpected discovery of the pharmacological effects of compounds of Formula 1 on the dopaminergic system in the brain. By pharmacological testing in vivo in the rat it is demonstrated that compounds of the present invention have effects on biochemical indices in the brain with the characteristic features of dopamine antagonists.

In its first aspect, the invention provides a compound of Formula 1

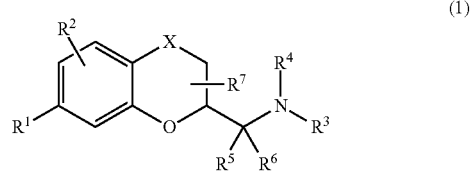

(1)

any of its stereoisomers or any mixture of its stereoisomers, or an N-oxide thereof, or a pharmaceutically acceptable salt thereof; wherein $R^1$, $R^2$, $R^3$, $R^4$, $R^5$, $R^6$, $R^7$ and X are as defined below.

In its second aspect, the invention provides a pharmaceutical composition, comprising a therapeutically effective amount of a compound of the invention, any of its stereoisomers or any mixture of its stereoisomers, or an N-oxide thereof, or a pharmaceutically acceptable salt thereof, together with at least one pharmaceutically acceptable carrier, excipient or diluent.

In a further aspect, the invention provides the use of a compound of the invention, any of its stereoisomers or any mixture of its stereoisomers or an N-oxide thereof, or a pharmaceutically acceptable salt thereof, for the manufacture of a pharmaceutical composition for the treatment, prevention or alleviation of a disease or a disorder or a condition of a mammal, including a human, which disease, disorder or condition is responsive to responsive to modulation of dopaminergic function in the central nervous system.

In a still further aspect, the invention relates to a method for treatment, prevention or alleviation of a disease or a disorder or a condition of a living animal body, including a human, which disorder, disease or condition is responsive to modulation of dopaminergic function in the central nervous system, which method comprises the step of administering to such a living animal body in need thereof a therapeutically effective amount of a compound of the invention, any of its stereoisomers or any mixture of its stereoisomers, or an N-oxide thereof, or a pharmaceutically acceptable salt thereof.

Other aspects of the invention will be apparent to the person skilled in the art from the following detailed description and examples.

DETAILED DESCRIPTION OF THE INVENTION

1-(2,3-Dihydro-1,4-benzodioxin-2-yl)methanamine Derivatives

In its first aspect the present invention provides compounds of Formula 1:

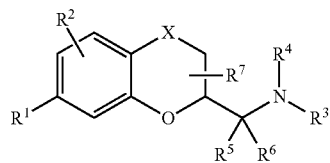

(1)

any of its stereoisomers or any mixture of its stereoisomers, or an N-oxide thereof, or a pharmaceutically acceptable salt thereof; wherein:

X is O, S, NH or $CH_2$;

$R^1$ is selected from the group consisting of $SOR^8$, $SO_2R^8$, $SO_2NH_2$, $SO_2NHCH_3$ and $SO_2N(CH_3)$;

$R^2$ is selected from the group consisting of H, ON, F, Cl, Br, I and $CH_3$;

$R^3$ is selected from the group consisting of $C_1$-$C_5$ alkyl, allyl, $CH_2CH_2OCH_3$, $CH_2CH_2CH_2F$, $CH_2CH_2CHF_2$, $CH_2CH_2F$, 3,3,3-trifluoropropyl, 4,4,4-trifluorobutyl, $CH_2CH_2OH$, $CH_2CH_2CH_2OH$, $CH_2CH(OH)CH_3$, $CH_2CH_2COCH_3$, $C_3$-$C_6$ cycloalkyl,

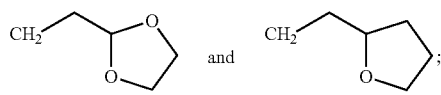

$R^4$ is selected from the group consisting of H, $C_1$-$C_5$ alkyl, allyl, $CH_2CH_2OCH_3$, $CH_2CH_2CH_2F$, $CH_2CH_2CHF_2$, $CH_2CH_2F$, 3,3,3-trifluoropropyl, 4,4,4-trifluorobutyl, $CH_2CH_2OH$, $CH_2CH_2CH_2OH$, $CH_2CH(OH)CH_3$, $CH_2CH_2COCH_3$,

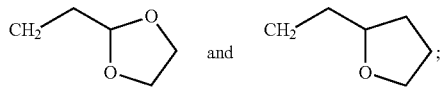

or $R^3$ and $R^4$ together with the nitrogen atom to which they are attached form a four- to six-membered heterocyclic ring, which heterocyclic ring may optionally comprise as a ring member, one oxygen atom, and/or one additional nitrogen atom; and which heterocyclic ring may optionally be substituted with $C_1$-$C_5$ alkyl;

$R^5$, $R^6$ and $R^7$ are selected from the group consisting of H and $CH_3$;

$R_8$ is selected from the group consisting of $C_1$-$C_3$ alkyls, $CF_3$, $CHF_2$, $CH_2F$ and CN.

In a more preferred embodiment the compound of the invention is a compound of Formula 1A,

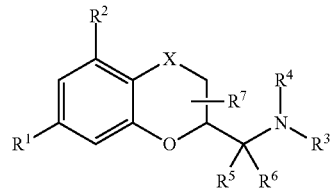

(1A)

any of its stereoisomers or any mixture of its stereoisomers, or an N-oxide thereof, or a pharmaceutically acceptable salt thereof; wherein X, $R^1$, $R^2$, $R^3$, $R^4$, $R^5$, $R^6$ and $R^7$ are as defined above.

In a more preferred embodiment the compound of the invention is a compound of Formula 1B

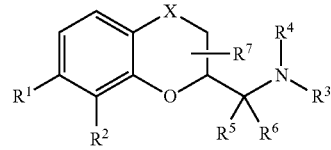

(1B)

any of its stereoisomers or any mixture of its stereoisomers, or an N-oxide thereof, or a pharmaceutically acceptable salt thereof; wherein X, $R^1$, $R^2$, $R^3$, $R^4$, $R^5$, $R^6$ and $R^7$ are as defined above.

In a preferred embodiment the compound of the invention is a compound of Formula 1, 1A or 1B, any of its stereoisomers or any mixture of its stereoisomers, or an N-oxide thereof, or a pharmaceutically acceptable salt thereof, wherein X is O, S, NH or $CH_2$.

In a more preferred embodiment X is O.

In another more preferred embodiment X is S.

In a third more preferred embodiment X is NH.

In a fourth more preferred embodiment X is $CH_2$.

In another preferred embodiment the compound of the invention is a compound of Formula 1, 1A or 1B, any of its stereoisomers or any mixture of its stereoisomers, or an N-oxide thereof, or a pharmaceutically acceptable salt thereof, wherein $R^1$ is selected from the group consisting of $SOR^8$, $SO_2R^8$, $SO_2NH_2$, $SO_2NHCH_3$ and $SO_2N(CH_3)$; and $R^8$ is selected from the group consisting of $C_1$-$C_3$ alkyl, $CF_3$, $CHF_2$, $CH_2F$ and CN.

In a more preferred embodiment $R^1$ is $SOR^8$; and $R^8$ is selected from the group consisting of $C_1$-$C_3$ alkyl, $CF_3$, $CHF_2$, $CH_2F$ and CN.

In another more preferred embodiment $R^1$ is $SO_2R^8$; and $R^8$ is selected from the group consisting of $C_1$-$C_3$ alkyl, $CF_3$, $CHF_2$, $CH_2F$ and CN.

In a third more preferred embodiment $R^1$ is $SO_2R^8$; and $R^8$ is selected from the group consisting of $C_1$-$C_3$ alkyl and $CF_3$.

In a fourth more preferred embodiment $R^1$ is $SO_2NH_2$.
In a fifth more preferred embodiment $R^1$ is $SO_2NHCH_3$.
In a sixth more preferred embodiment $R^1$ is $SO_2N(CH_3)$.
In a seventh more preferred embodiment $R^1$ is selected from the group consisting of $SO_2CH_3$ and $SO_2CF_3$.

In a third preferred embodiment the compound of the invention is a compound of Formula 1, 1A or 1B, any of its stereoisomers or any mixture of its stereoisomers, or an N-oxide thereof, or a pharmaceutically acceptable salt thereof, wherein $R^2$ is selected from the group consisting of H, CN, F, Cl, Br, I and $CH_3$.

In a more preferred embodiment $R^2$ is H.
In another more preferred embodiment $R^2$ is CN.
In a third more preferred embodiment $R^2$ is F.
In a fourth more preferred embodiment $R^2$ is Cl.
In a fifth more preferred embodiment $R^2$ is Br.
In a sixth more preferred embodiment $R^2$ is I.
In a seventh more preferred embodiment $R^2$ is $CH_3$.
In an eight more preferred embodiment $R^2$ is selected from the group consisting of H, F and Cl.

In a fourth preferred embodiment the compound of the invention is a compound of Formula 1, 1A or 1B, any of its stereoisomers or any mixture of its stereoisomers, or an N-oxide thereof, or a pharmaceutically acceptable salt thereof, wherein $R^3$ is selected from the group consisting of $C_1$-$C_5$ alkyl, allyl, $CH_2CH_2OCH_3$, $CH_2CH_2CH_2F$, $CH_2CH_2CHF_2$, $CH_2CH_2F$, 3,3,3-trifluoropropyl, 4,4,4-trifluorobutyl, $CH_2CH_2OH$, $CH_2CH_2CH_2OH$, $CH_2CH(OH)CH_3$, $CH_2CH_2COCH_3$, $C_3$-$C_6$ cycloalkyl,

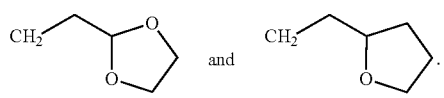

In a more preferred embodiment $R^3$ is $C_1$-$C_5$ alkyl.
In another more preferred embodiment $R^3$ is allyl.
In a third more preferred embodiment $R^3$ is $CH_2CH_2OCH_3$.
In a fourth more preferred embodiment $R^3$ is $CH_2CH_2CH_2F$.
In a fifth more preferred embodiment $R^3$ is $CH_2CH_2CHF_2$.
In a sixth more preferred embodiment $R^3$ is $CH_2CH_2F$.
In a seventh more preferred embodiment $R^3$ is 3,3,3-trifluoropropyl.
In an eight more preferred embodiment $R^3$ is 4,4,4-trifluorobutyl.
In a ninth more preferred embodiment $R^3$ is $CH_2CH_2OH$.
In a tenth more preferred embodiment $R^3$ is $CH_2CH_2CH_2OH$.
In an eleventh more preferred embodiment $R^3$ is $CH_2CH(OH)CH_3$.
In a twelfth more preferred embodiment $R^3$ is $CH_2CH_2COCH_3$.
In a thirteenth more preferred embodiment $R^3$ is $C_3$-$C_6$ cycloalkyl.

In a fourteenth more preferred embodiment $R^3$ is

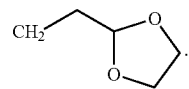

In a fifteenth more preferred embodiment $R^3$ is

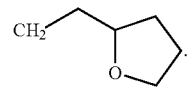

In a sixteenth more preferred embodiment $R^3$ is selected from the group consisting of $C_1$-$C_5$ alkyl, allyl, 3,3,3-trifluoropropyl, $CH_2CH_2OCH_3$ and $CH_2CH_2OH$.

In a fifth preferred embodiment the compound of the invention is a compound of Formula 1, 1A or 1B, any of its stereoisomers or any mixture of its stereoisomers, or an N-oxide thereof, or a pharmaceutically acceptable salt thereof, wherein $R^4$ is selected from the group consisting of H, $C_1$-$C_5$ alkyl, allyl, $CH_2CH_2OCH_3$, $CH_2CH_2CH_2F$, $CH_2CH_2CHF_2$, $CH_2CH_2F$, 3,3,3-trifluoropropyl, 4,4,4-trifluorobutyl, $CH_2CH_2OH$, $CH_2CH_2CH_2OH$, $CH_2CH(OH)CH_3$, $CH_2CH_2COCH_3$,

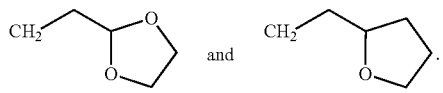

In a more preferred embodiment $R^4$ is H.
In another more preferred embodiment $R^4$ is $C_1$-$C_5$ alkyl.
In a third more preferred embodiment $R^4$ is allyl.
In a fourth more preferred embodiment $R^4$ is $CH_2CH_2OCH_3$.
In a fifth more preferred embodiment $R^4$ is $CH_2CH_2CH_2F$.
In a sixth more preferred embodiment $R^4$ is $CH_2CH_2CHF_2$.
In a seventh more preferred embodiment $R^4$ is $CH_2CH_2F$.
In an eight more preferred embodiment $R^4$ is 3,3,3-trifluoropropyl.
In a ninth more preferred embodiment $R^4$ is 4,4,4-trifluorobutyl.
In a tenth more preferred embodiment $R^4$ is $CH_2CH_2OH$.
In an eleventh more preferred embodiment $R^4$ is $CH_2CH_2CH_2OH$.
In a twelfth more preferred embodiment $R^4$ is $CH_2CH(OH)CH_3$.
In a thirteenth more preferred embodiment $R^4$ is $CH_2CH_2COCH_2$.

In a fourteenth more preferred embodiment $R^4$ is

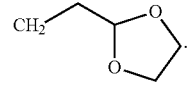

In a fifteenth more preferred embodiment $R^4$ is

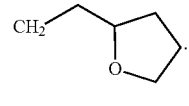

In a sixteenth more preferred embodiment $R^4$ is selected from the group consisting of H and $C_1$-$C_5$ alkyl.

In a sixth preferred embodiment the compound of the invention is a compound of Formula 1, 1A or 1B, any of its stereoisomers or any mixture of its stereoisomers, or an N-oxide thereof, or a pharmaceutically acceptable salt thereof, wherein $R^3$ and $R^4$ together with the nitrogen atom to which they are attached form a four- to six-membered heterocyclic ring, which heterocyclic ring may optionally comprise as a ring member, one oxygen atom, and/or one additional nitrogen atom; and which heterocyclic ring may optionally be substituted with $C_1$-$C_5$ alkyl.

In a more preferred embodiment $R^3$ and $R^4$ together with the nitrogen atom to which they are attached form a four-membered heterocyclic ring, which heterocyclic ring may optionally be substituted with $C_1$-$C_5$ alkyl.

In another more preferred embodiment $R^3$ and $R^4$ together with the nitrogen atom to which they are attached form a five-membered heterocyclic ring, which heterocyclic ring may optionally be substituted with $C_1$-$C_5$ alkyl.

In a third more preferred embodiment $R^3$ and $R^4$ together with the nitrogen atom to which they are attached form a six-membered heterocyclic ring, which heterocyclic ring may optionally comprise as a ring member one oxygen atom and/or one additional nitrogen atom; and which heterocyclic ring may optionally be substituted with $C_1$-$C_5$ alkyl.

In a fourth more preferred embodiment $R^3$ and $R^4$ together with the nitrogen atom to which they are attached form a six-membered heterocyclic ring, which heterocyclic ring may optionally comprise as a ring member one oxygen atom, and which heterocyclic ring may optionally be substituted with $C_1$-$C_5$ alkyl.

In a fifth more preferred embodiment $R^3$ and $R^4$ together with the nitrogen atom to which they are attached form a six-membered heterocyclic ring, which heterocyclic ring may optionally be substituted with $C_1$-$C_5$ alkyl.

In a sixth more preferred embodiment $R^3$ and $R^4$ together with the nitrogen atom to which they are attached form a six-membered heterocyclic ring, which heterocyclic ring may optionally comprise as a ring member one oxygen atom.

In a seventh more preferred embodiment $R^3$ and $R^4$ together the nitrogen atom to which they are attached form acetidine, pyrrolidine, piperidine, $C_1$-$C_5$ alkyl-piperidine or morpholine.

In an eight more preferred embodiment $R^3$ and $R^4$ together the nitrogen atom to which they are attached form an acetidine group.

In a ninth more preferred embodiment $R^3$ and $R^4$ together the nitrogen atom to which they are attached form a pyrrolidine group.

In a tenth more preferred embodiment $R^3$ and $R^4$ together the nitrogen atom to which they are attached form a piperidine group.

In an eleventh more preferred embodiment $R^3$ and $R^4$ together the nitrogen atom to which they are attached form a $C_1$-$C_5$ alkyl-piperidine group.

In a twelfth more preferred embodiment $R^3$ and $R^4$ together the nitrogen atom to which they are attached form a morpholine group.

In a seventh preferred embodiment the compound of the invention is a compound of Formula 1, 1A or 1B, any of its stereoisomers or any mixture of its stereoisomers, or an N-oxide thereof, or a pharmaceutically acceptable salt thereof, wherein $R^5$, $R^6$ and $R^7$ are selected from the group consisting of H and $CH_3$.

In a more preferred embodiment each of $R^5$, $R^6$ and $R^7$ is H.

In an eight preferred embodiment the compound of the invention is a compound of Formula 1, 1A or 1B, any of its stereoisomers or any mixture of its stereoisomers, or an N-oxide thereof, or a pharmaceutically acceptable salt thereof, wherein X represents O or $CH_2$;
$R^1$ represents $SO_2R^8$;
$R^2$ represents H, F or Cl;
$R^3$ represents $C_1$-$C_5$ alkyl, allyl, $CH_2CH_2OCH_3$, 3,3,3-trifluoropropyl or $CH_2CH_2OH$; and
$R^4$ represents H or $C_1$-$C_5$ alkyl; or
$R^3$ and $R^4$ together the nitrogen atom to which they are attached form an acetidine, a pyrrolidine, a piperidine, a $C_1$-$C_5$ alkyl-piperidine or a morpholine group;
$R^5$, $R^6$ and $R^7$ all represent H; and
$R^8$ represents $C_1$-$C_3$ alkyl or $CF_3$.

In a further more preferred embodiment the compound of the invention is

N-{[7-(METHYLSULFONYL)-2,3-DIHYDRO-1,4-BENZODIOXIN-2-YL]METHYL}-PROPAN-1-AMINE;
N-{[(2R)-7-(METHYLSULFONYL)-2,3-DIHYDRO-1,4-BENZODIOXIN-2-YL]METHYL}-PROPAN-1-AMINE;
N-{[(2S)-7-(METHYLSULFONYL)-2,3-DIHYDRO-1,4-BENZODIOXIN-2-YL]METHYL}-PROPAN-1-AMINE;
N-{[7-(METHYLSULFONYL)-2,3-DIHYDRO-1,4-BENZODIOXIN-2-YL]METHYL}ETHANAMINE;
N-{[(2S)-7-(METHYLSULFONYL)-2,3-DIHYDRO-1,4-BENZODIOXIN-2-YL]METHYL}ETHANAMINE;
1-{[7-(METHYLSULFONYL)-2,3-DIHYDRO-1,4-BENZODIOXIN-2-YL]METHYL}PIPERIDINE;
1-{[(2S)-7-(METHYLSULFONYL)-2,3-DIHYDRO-1,4-BENZODIOXIN-2-YL]METHYL}PIPERIDINE;
1-{[(2R)-7-(METHYLSULFONYL)-2,3-DIHYDRO-1,4-BENZODIOXIN-2-YL]METHYL}PIPERIDINE;
N-METHYL-1-[7-(METHYLSULFONYL)-2,3-DIHYDRO-1,4-BENZODIOXIN-2-YL]METHANAMINE;
N-METHYL-1-[(2S)-7-(METHYLSULFONYL)-2,3-DIHYDRO-1,4-BENZODIOXIN-2-YL]METHANAMINE;
1-{[7-(METHYLSULFONYL)-2,3-DIHYDRO-1,4-BENZODIOXIN-2-YL]METHYL}PYRROLIDINE;
3-METHYL-1-{[(2R)-7-(METHYLSULFONYL)-2,3-DIHYDRO-1,4-BENZODIOXIN-2-YL]METHYL}PIPERIDINE;
2-METHYL-N-{[(2R)-7-(METHYLSULFONYL)-2,3-DIHYDRO-1,4-BENZODIOXIN-2-YL]METHYL}PROPAN-1-AMINE;
2-METHYL-N-{[(2S)-7-(METHYLSULFONYL)-2,3-DIHYDRO-1,4-BENZODIOXIN-2-YL]METHYL}PROPAN-1-AMINE;
N-METHYL-N-{[7-(METHYLSULFONYL)-2,3-DIHYDRO-1,4-BENZODIOXIN-2-YL]METHYL}PROPAN-1-AMINE;
N-{[7-(METHYLSULFONYL)-2,3-DIHYDRO-1,4-BENZODIOXIN-2-YL]METHYL}-N-PROPYLPROPAN-1-AMINE;
N-{[5-FLUORO-7-(METHYLSULFONYL)-2,3-DIHYDRO-1,4-BENZODIOXIN-2-YL]METHYL}-N-PROPAN-1-AMINE;
N-{[5-FLUORO-7-(METHYLSULFONYL)-2,3-DIHYDRO-1,4-BENZODIOXIN-2-YL]METHYL}ETHANAMINE;
N-{[(2S)-5-FLUORO-7-(METHYLSULFONYL)-2,3-DIHYDRO-1,4-BENZODIOXIN-2-YL]METHYL}ETHANAMINE;

1-[5-FLUORO-7-(METHYLSULFONYL)-2,3-DIHYDRO-1,4-BENZODIOXIN-2-YL]-N-METHYLMETHANAMINE;
N-{[(2S)-5-FLUORO-7-(METHYLSULFONYL)-2,3-DIHYDRO-1,4-BENZODIOXIN-2-YL]METHYL}PROPAN-1-AMINE;
N-{[(2S)-7-(TRIFLUOROMETHYLSULFONYL)-2,3-DIHYDRO-1,4-BENZODIOXIN-2-YL]METHYL}ETHANAMINE;
N-{[7-(METHYLSULFONYL)-3,4-DIHYDRO-2H-CHROMEN-2-YL]METHYL}-N-PROPAN-1-AMINE;
N-{[(2S)-7-(TRIFLUOROMETHYLSULFONYL)-2,3-DIHYDRO-1,4-BENZODIOXIN-2-YL]METHYL}PROPAN-1-AMINE;
N-{[7-(METHYLSULFONYL)-2,3-DIHYDRO-1,4-BENZODIOXIN-2-YL]METHYL}PROP-2-EN-1-AMINE;
4-{[7-(METHYLSULFONYL)-2,3-DIHYDRO-1,4-BENZODIOXIN-2-YL]METHYL}MORPHOLINE;
N-{[7-(METHYLSULFONYL)-2,3-DIHYDRO-1,4-BENZODIOXIN-2-YL]METHYL}BUTAN-1-AMINE;
N,N-DIMETHYL-N-{[7-(METHYLSULFONYL)-2,3-DIHYDRO-1,4-BENZODIOXIN-2-YL]METHANAMINE;
N-ETHYL-N-{[7-(METHYLSULFONYL)-2,3-DIHYDRO-1,4-BENZODIOXIN-2-YL]METHYL}ETHANAMINE;
N-{[7-(METHYLSULFONYL)-2,3-DIHYDRO-1,4-BENZODIOXIN-2-YL]METHYL}PROPAN-2-AMINE;
N-ETHYL-N-{[7-(METHYLSULFONYL)-2,3-DIHYDRO-1,4-BENZODIOXIN-2-YL]METHYL}-N-PROPAN-1-AMINE;
2-({[7-(METHYLSULFONYL)-2,3-DIHYDRO-1,4-BENZODIOXIN-2-YL]METHYL}AMINO)ETHANOL;
N-METHYL-N-{[7-(METHYLSULFONYL)-2,3-DIHYDRO-1,4-BENZODIOXIN-2-YL]METHYL}ETHANAMINE;
2-METHOXY-N-{[7-(METHYLSULFONYL)-2,3-DIHYDRO-1,4-BENZODIOXIN-2-YL]METHYL}ETHANAMINE;
1-{[7-(METHYLSULFONYL)-2,3-DIHYDRO-1,4-BENZODIOXIN-2-YL]METHYL}AZETIDINE;
2-METHYL-N-{[7-(METHYLSULFONYL)-2,3-DIHYDRO-1,4-BENZODIOXIN-2-YL]METHYL}PROPAN-1-AMINE;
N-{[(2S)-8-FLUORO-7-(METHYLSULFONYL)-2,3-DIHYDRO-1,4-BENZODIOXIN-2-YL]METHYL}ETHANAMINE;
N-{[(2S)-5-CHLORO-7-(METHYLSULFONYL)-2,3-DIHYDRO-1,4-BENZODIOXIN-2-YL]METHYL}ETHANAMINE;
N-{[(2S)-7-(METHYLSULFONYL)-2,3-DIHYDRO-1,4-BENZODIOXIN-2-YL]METHYL}-N-(3,3,3-TRIFLUOROPROPYL)AMINE;
N-{[(2S)-5-FLUORO-7-(METHYLSULFONYL)-2,3-DIHYDRO-1,4-BENZODIOXIN-2-YL]METHYL}-N-(3,3,3-TRIFLUOROPROPYL)AMINE;
1-[(2S)-5-FLUORO-7-(METHYLSULFONYL)-2,3-DIHYDRO-1,4-BENZODIOXIN-2-YL]-N-METHYLMETHANAMINE;
N-{[5-FLUORO-7-(METHYLSULFONYL)-2,3-DIHYDRO-1,4-BENZODIOXIN-2-YL]METHYL}PROP-2-EN-1-AMINE;
4-{[5-FLUORO-7-(METHYLSULFONYL)-2,3-DIHYDRO-1,4-BENZODIOXIN-2-YL]METHYL}MORPHOLINE;
N-{[5-FLUORO-7-(METHYLSULFONYL)-2,3-DIHYDRO-1,4-BENZODIOXIN-2-YL]METHYL}BUTAN-1-AMINE;
N-{[5-FLUORO-7-(METHYLSULFONYL)-2,3-DIHYDRO-1,4-BENZODIOXIN-2-YL]METHYL}-N-PROPYLPROPAN-1-AMINE;
1-[5-FLUORO-7-(METHYLSULFONYL)-2,3-DIHYDRO-1,4-BENZODIOXIN-2-YL]-N,N-DIMETHYLMETHANAMINE;
N-ETHYL-N-{[5-FLUORO-7-(METHYLSULFONYL)-2,3-DIHYDRO-1,4-BENZODIOXIN-2-YL]METHYL}ETHANAMINE;
N-{[5-FLUORO-7-(METHYLSULFONYL)-2,3-DIHYDRO-1,4-BENZODIOXIN-2-YL]METHYL}PROPAN-2-AMINE;
N-{[5-FLUORO-7-(METHYLSULFONYL)-2,3-DIHYDRO-1,4-BENZODIOXIN-2-YL]METHYL}-N-METHYLPROPAN-1-AMINE;
N-ETHYL-N-{[5-FLUORO-7-(METHYLSULFONYL)-2,3-DIHYDRO-1,4-BENZODIOXIN-2-YL]METHYL}PROPAN-1-AMINE;
2-({[5-FLUORO-7-(METHYLSULFONYL)-2,3-DIHYDRO-1,4-BENZODIOXIN-2-YL]METHYL}AMINO)ETHANOL;
N-{[5-FLUORO-7-(METHYLSULFONYL)-2,3-DIHYDRO-1,4-BENZODIOXIN-2-YL]METHYL}-N-METHYLETHANAMINE;
N-{[5-FLUORO-7-(METHYLSULFONYL)-2,3-DIHYDRO-1,4-BENZODIOXIN-2-YL]METHYL}-2-METHOXYETHANAMINE;
1-{[5-FLUORO-7-(METHYLSULFONYL)-2,3-DIHYDRO-1,4-BENZODIOXIN-2-YL]METHYL}AZETIDINE;
N-{[5-FLUORO-7-(METHYLSULFONYL)-2,3-DIHYDRO-1,4-BENZODIOXIN-2-YL]METHYL}-2-METHYLPROPAN-1-AMINE;
1-{[5-FLUORO-7-(METHYLSULFONYL)-2,3-DIHYDRO-1,4-BENZODIOXIN-2-YL]METHYL}PYRROLIDINE;
N-{[(2S)-5-CHLORO-7-(METHYLSULFONYL)-2,3-DIHYDRO-1,4-BENZODIOXIN-2-YL]METHYL}PROP-2-EN-1-AMINE;
N-{[(2S)-5-CHLORO-7-(METHYLSULFONYL)-2,3-DIHYDRO-1,4-BENZODIOXIN-2-YL]METHYL}BUTAN-1-AMINE;
N-{[(2S)-5-CHLORO-7-(METHYLSULFONYL)-2,3-DIHYDRO-1,4-BENZODIOXIN-2-YL]METHYL}-N-PROPYLPROPAN-1-AMINE;
1-[(2S)-5-CHLORO-7-(METHYLSULFONYL)-2,3-DIHYDRO-1,4-BENZODIOXIN-2-YL]-N,N-DIMETHYLMETHANAMINE;
N-ETHYL-N-{[(2S)-5-CHLORO-7-(METHYLSULFONYL)-2,3-DIHYDRO-1,4-BENZODIOXIN-2-YL]METHYL}ETHANAMINE;
N-{[(2S)-5-CHLORO-7-(METHYLSULFONYL)-2,3-DIHYDRO-1,4-BENZODIOXIN-2-YL]METHYL}PROPAN-2-AMINE;
N-{[(2S)-5-CHLORO-7-(METHYLSULFONYL)-2,3-DIHYDRO-1,4-BENZODIOXIN-2-YL]METHYL}-N-METHYLPROPAN-1-AMINE;
N-ETHYL-N-{[(2S)-5-CHLORO-7-(METHYLSULFONYL)-2,3-DIHYDRO-1,4-BENZODIOXIN-2-YL]METHYL}PROPAN-1-AMINE;
2-({[(2S)-5-CHLORO-7-(METHYLSULFONYL)-2,3-DIHYDRO-1,4-BENZODIOXIN-2-YL]METHYL}AMINO)ETHANOL;
N-{[(2S)-5-CHLORO-7-(METHYLSULFONYL)-2,3-DIHYDRO-1,4-BENZODIOXIN-2-YL]METHYL}-N-METHYLETHANAMINE;

N-{[(2S)-5-CHLORO-7-(METHYLSULFONYL)-2,3-DIHYDRO-1,4-BENZODIOXIN-2-YL]METHYL}-2-METHOXYETHANAMINE;
1-{[(2S)-5-CHLORO-7-(METHYLSULFONYL)-2,3-DIHYDRO-1,4-BENZODIOXIN-2-YL]METHYL}AZETIDINE;
N-{[(2S)-5-CHLORO-7-(METHYLSULFONYL)-2,3-DIHYDRO-1,4-BENZODIOXIN-2-YL]METHYL}-2-METHYLPROPAN-1-AMINE;
1-{[(2S)-5-CHLORO-7-(METHYLSULFONYL)-2,3-DIHYDRO-1,4-BENZODIOXIN-2-YL]METHYL}PYRROLIDINE;
N-{[(2S)-5-CHLORO-7-(METHYLSULFONYL)-2,3-DIHYDRO-1,4-BENZODIOXIN-2-YL]METHYL}-PROPAN-1-AMINE;
N-{[(2S)-5-CHLORO-7-(METHYLSULFONYL)-2,3-DIHYDRO-1,4-BENZODIOXIN-2-YL]METHYL}-3-FLUOROPROPAN-1-AMINE;
N-{[(2S)-5-CHLORO-7-(METHYLSULFONYL)-2,3-DIHYDRO-1,4-BENZODIOXIN-2-YL]METHYL}-2,2-DIMETHYLPROPAN-1-AMINE;
1-{[(2S)-5-CHLORO-7-(METHYLSULFONYL)-2,3-DIHYDRO-1,4-BENZODIOXIN-2-YL]METHYL}PIPERIDINE;
1-[(2S)-5-CHLORO-7-(METHYLSULFONYL)-2,3-DIHYDRO-1,4-BENZODIOXIN-2-YL]-N-METHYL-METHANAMINE;
N-{[(2S)-5-FLUORO-7-(METHYLSULFONYL)-2,3-DIHYDRO-1,4-BENZODIOXIN-2-YL]METHYL}-PROPAN-1-AMINE;
2,2-DIMETHYL-N-{[(2S)-7-(METHYLSULFONYL)-2,3-DIHYDRO-1,4-BENZODIOXIN-2-YL]METHYL}PROPAN-1-AMINE;
N-METHYL-1-[7-(METHYLSULFONYL)-3,4-DIHYDRO-2H-CHROMEN-2-YL]METHANAMINE;
N-{[7-(METHYLSULFONYL)-3,4-DIHYDRO-2H-CHROMEN-2-YL]METHYL}ETHANAMINE;
N-{[7-(METHYLSULFONYL)-3,4-DIHYDRO-2H-CHROMEN-2-YL]METHYL}PROP-2-EN-1-AMINE;
4-{[7-(METHYLSULFONYL)-3,4-DIHYDRO-2H-CHROMEN-2-YL]METHYL}MORPHOLINE;
N-{[7-(METHYLSULFONYL)-3,4-DIHYDRO-2H-CHROMEN-2-YL]METHYL}BUTAN-1-AMINE;
N-{[7-(METHYLSULFONYL)-3,4-DIHYDRO-2H-CHROMEN-2-YL]METHYL}-N-PROPYLPROPAN-1-AMINE;
N,N-DIMETHYL-1-[7-(METHYLSULFONYL)-3,4-DIHYDRO-2H-CHROMEN-2-YL]METHANAMINE;
N-ETHYL-N-{[7-(METHYLSULFONYL)-3,4-DIHYDRO-2H-CHROMEN-2-YL]METHYL}ETHANAMINE;
N-{[7-(METHYLSULFONYL)-3,4-DIHYDRO-2H-CHROMEN-2-YL]METHYL}PROPAN-2-AMINE;
N-METHYL-N-{[7-(METHYLSULFONYL)-3,4-DIHYDRO-2H-CHROMEN-2-YL]METHYL}PROPAN-1-AMINE;
N-ETHYL-N-{[7-(METHYLSULFONYL)-3,4-DIHYDRO-2H-CHROMEN-2-YL]METHYL}PROPAN-1-AMINE;
2-({[7-(METHYLSULFONYL)-3,4-DIHYDRO-2H-CHROMEN-2-YL]METHYL}AMINO)ETHANOL;
N-METHYL-N-{[7-(METHYLSULFONYL)-3,4-DIHYDRO-2H-CHROMEN-2-YL]METHYL}ETHANAMINE;
2-METHOXY-N-{[7-(METHYLSULFONYL)-3,4-DIHYDRO-2H-CHROMEN-2-YL]METHYL}ETHANAMINE;
1-{[7-(METHYLSULFONYL)-3,4-DIHYDRO-2H-CHROMEN-2-YL]METHYL}AZETIDINE;
2-METHYL-N-{[7-(METHYLSULFONYL)-3,4-DIHYDRO-2H-CHROMEN-2-YL]METHYL}PROPAN-1-AMINE;
1-{[7-(METHYLSULFONYL)-3,4-DIHYDRO-2H-CHROMEN-2-YL]METHYL}PYRROLIDINE;
1-{[7-(METHYLSULFONYL)-3,4-DIHYDRO-2H-CHROMEN-2-YL]METHYL}PIPERIDINE;
3-FLUORO-N-{[7-(METHYLSULFONYL)-3,4-DIHYDRO-2H-CHROMEN-2-YL]METHYL}PROPAN-1-AMINE;
4-{[(S)-5-FLUORO-7-(METHYLSULFONYL)-2,3-DIHYDRO-1,4-BENZODIOXIN-2-YL]METHYL}MORPHOLINE; or
N-({(2S)-7-[(TRIFLUOROMETHYL)SULFONYL]-2,3-DIHYDRO-1,4-BENZODIOXIN-2-YL}METHYL)PROPAN-2-AMINE;
any of its stereoisomers or any mixture of its stereoisomers, or an N-oxide thereof, or a pharmaceutically acceptable salt thereof.

In another further more preferred embodiment the compound of the invention is
N-{[(2S)-7-(METHYLSULFONYL)-2,3-DIHYDRO-1,4-BENZODIOXIN-2-YL]METHYL}-PROPAN-1-AMINE;
any of its stereoisomers or any mixture of its stereoisomers, or an N-oxide thereof, or a pharmaceutically acceptable salt thereof.

In a third further more preferred embodiment the compound of the invention is
N-{[(2S)-5-FLUORO-7-(METHYLSULFONYL)-2,3-DIHYDRO-1,4-BENZODIOXIN-2-YL]METHYL}ETHANAMINE;
any of its stereoisomers or any mixture of its stereoisomers, or an N-oxide thereof, or a pharmaceutically acceptable salt thereof.

In a fourth further more preferred embodiment the compound of the invention is
N-{[(2S)-5-CHLORO-7-(METHYLSULFONYL)-2,3-DIHYDRO-1,4-BENZODIOXIN-2-YL]METHYL}ETHANAMINE;
any of its stereoisomers or any mixture of its stereoisomers, or an N-oxide thereof, or a pharmaceutically acceptable salt thereof.

Any combination of two or more of the embodiments as described above is considered within the scope of the present invention.

DEFINITION OF SUBSTITUENTS

In the context of this invention $C_1$-$C_5$ alkyl means a straight chain or branched chain of one to five carbon atoms, including but not limited to, methyl, ethyl, n-propyl, i-propyl, n-butyl, i-butyl, s-butyl, t-butyl, n-pentyl, i-pentyl, neo-pentyl.

$C_3$-$C_6$ cycloalkyl designates a cyclic alkyl group containing of from three to six carbon atoms, including cyclopropyl, cyclobutyl and cyclopentyl.

The term "allyl" refers to the group —$CH_2$—CH=$CH_2$.

Four- to six-membered heterocyclic rings comprising at least one nitrogen atom include for example, but not limited to, acetidine, pyrrolidine, piperidine and morpholine.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydro-chloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysinium, and the ammonium salt, and the like, of a chemical compound of the invention containing an anionic group. Such cationic salts may be formed by procedures well known and described in the art.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may exist in different stereoisomeric forms—including enantiomers, diastereomers or cis-trans-isomers.

The invention includes all such isomers and any mixtures thereof including racemic mixtures.

Racemic forms can be resolved into the optical antipodes by known methods and techniques. One way of separating the enantiomeric compounds (including enantiomeric intermediates) is—in the case the compound being a chiral acid—by use of an optically active amine, and liberating the diastereomeric, resolved salt by treatment with an acid. Another method for resolving racemates into the optical antipodes is based upon chromatography on an optical active matrix. Racemic compounds of the present invention can thus be resolved into their optical antipodes, e.g., by fractional crystallisation of D- or L-(tartrates, mandelates, or camphor-sulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

N-Oxides

In the context of this invention an N-oxide designates an oxide derivative of a tertiary amine, including a nitrogen atom of an aromatic N-heterocyclic compound, a non-aromatic N-heterocyclic compounds, a trialkylamine and a trialkenylamine. For example, the N-oxide of a compound containing a pyridyl may be the 1-oxy-pyridin-2, -3 or -4-yl derivative.

N-oxides of the compounds of the invention may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labeling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{11}$C, $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Persons skilled in the art will appreciate that, in order to obtain compounds of the invention in an alternative—and in some occasions, more convenient manner—the individual process steps mentioned hereinbefore may be performed in a different order, and/or the individual reactions may be performed at different stage in the overall route (i.e. chemical transformations may be performed upon different intermediates to those associated hereinbefore with a particular reaction).

Biological Activity

The typical pharmacological effects which are characteristic for dopaminergic stabilizers are an increased turnover of dopamine in the terminal areas of the ascending dopaminergic projections of the mammalian brain. This can be illustrated by measuring of changes in biochemical indices in the brain with the characteristic features of dopamine antagonists, e.g. producing increases in concentrations of dopamine metabolites such as 3,4-dihydroxyphenyl-acetic acid (DOPAC) in the striatum. The typical increase in DOPAC levels (striatum) possible to achieve is in the range of 350-400% of control.

Representative compounds of the invention are shown in Table 1.

TABLE 1

Estimated $ED_{50}$ values on increase of DOPAC (3,4-dihydroxyphenylacetic acid) in the rat striatum after systemic adminstration of test compound. For methods and statistical calculations see the enclosed tests.

| Examples | $ED_{50}$ DOPAC* µmol/kg |
|---|---|
| Example 2 | 47 (39-76) |
| Example 3 | 6.1 (5.4-8.3) |
| Example 7 | 12 (8.9-21) |
| Example 16 | 29 (24-38) |
| Example 19 | <3.7 |
| Example 21 | 6.8 (5.8-8.2) |
| Example 23 | 14 (12-17) |

The compounds according to the present invention possess dopamine-modulating properties and both they and their pharmaceutical compositions are useful in treating numerous central nervous system disorders, including both psychiatric and neurological disorders. Particularly, the compounds and their pharmaceutical compositions may be used in the treatment of CNS disorders were the dopaminergic system is dysfunctional due to direct or indirect causes.

The compounds and compositions according to the invention can be used to improve all forms of psychosis, including schizophrenia and schizophreniform and bipolar disorders as well as drug induced psychotic disorders. Iatrogenic psychoses and hallucinoses and non-iatrogenic psychoses and hallucinoses may also be treated.

In a preferred embodiment the disease, disorder or condition contemplated according to the invention is a form of psychosis, in particular schizophrenia, a schizophreniform disorder, a bipolar disorder, or a drug induced psychotic disorder.

Mood and anxiety disorders, depression and obsessive-compulsive disease may also be treated with the compounds and compositions according to the invention.

Compounds with modulating effects on dopaminergic systems may also be used to improve motor and cognitive functions and in the treatment of emotional disturbances related to ageing, neurodegenerative (e.g. dementia and age-related cognitive impairment) and developmental disorders (such as Autism spectrum disorders, ADHD, Cerebral Palsy, Gilles de la Tourette's syndrome) as well as after brain injury. Such brain injury may be induced by traumatic, inflammatory, infectious, neoplastic, vascular, hypoxic or metabolic causes or by toxic reactions to exogenous chemicals, wherein the exogenous chemicals are selected from the group consisting of substances of abuse, pharmaceutical compounds and environmental toxins.

The compounds and pharmaceutical compositions according to the invention may also be used in behavioural disorders usually first diagnosed in infancy, childhood, or adolescence as well as in impulse control disorders.

They can also be used for treating substance abuse disorders as well as disorders characterized by misuse of food. They are further useful for treatment of a condition selected from the group consisting of sleep disorders, sexual disorders, eating disorders, obesitas, and headaches and other pains in conditions characterized by increased muscular tone.

Neurological indications include the use of the compounds and their pharmaceutical compositions to improve mental and motor function in Parkinson's disease, and in related parkinsonian syndromes, dyskinesias (including L-DOPA induced dyskinesias) and dystonias. They may also be used to ameliorate tics and tremor of different origins. Moreover, they may be used to relieve pain in conditions characterized by increased muscle tone.

They can also be used in the treatment of Huntington's disease and other movement disorders as well as movement disorders induced by drugs. Restless legs and related disorders as well as narcolepsy may also be treated with compounds included according to the invention.

The compounds and their pharmaceutical compositions according to the present invention can be used for the treatment of Alzheimer's disease or related dementia disorders.

The effects of compounds of the invention on spontaneous locomotion are shown in Table 2.

TABLE 2

Effects of compounds from the present invention on Locomotor activity in drug-naive rats. The animals were placed in the motility meters immediately after drug administration and locomotor activity was recorded for 60 minutes (counts/60 min ± SEM).

| Example | Control group | 3.7 µmol/kg | 11 µmol/kg | 33 µmol/kg |
|---|---|---|---|---|
| Example 2 | 10344 ± 832 | 10728 ± 1557 | 10346 ± 857 | 11427 ± 1559 |
| Example 3 | 8716 ± 1719 | 10297 ± 860 | 8973 ± 2186 | 6830 ± 128 |
| Example 7 | 8563 ± 1112 | 7905 ± 656 | 5469 ± 734 | 3334 ± 780 |
| Example 16 | 11694 ± 2724 | 13645 ± 3301 | 11807 ± 2628 | 18642 ± 2454 |
| Example 19 | 7422 ± 731 | 6123 ± 710 | 3191 ± 387 | 1936 ± 370 |
| Example 21 | 9550 ± 1385 | 12080 ± 1292 | 8930 ± 631 | 4430 ± 775 |
| Example 23 | 9144 ± 2115 | 9551 ± 1284 | 9722 ± 1247 | 7700 ± 1039 |

The effects of compounds of the invention on the increase in activity induced by direct or indirect dopaminergic agonists, i.e. d-amphetamine and congeners are shown in Table 3.

TABLE 3

Effects of compounds of the present invention on reduction of amphetamine-induced hyper-locomotion. For methods and statistical calculations see the enclosed tests.

| Example | $ED_{50}$ µmol/kg |
|---|---|
| Example 3 | 9.6 (4.0-17) |
| Example 19 | 3.4 (2.1-4.5) |
| Example 21 | 21 (12-29) |

Pharmaceutical Compositions

In another aspect the invention provides novel pharmaceutical compositions comprising a therapeutically effective amount of the chemical compound of the invention.

The present invention relates to pharmaceutical compositions comprising the compounds of the present invention, and their use in treating CNS disorders. Both organic and inorganic acids can be employed to form non-toxic pharmaceutically acceptable acid addition salts of the compounds according to the invention. Suitable acid addition salts of the compounds of the present invention include those formed with pharmaceutically acceptable salts such as those mentioned above. The pharmaceutical composition comprising a compound according to the invention may also comprise substances used to facilitate the production of the pharmaceutical preparation or the administration of the preparations. Such substances are well known to people skilled in the art and may for instance be pharmaceutically acceptable adjuvants, carriers and preservatives.

In clinical practice, the compounds according to the present invention will normally be administered orally, rectally, nasally or by injection, in the form of pharmaceutical preparations comprising the active ingredient either as a free base or as a pharmaceutically acceptable non-toxic, acid addition salt, such as the hydrochloride, lactate, acetate or sulfamate salt, in association with a pharmaceutically acceptable carrier. The carrier may be a solid, semisolid or liquid preparation. Usually the active substance will constitute between 0.1 and 99% by weight of the preparation, more specifically between 0.5 and 20% by a weight for preparations intended for injection and between 0.2 and 50% by weight for preparations suitable for oral administration.

To produce pharmaceutical preparations containing the compound according to the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinyl-pyrrolidine, and a lubricant such as magnesium stearate, calcium stearate, polyethylene glycol, waxes, paraffin, and the like, and then compressed into tablets. If coated tablets are required, the cores (prepared as described above) may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or polyethylene glycol. Hard gelatine capsules may contain granules of the active substance using either the mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Examples of tablet and capsule formulations suitable for oral administration are given below:

| Tablet I | mg/tablet |
|---|---|
| Compound | 100 |
| Lactose Ph. Eur | 182.75 |
| Croscarmellose sodium | 12.0 |
| Maize starch paste (5% w/v paste) | 2.25 |
| Magnesium stearate | 3.0 |

| Tablet II | mg/tablet |
|---|---|
| Compound | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| Tablet III | mg/tablet |
|---|---|
| Compound | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| Capsule | mg/capsule |
|---|---|
| Compound | 10 |
| Lactose Ph. Eur | 488.5 |
| Magnesium | 1.5 |

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain coloring agents, flavoring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from 0.5% to about 10% by weight. These solutions may also containing stabilizing agents and/or buffering agents and may conveniently be provided in various dosage unit ampoules. The use and administration to a patient to be treated would be readily apparent to an ordinary skill in the art.

For intranasal administration or administration by inhalation, the compounds of the present invention may be delivered in the form of a solution, dry powder or suspension. Administration may take place via a pump spray container that is squeezed or pumped by the patient or through an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. The compounds of the invention may also be administered via a dry powder inhaler, either as a finely divided powder in combination with a carrier substance (e.g. a saccharide) or as microspheres. The inhaler, pump spray or aerosol spray may be single or multi dose. The dosage may be controlled through a valve that delivers a measured amount of active compound.

The compounds of the invention may also be administered in a controlled release formulation. The compounds are released at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. The compounds may also be formulated in controlled release formulations in which release of the active compound is targeted. For example, release of the compound may be limited to a specific region of the digestive system through the pH sensitivity of the formulation. Such formulations are well known to persons skilled in the art.

Further details on techniques for formulation and administration may be found in the latest edition of Remington's Pharmaceutical Sciences (Maack Publishing Co., Easton, Pa.).

Depending upon the disorder and patient to be treated and the route of administration, the compositions may be administered at varying doses. The dosing will also depend upon the relation of potency to absorbability and the frequency and route of administration. Such doses may be administered once, twice or three or more times daily. The compounds of this invention can be administered to subjects in doses ranging from 0.01 mg to 500 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of diseases. Alternatively, the dosage level is such that a serum concentration of between 0.1 nM to 10 μM of the compound is obtained.

EXAMPLES

The invention is further illustrated in the examples below and as outlined below in Schemes 1-4, which in no way are intended to limit the scope of the invention.

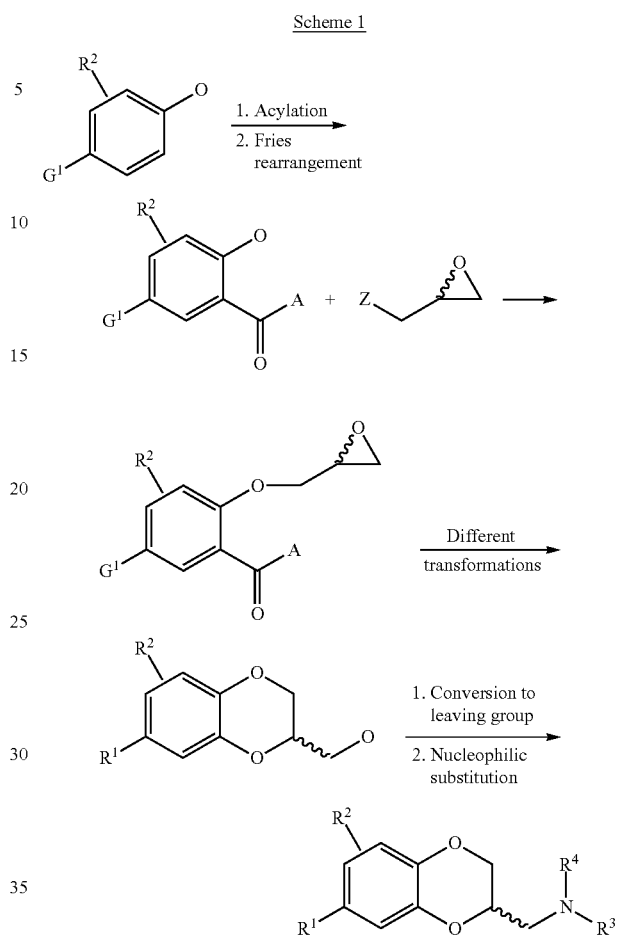

Scheme 1

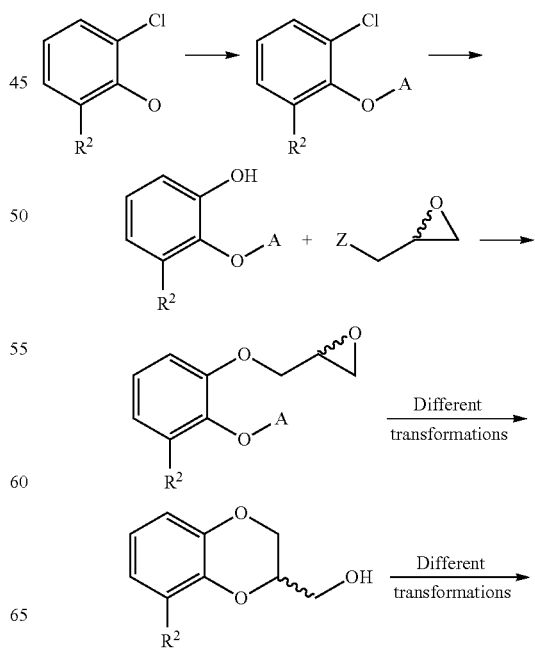

Scheme 2

21
-continued

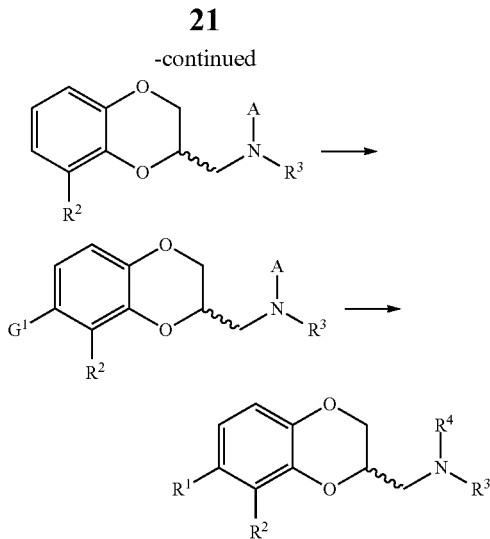

Scheme 3

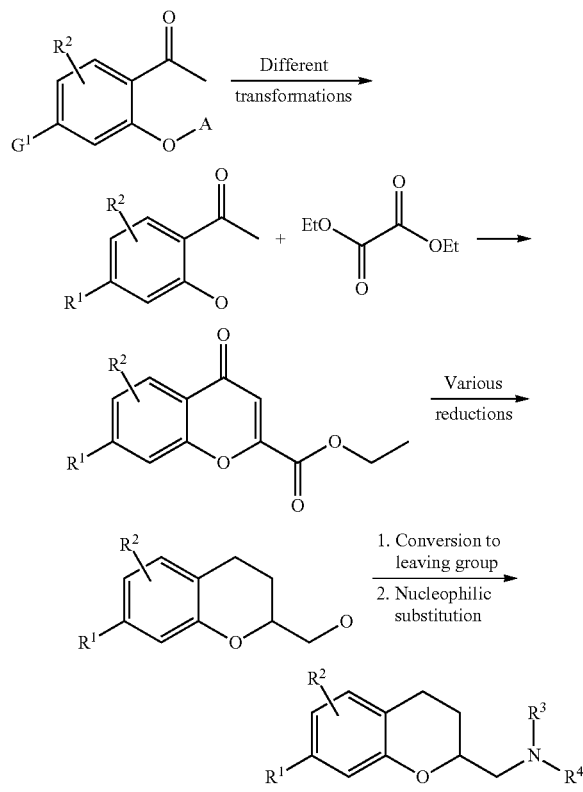

Scheme 4

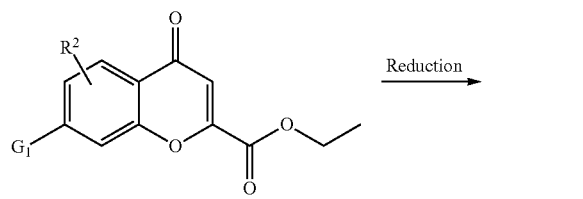

22
-continued

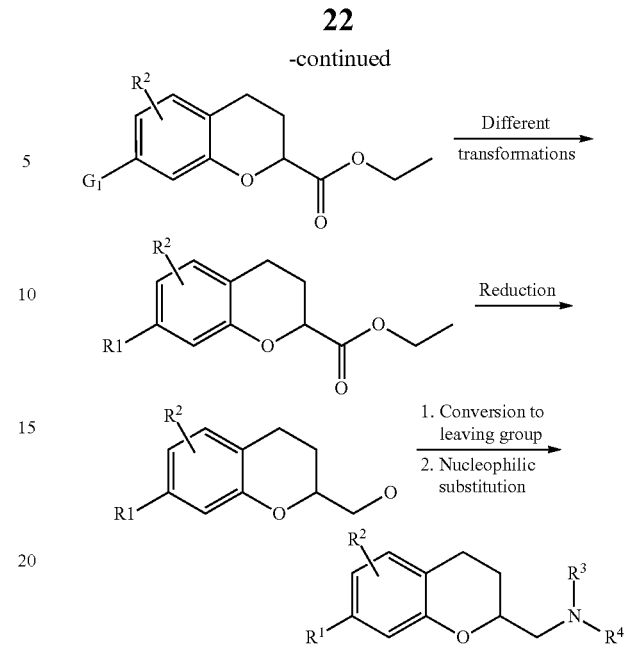

The substituents in Schemes 1-4, are as follows: z is a leaving group, $G^1$ is $R^1$ or a group that can be transformed into $R^1$, A is alkyl, hydrogen or a protecting group. $R^1$, $R^2$, $R^3$ and $R^4$ are as defined above.

Example 1

N-{[7-(METHYLSULFONYL)-2,3-DIHYDRO-1,4-BENZODIOXIN-2-YL]METHYL}-PROPAN-1-AMINE

A mixture of [7-(methylsulfonyl)-2,3-dihydro-1,4-benzodioxin-2-yl]methyl 4-methylbenzenesulfonate (0.4 g, 0.90 mmol), propan-1-amine (1 ml) and ACN (3 ml) was heated under microwave radiation at 120° C. for 30 min. Purification on SCX-3 column (TEA/MeOH) and on a small silica plug (DCM/MeOH). Yield: 0.2 g, 90%. The amine was converted to the hydrochloric acid salt and crystallized from MeOH/Et$_2$O. M.p. 223° C. MS m/z (rel. intensity, 70 eV) 285 (M+, 5), 256 (4), 207 (5), 73 (5), 72 (bp).

Example 2

N-{[(2R)-7-(METHYLSULFONYL)-2,3-DIHYDRO-1,4-BENZODIOXIN-2-YL]METHYL}-PROPAN-1-AMINE

A mixture of [(2S)-7-(methylsulfonyl)-2,3-dihydro-1,4-benzodioxin-2-yl]methyl 4-methylbenzenesulfonate (0.7 g, 1.8 mmol), propan-1-amine (1 ml) and ACN (3 ml) was heated under microwave radiation at 120° C. for 20 min. Purification on SCX-3 column (TEA/MeOH) and flash column chromatography (EtOAc/MeOH). Yield: 0.4 g, 73%. The amine was converted to the hydrochloric acid salt and crystallized from MeOH/Et$_2$O. M.p. 228° C. MS m/z (rel. intensity, 70 eV) 285 (M+, 3), 207 (4), 73 (5), 72 (bp), 70 (5). [α]=+67° (MeOH).

Example 3

N-{[(2S)-7-(METHYLSULFONYL)-2,3-DIHYDRO-1,4-BENZODIOXIN-2-YL]METHYL}-PROPAN-1-AMINE

A mixture of [(2R)-7-(methylsulfonyl)-2,3-dihydro-1,4-benzodioxin-2-yl]methyl 4-methylbenzenesulfonate (0.4 g, 0.9 mmol), propan-1-amine (1 ml) and ACN (3 ml) was heated under microwave radiation at 120° C. for 20 min. Purification on SCX-3 column (TEA/MeOH) and on a small silica plug (DCM/MeOH). Yield: 0.2 g, 90%. The amine was converted to the hydrochloric acid salt and crystallized from MeOH/Et$_2$O. M.p. 228° C. MS m/z (rel. intensity, 70 eV) 285 (M+, 2), 79 (3), 73 (5), 72 (bp), 70 (5). [α]=−73° (MeOH).

Example 4

N-{[7-(METHYLSULFONYL)-2,3-DIHYDRO-1,4-BENZODIOXIN-2-YL]METHYL}ETHANAMINE

A mixture of [7-(methylsulfonyl)-2,3-dihydro-1,4-benzodioxin-2-yl]methyl 4-methylbenzenesulfonate (0.7 g, 1.8 mmol), ethanamine (1 ml, 70% in water) and ACN (3 ml) was heated under microwave radiation at 120° C. for 30 min. Purification on flash column chromatography and on SCX-3 column (TEA/MeOH). Yield: 0.4 g, 72%. The amine was converted to the hydrochloric acid salt and was crystallized from MeOH/Et$_2$O. M.p. 261° C. MS m/z (rel. intensity, 70 eV) 271 (M+, 19), 226 (4), 207 (9), 79 (6), 58 (bp).

Example 5

N-{[(2S)-7-(METHYLSULFONYL)-2,3-DIHYDRO-1,4-BENZODIOXIN-2-YL]METHYL}ETHANAMINE

A mixture of [(2R)-7-(methylsulfonyl)-2,3-dihydro-1,4-benzodioxin-2-yl]methyl 4-methylbenzenesulfonate (1.0 g, 2.51 mmol), ethanamine (2 ml, 70% in water) and ACN (6 ml) was heated under microwave radiation at 120° C. for 20 min. Purification on SCX-3 column (TEA/MeOH) and flash column chromatography (Isooctane/EtOAc/MeOH). Yield: 0.53 g, 78%. The amine was converted to the hydrochloric acid salt and crystallized from MeOH/Et$_2$O. M.p. 271° C. MS m/z (rel. intensity, 70 eV) 271 (M+, 29), 58 (100), 59 (10), 272 (7), 79 (5). [α]=−66° (MeOH).

Example 6

1-{[7-(METHYLSULFONYL)-2,3-DIHYDRO-1,4-BENZODIOXIN-2-YL]METHYL}PIPERIDINE

A mixture of [7-(methylsulfonyl)-2,3-dihydro-1,4-benzodioxin-2-yl]methyl 4-methylbenzenesulfonate (0.6 g, 1.5 mmol), piperidine (1 ml) and ACN (3 ml) was heated under microwave radiation at 120° C. for 20 min. Purification on SCX-3 column (TEA/MeOH) and by flash chromatography through a small plug of silica (DCM/MeOH, 5:95). Yield: 0.4 g, 85%. The amine was converted to the hydrochloric acid salt and crystallized from MeOH/Et$_2$O. M.p. 248° C. MS m/z (rel. intensity, 70 eV) 311 (M+, 1), 310 (M+, 2), 207 (3), 99 (7), 98 (bp).

Example 7

1-{[(2S)-7-(METHYLSULFONYL)-2,3-DIHYDRO-1,4-BENZODIOXIN-2-YL]METHYL}PIPERIDINE

Preparation according to Example 3 using [(2R)-7-(methylsulfonyl)-2,3-dihydro-1,4-benzodioxin-2-yl]methyl 4-methylbenzenesulfonate (0.4 g, 1 mmol), piperidine (1 ml) and ACN (3 ml). Yield: 0.3 g, 94%. The amine was converted to the hydrochloric acid salt and crystallized from MeOH/Et$_2$O. M.p. 227° C. MS m/z (rel. intensity, 70 eV) 311 (M+, 1), 310 (M+, 1), 99 (7), 98 (bp), 79 (2), 55 (4). [α]=−65° (MeOH).

Example 8

1-{[(2R)-7-(METHYLSULFONYL)-2,3-DIHYDRO-1,4-BENZODIOXIN-2-YL]METHYL}PIPERIDINE

A mixture of [(2S)-7-(methylsulfonyl)-2,3-dihydro-1,4-benzodioxin-2-yl]methyl 4-methylbenzenesulfonate (0.5 g, 1.1 mmol), piperidine (1 ml) and ACN (3 ml) was heated under microwave radiation at 120° C. for 20 min. Purification on SCX-3 column (TEA/MeOH) and by flash chromatography, first with (DCM/MeOH) as eluent and then (EtOAc/MeOH) as eluent. Yield: 0.2 g, 72%. The amine was converted to the hydrochloric acid salt and crystallized from EtOH/Et$_2$O. M.p. 226° C. MS m/z (rel. intensity, 70 eV) 311 (M+, 1), 310 (M+, 1), 99 (7), 98 (bp), 79 (2), 55 (4). [α]=+62° (MeOH).

Example 9

N-METHYL-1-[7-(METHYLSULFONYL)-2,3-DIHYDRO-1,4-BENZODIOXIN-2-YL]METHANAMINE

Preparation according to Example 5 using [7-(methylsulfonyl)-2,3-dihydro-1,4-benzodioxin-2-yl]methyl 4-methylbenzenesulfonate (0.4 g, 0.9 mmol), methanamine (33% in EtOH, 1 ml) and ACN (3 ml). Yield: 0.2 g, 76%. The amine was converted to the hydrochloric acid salt and crystallized from MeOH/Et$_2$O. M.p. 273° C. MS m/z (rel. intensity, 70 eV) 257 (M+, 79), 79 (bp), 70 (70), 63 (59), 51 (83).

Example 10

N-METHYL-1-[(2S)-7-(METHYLSULFONYL)-2,3-DIHYDRO-1,4-BENZODIOXIN-2-YL]METHANAMINE

Preparation according to Example 3 using [(2R)-7-(methylsulfonyl)-2,3-dihydro-1,4-benzodioxin-2-yl]methyl 4-methylbenzenesulfonate (0.4 g, 1 mmol), methanamine (33% in EtOH, 1 ml) and ACN (3 ml). Yield: 0.2 g, 89%. The amine was converted to the hydrochloric acid salt and crystallized from MeOH/Et$_2$O. M.p. 248° C. MS m/z (rel. intensity, 70 eV) 257 (M+, bp), 79 (86), 70 (59), 63 (50), 51 (71). [α]=−59° (MeOH).

Example 11

1-{[7-(METHYLSULFONYL)-2,3-DIHYDRO-1,4-BENZODIOXIN-2-YL]METHYL}PYRROLIDINE

A mixture of [7-(methylsulfonyl)-2,3-dihydro-1,4-benzodioxin-2-yl]methyl 4-methylbenzenesulfonate (0.4 g, 0.9 mmol), pyrrolidine (1 ml) and ACN (3 ml) was heated under microwave radiation at 120° C. for 20 min. Purification on SCX-3 column (TEA/MeOH) and twice on flash column chromatography (Isooctane/EtOAc/MeOH). Yield: 0.2 g, 75%. The amine was converted to the hydrochloric acid salt and crystallized from MeOH/Et$_2$O. M.p. 221° C. MS m/z (rel. intensity, 70 eV) 297 (M+, 1), 85 (6), 84 (bp), 79 (2), 55 (4).

Example 12

3-METHYL-1-{[(2R)-7-(METHYLSULFONYL)-2,3-DIHYDRO-1,4-BENZODIOXIN-2-YL]METHYL}PIPERIDINE

A mixture of [(2S)-7-(methylsulfonyl)-2,3-dihydro-1,4-benzodioxin-2-yl]methyl 4-methylbenzenesulfonate (0.20 g, 0.5 mmol), 3-methylpiperidine (0.35 ml, 3 mmol) and ACN (2 ml) was heated under microwave radiation at 120° C. for 30 min. Purification on flash column chromatography (Isooctane/EtOAc/MeOH). Yield: 0.097 g, 85%. The amine was converted to the fumaric acid salt and crystallized from MeOH/(i-Pr)$_2$O. M.p. 159° C. MS m/z (rel. intensity, 70 eV) 325 (M+, 1), 113 (83), 112 (bp), 69 (43), 55 (46). [α]=+50° (MeOH).

Example 13

2-METHYL-N-{[(2R)-7-(METHYLSULFONYL)-2,3-DIHYDRO-1,4-BENZODIOXIN-2-YL]METHYL}PROPAN-1-AMINE

A mixture of [(2S)-7-(methylsulfonyl)-2,3-dihydro-1,4-benzodioxin-2-yl]methyl 4-methylbenzenesulfonate (0.2 g, 0.5 mmol), 2-methylpropane-1-amine (1 ml) and ACN (2 ml) was heated under microwave radiation at 120° C. for 30 min. Purification on SCX-3 column (TEA/MeOH) and flash column chromatography (EtOAc/MeOH). Yield: 0.1 g, 77%. The amine was converted to the hydrochloric acid salt and crystallized from MeOH/Et$_2$O. M.p. 213° C. MS m/z (rel. intensity, 70 eV) 299 (M+, 4), 256 (16), 207 (11), 86 (bp), 57 (8). [α]=+65° (MeOH).

Example 14

2-METHYL-N-{[(2S)-7-(METHYLSULFONYL)-2,3-DIHYDRO-1,4-BENZODIOXIN-2-YL]METHYL}PROPAN-1-AMINE

A mixture of [(2R)-7-(methylsulfonyl)-2,3-dihydro-1,4-benzodioxin-2-yl]methyl 4-methylbenzenesulfonate (0.19 g, 0.48 mmol), 2-methylpropane-1-amine (0.9 ml) and ACN (3 ml) was heated under microwave radiation at 120° C. for 20 min. Purification on SCX-3 column (TEA/MeOH) and flash column chromatography (DCM/MeOH). Yield: 0.11 g, 74%. The amine was converted to the hydrochloric acid salt and crystallized from MeOH/Et$_2$O. M.p. 214° C. MS m/z (rel. intensity, 70 eV) 299 (M+, 6), 86 (100), 256 (21), 57 (8), 70 (6). [α]=−58° (MeOH).

Example 15

N-METHYL-N-{[7-(METHYLSULFONYL)-2,3-DIHYDRO-1,4-BENZODIOXIN-2-YL]METHYL}PROPAN-1-AMINE

Preparation according to Example 14 using [7-(methylsulfonyl)-2,3-dihydro-1,4-benzodioxin-2-yl]methyl 4-methylbenzenesulfonate (0.175 g, 0.44 mmol), N-methylpropan-1-amine (0.35 ml) and ACN (2 ml). Yield: 0.11 g, 84%. The amine was converted to the hydrochloric acid salt and crystallized from MeOH/Et$_2$O. M.p. 222° C. MS m/z (rel. intensity, 70 eV) 299 (M+, 1) 86 (100), 58 (8), 84 (6), 87 (6).

Example 16

N-{[7-(METHYLSULFONYL)-2,3-DIHYDRO-1,4-BENZODIOXIN-2-YL]METHYL}-N-PROPYL-PROPAN-1-AMINE

Preparation according to Example 14 using [7-(methylsulfonyl)-2,3-dihydro-1,4-benzodioxin-2-yl]methyl 4-methylbenzenesulfonate (0.175 g, 0.44 mmol), N-propylpropan-1-amine (1 ml) and ACN (3 ml). Yield: 0.11 g, 77%. The amine was converted to the hydrochloric acid salt and crystallized from MeOH/Et$_2$O. M.p. 182° C. MS m/z (rel. intensity, 70 eV) 327 (M+, 1) 114 (100), 298 (17), 115 (8), 86 (6).

Example 17

N-{[5-FLUORO-7-(METHYLSULFONYL)-2,3-DIHYDRO-1,4-BENZODIOXIN-2-YL]METHYL}-N-PROPAN-1-AMINE

Preparation according to Example 5 using [5-fluoro-7-(methylsulfonyl)-2,3-dihydro-1,4-benzodioxin-2-yl]methyl 4-methylbenzenesulfonate (0.3 g, 0.7 mmol), propan-1-amine (1 ml) and ACN (2 ml). Yield: 0.2 g, 70%. The amine was converted to the hydrochloric acid salt and crystallized from MeOH/Et$_2$O. M.p. 198° C. MS m/z (rel. intensity, 70 eV) 303 (M+, 10), 281 (38), 207 (85), 72 (bp), 70 (39).

Example 18

N-{[5-FLUORO-7-(METHYLSULFONYL)-2,3-DIHYDRO-1,4-BENZODIOXIN-2-YL]METHYL}ETHANAMINE

A mixture of [5-fluoro-7-(methylsulfonyl)-2,3-dihydro-1,4-benzodioxin-2-yl]methyl 4-methylbenzenesulfonate (0.3 g, 0.8 mmol), ethanamine (1 ml, 70% in water) and ACN (2 ml) was heated under microwave radiation at 120° C. for 20 min. Purification on SCX-3 column (TEA/MeOH) and on flash column chromatography (Isooctane/EtOAc/MeOH). Yield: 0.1 g, 61%. The amine was converted to the hydrochloric acid salt and crystallized from EtOH. M.p. 256° C. MS m/z (rel. intensity, 70 eV) 289 (M+, 12), 70 (17), 59 (20), 58 (bp), 56 (19).

Example 19

N-{[(2S)-5-FLUORO-7-(METHYLSULFONYL)-2,3-DIHYDRO-1,4-BENZODIOXIN-2-YL]METHYL}ETHANAMINE

Preparation according to Example 5 using [(2R)-5-fluoro-7-(methylsulfonyl)-2,3-dihydro-1,4-benzodioxin-2-yl]methyl 4-methylbenzenesulfonate (0.56 g, 1.33 mmol), ethanamine (1 ml, 70% in water) and ACN (3 ml). Yield: 0.32 g, 83%. The amine was converted to the hydrochloric acid salt and crystallized from MeOH/Et$_2$O. M.p. 274° C. MS m/z (rel. intensity, 70 eV) 289 (M+, 3), 70 (3), 59 (4), 58 (bp), 56 (3). [α]=−58° (MeOH).

Example 20

1-[5-FLUORO-7-(METHYLSULFONYL)-2,3-DI-HYDRO-1,4-BENZODIOXIN-2-YL]-N-METHYL-METHANAMINE

A mixture of [5-fluoro-7-(methylsulfonyl)-2,3-dihydro-1,4-benzodioxin-2-yl]methyl 4-methylbenzenesulfonate (0.4 g, 1 mmol), methanamine (1 ml, 40% in water) and ACN (3 ml) was heated under microwave radiation at 120° C. for 20 min. Purification on flash column chromatography (EtOAc/MeOH) gave the title compound. Yield: 0.2 g, 69%. The amine was converted to the hydrochloric acid salt and crystallized from EtOH/Et$_2$O. M.p. 243° C. MS m/z (rel. intensity, 70 eV) 275 (M+, 81), 97 (48), 70 (bp), 69 (73), 63 (58).

Example 21

N-{[(2S)-5-FLUORO-7-(METHYLSULFONYL)-2,3-DIHYDRO-1,4-BENZODIOXIN-2-YL]METHYL}PROPAN-1-AMINE

To a mixture of N-benzyl-N-{[(2S)-8-fluoro-7-(methylsulfonyl)-2,3-dihydro-1,4-benzodioxin-2-yl]methyl}propan-1-amine (0.36 g, 0.97 mmol), methanol (5 ml) and Pd/C (0.1 g) under N$_2$, triethylsilane (4.7 ml, 30 mmol) was added dropwise. The solution was stirred for 16 h at room temperature and filtered through Celite. The solvent was evaporated to dryness. Flash column chromatography (Isooctane/EtOAc/Et$_3$N) yielded the title compound. Yield: 0.12 g, 41%. The amine was converted to the hydrochloric acid salt and crystallized from MeOH/Et$_2$O. M.p. 226° C. MS m/z (rel. intensity, 70 eV) 303 (M+, 4), 274 (7), 73 (5), 72 (bp), 70 (8). [α]=−60° (MeOH).

Example 22

N-{[(2S)-7-(TRIFLUOROMETHYLSULFONYL)-2,3-DIHYDRO-1,4-BENZODIOXIN-2-YL]METHYL}ETHANAMINE

Preparation according to Example 2 using [(2R)-7-(trifluoromethylsulfonyl)-2,3-dihydro-1,4-benzodioxin-2-yl]methyl-4-methylbenzenesulfonate (0.27 g, 0.68 mmol), ethanamine (1 ml, 70% in water) and ACN (2 ml). Yield: 0.170 g, 76%. The amine was converted to the hydrochloric acid salt and recrystallized from acetonitrile. M.p. 208° C. MS m/z (rel. intensity, 70 eV) 325 (M+, 1) 58 (bp), 56 (8), 79 (5), 59 (4). [α]=−40° (MeOH).

Example 23

N-{[7-(METHYLSULFONYL)-3,4-DIHYDRO-2H-CHROMEN-2-YL]METHYL}-N—PROPAN-1-AMINE

A mixture of [7-(methylsulfonyl)-3,4-dihydro-2H-chromen-2-yl]methyl 4-methylbenzenesulfonate (0.30 g, 0.75 mmol), propan-1-amine (1 ml) and acetonitrile (5 ml) was stirred at reflux for overnight. Purification on SCX-3 column (TEA/MeOH) and by preparative HPLC (MeOH/NH$_3$ buffer). Yield: 0.19 g, 89%. The amine was converted to the hydrochloric acid salt and recrystallized from acetonitrile. M.p. 214° C. MS m/z (rel. intensity, 70 eV) 283 (M+, 12), 254 (12), 131 (6), 73 (5), 72 (bp).

Example 24

N-{[(2S)-7-(TRIFLUOROMETHYLSULFONYL)-2,3-DIHYDRO-1,4-BENZODIOXIN-2-YL]METHYL}PROPAN-1-AMINE

Preparation according to Example 2 using [(2R)-7-(trifluoromethylsulfonyl)-2,3-dihydro-1,4-benzodioxin-2-yl]methyl-4-methylbenzenesulfonate (0.39 g, 0.98 mmol), propan-1-amine (1 ml) and ACN (2 ml). Yield: 0.150 g, 45%. The amine was converted to the hydrochloric acid salt and recrystallized from acetonitrile. M.p. 175° C. MS m/z (rel. intensity, 70 eV) 339 (M+, 2) 310 (10), 270 (6), 72 (bp), 70 (6). [α]=+50° (MeOH).

Example 25

N-{[7-(METHYLSULFONYL)-2,3-DIHYDRO-1,4-BENZODIOXIN-2-YL]METHYL}PROP-2-EN-1-AMINE

A mixture of [7-(methylsulfonyl)-2,3-dihydro-1,4-benzodioxin-2-yl]methyl 4-methylbenzenesulfonate (0.018 g, 0.046 mmol), prop-2-en-1-amine (0.5 ml) and ACN (3 ml) was heated under microwave radiation at 120° C. for 20 min. MS m/z (rel. intensity, 70 eV) 283 (M+, 4), 79 (4), 71 (6), 70 (bp), 68 (4).

Example 26

4-{[7-(METHYLSULFONYL)-2,3-DIHYDRO-1,4-BENZODIOXIN-2-YL]METHYL}MORPHOLINE

Preparation according to Example 25 using [7-(methylsulfonyl)-2,3-dihydro-1,4-benzodioxin-2-yl]methyl 4-methylbenzenesulfonate (0.018 g, 0.046 mmol), morpholine (0.5 ml), ACN (3 ml). MS m/z (rel. intensity, 70 eV) 313 (M+, 1), 101 (6), 100 (bp), 70 (2), 56 (4).

Example 27

N-{[7-(METHYLSULFONYL)-2,3-DIHYDRO-1,4-BENZODIOXIN-2-YL]METHYL}BUTAN-1-AMINE

Preparation according to Example 25 using [7-(methylsulfonyl)-2,3-dihydro-1,4-benzodioxin-2-yl]methyl 4-methylbenzenesulfonate (0.018 g, 0.046 mmol), butan-1-amine (0.5 ml), ACN (3 ml). MS m/z (rel. intensity, 70 eV) 299 (M+, 6), 256 (5), 87 (6), 86 (bp), 70 (5).

Example 28

N,N-DIMETHYL-N-{[7-(METHYLSULFONYL)-2,3-DIHYDRO-1,4-BENZODIOXIN-2-YL]METHANAMINE

Preparation according to Example 25 using [7-(methylsulfonyl)-2,3-dihydro-1,4-benzodioxin-2-yl]methyl 4-methylbenzenesulfonate (0.018 g, 0.046 mmol), N-methylmethanamine (0.5 ml), ACN (3 ml). MS m/z (rel. intensity, 70 eV) 271 (M+, 1), 84 (2), 79 (3), 59 (4), 58 (bp).

Example 29

N-ETHYL-N-{[7-(METHYLSULFONYL)-2,3-DIHYDRO-1,4-BENZODIOXIN-2-YL]METHYL}ETHANAMINE

Preparation according to Example 25 using [7-(methylsulfonyl)-2,3-dihydro-1,4-benzodioxin-2-yl]methyl 4-methylbenzenesulfonate (0.018 g, 0.046 mmol), N-ethylethanamine (0.5 ml), ACN (3 ml). MS m/z (rel. intensity, 70 eV) 299 (M+, 1), 87 (6), 86 (bp), 84 (2), 58 (5).

Example 30

N-{[7-(METHYLSULFONYL)-2,3-DIHYDRO-1,4-BENZODIOXIN-2-YL]METHYL}PROPAN-2-AMINE

Preparation according to Example 25 using [7-(methylsulfonyl)-2,3-dihydro-1,4-benzodioxin-2-yl]methyl 4-methylbenzenesulfonate (0.018 g, 0.046 mmol), propan-2-amine (0.5 ml), ACN (3 ml). MS m/z (rel. intensity, 70 eV) 211 (34), 139 (4), 98 (5), 70 (7), 58 (bp).

Example 31

N-ETHYL-N-{[7-(METHYLSULFONYL)-2,3-DIHYDRO-1,4-BENZODIOXIN-2-YL]METHYL}-N-PROPAN-1-AMINE

Preparation according to Example 25 using [7-(methylsulfonyl)-2,3-dihydro-1,4-benzodioxin-2-yl]methyl 4-methylbenzenesulfonate (0.018 g, 0.046 mmol), N-ethylpropan-1-amine (0.5 ml), ACN (3 ml). MS m/z (rel. intensity, 70 eV) 299 (M+, 2), 270 (9), 87 (6), 86 (bp), 58 (7).

Example 32

2-({[7-(METHYLSULFONYL)-2,3-DIHYDRO-1,4-BENZODIOXIN-2-YL]METHYL}AMINO)ETHANOL

Preparation according to Example 25 using [7-(methylsulfonyl)-2,3-dihydro-1,4-benzodioxin-2-yl]methyl 4-methylbenzenesulfonate (0.018 g, 0.046 mmol), 2-aminoethanol (0.5 ml), ACN (3 ml). $^1$H-NMR (400 MHz, CD$_3$OD): δ 7.47 (1H, d, J 2), δ 7.42 (1H, dd, J 8, 2), δ 7.07 (1H, d, J 8.0), δ 4.43 (1H, dd, J 12, 2.4), δ 4.37 (1H, m)), δ 4.09 (1H, dd J 12, 7.2), δ 3.68 (2H, t, J 5.6), δ 3.07 (3H, s), δ 2.94 (2H, m), 2.80 (2H, m) ppm (J-values are in Hz and shifts relative to solvent-peak at 3.31 ppm).

Example 33

N-METHYL-N-{[7-(METHYLSULFONYL)-2,3-DIHYDRO-1,4-BENZODIOXIN-2-YL]METHYL}ETHANAMINE

Preparation according to Example 25 using [7-(methylsulfonyl)-2,3-dihydro-1,4-benzodioxin-2-yl]methyl 4-methylbenzenesulfonate (0.018 g, 0.046 mmol), N-methylethanamine (0.5 ml), ACN (3 ml). MS m/z (rel. intensity, 70 eV) 285 (M+, 1), 84 (2), 79 (2), 73 (5), 72 (bp).

Example 34

2-METHOXY-N-{[7-(METHYLSULFONYL)-2,3-DIHYDRO-1,4-BENZODIOXIN-2-YL]METHYL}ETHANAMINE

Preparation according to Example 25 using [7-(methylsulfonyl)-2,3-dihydro-1,4-benzodioxin-2-yl]methyl 4-methylbenzenesulfonate (0.018 g, 0.046 mmol), 2-methoxyethanamine (0.5 ml), ACN (3 ml). MS m/z (rel. intensity, 70 eV) 301 (M+, 2), 256 (19), 88 (bp), 56 (12), 58 (7).

Example 35

1-{[7-(METHYLSULFONYL)-2,3-DIHYDRO-1,4-BENZODIOXIN-2-YL]METHYL}AZETIDINE

Preparation according to Example 25 using [7-(methylsulfonyl)-2,3-dihydro-1,4-benzodioxin-2-yl]methyl 4-methylbenzenesulfonate (0.018 g, 0.046 mmol), 2-azetidine (0.1 ml), ACN (3 ml). MS m/z (rel. intensity, 70 eV) 283 (M+, 1), 79 (3), 71 (5), 70 (bp), 51 (3).

Example 36

2-METHYL-N-{[7-(METHYLSULFONYL)-2,3-DIHYDRO-1,4-BENZODIOXIN-2-YL]METHYL}PROPAN-1-AMINE

Preparation according to Example 25 using [7-(methylsulfonyl)-2,3-dihydro-1,4-benzodioxin-2-yl]methyl 4-methylbenzenesulfonate (0.018 g, 0.046 mmol), 2-methylpropan-1-amine (0.5 ml), ACN (3 ml). MS m/z (rel. intensity, 70 eV) 299 (M+, 6), 256 (20), 86 (bp), 70 (6), 57 (8).

Example 37

N-{[(2S)-8-FLUORO-7-(METHYLSULFONYL)-2,3-DIHYDRO-1,4-BENZODIOXIN-2-YL]METHYL}ETHANAMINE

Preparation according to Example 21, using N-benzyl-N-{[(2S)-8-fluoro-7-(methylsulfonyl)-2,3-dihydro-1,4-benzodioxin-2-yl]methyl}, ethanamine (0.95 g, 2.5 mmol), methanol (5 ml), Pd/C (0.2 g) and triethylsilane (12 ml, 75 mmol). Yield 0.27 g, 37%. The amine was converted to the hydrochloric acid salt and crystallized from MeOH/Et$_2$O. M.p. 270° C. MS m/z (rel. intensity, 70 eV) 289 (M+, 5), 97 (4), 69 (4), 58 (bp), 56 (5). [α]=−64° (MeOH).

Example 38

N-{[(2S)-5-CHLORO-7-(METHYLSULFONYL)-2,3-DIHYDRO-1,4-BENZODIOXIN-2-YL]METHYL}ETHANAMINE

Preparation according to Example 5 using [(2R)-5-chloro-7-(methylsulfonyl)-2,3-dihydro-1,4-benzodioxin-2-yl]methyl 4-methylbenzenesulfonate (0.47 g, 1.09 mmol), ethanamine (1 ml, 70% in water) and ACN (7 ml). Yield: 0.278 g, 83%. The amine was converted to the hydrochloric acid salt and crystallized from MeOH/Et$_2$O. M.p. 267° C. MS m/z (rel. intensity, 70 eV) 305 (M+, 4), 63 (3), 59 (4), 58 (bp), 56 (5). [α]=−62° (MeOH).

Example 39

N-{[(2S)-7-(METHYLSULFONYL)-2,3-DIHYDRO-1,4-BENZODIOXIN-2-YL]METHYL}-N-(3,3,3-TRIFLUOROPROPYL)AMINE

A mixture of [(2S)-7-(methylsulfonyl)-2,3-dihydro-1,4-benzodioxin-2-yl]methylamine (0.31 g, 1.27 mmol), 1,1,1-trifluoro-3-iodopropane (0.16 ml, 1.4 mmol) $K_2CO_3$ (0.35 g, 2.5 mmol) and ACN (4 ml) was heated under microwave radiation at 120° C. for 40 min. The product was evaporated to dryness and was purified by preparative HPLC (MeOH/$NH_3$ buffer). Yield: 0.19 g, 44%. The amine was converted to the hydrochloric acid salt and was crystallized from MeOH/$Et_2O$. M.p. 204° C. MS m/z (rel. intensity, 70 eV) 339 (M+, 3), 127 (5), 126 (bp), 79 (4), 51 (4). [α]=−52° (MeOH).

Example 40

N-{[(2S)-5-FLUORO-7-(METHYLSULFONYL)-2,3-DIHYDRO-1,4-BENZODIOXIN-2-YL]METHYL}-N-(3,3,3-TRIFLUOROPROPYL)AMINE

A mixture of 1-[(2S)-5-fluoro-7-(methylsulfonyl)-2,3-dihydro-1,4-benzodioxin-2-yl]methaneamine (0.3 g, 1.1 mmol), 1,1,1-trifluoro-3-iodopropane (0.16 ml, 1.4 mmol) $K_2CO_3$ (0.32 g, 2.3 mmol) and ACN (4 ml) was heated under microwave radiation at 120° C. for 30 min. The mixture was filtrated and evaporated to dryness and the product was purified by flash column chromatography (EtOAc). Yield: 0.12 g, 31%. The amine was converted to the hydrochloric acid salt and crystallized from MeOH/$Et_2O$. M.p. 233° C. MS m/z (rel. intensity, 70 eV) 357 (M+, 1), 274 (3), 127 (5), 126 (bp), 69 (3). [α]=−53° (MeOH).

Example 41

1-[(2S)-5-FLUORO-7-(METHYLSULFONYL)-2,3-DIHYDRO-1,4-BENZODIOXIN-2-YL]-N-METHYLMETHANAMINE

A mixture of [(2R)-7-(trifluoromethyl)-2,3-dihydro-1,4-benzodioxin-2-yl]methyl 4-methylbenzenesulfonate (0.7 g, 1.7 mmol), methanamine (1 ml, 40% in water) and ACN (3 ml) was heated under microwave radiation at 120° C. for 20 min. The mixture was evaporated to dryness and the product was purified by flash column chromatography (EtOAc/MeOH). Yield 0.31 g, 65%. The amine was converted to the hydrochloric acid salt and crystallized from EtOH/MeOH/$Et_2O$. M.p. 260° C. MS m/z (rel. intensity, 70 eV) 275 (M+, 57), 97 (50), 70 (bp), 69 (80), 63 (58). [α]=−60° (MeOH).

Example 42

N-{[5-FLUORO-7-(METHYLSULFONYL)-2,3-DIHYDRO-1,4-BENZODIOXIN-2-YL]METHYL}PROP-2-EN-1-AMINE

A mixture of [5-fluoro-7-(methylsulfonyl)-2,3-dihydro-1,4-benzodioxin-2-yl]methyl-4-methylbenzenesulfonate (0.005 g, 0.012 mmol), prop-2-en-1-amine (0.5 ml) and ACN (2.5 ml) was heated under microwave radiation at 120° C. for 20 min. MS m/z (rel. intensity, 70 eV) 301 (M+, 2), 71 (5) 70 (bp), 69 (4) 68 (5).

Example 43

4-{[5-FLUORO-7-(METHYLSULFONYL)-2,3-DIHYDRO-1,4-BENZODIOXIN-2-YL]METHYL}MORPHOLINE

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), morpholine (0.5 ml), ACN (2.5 ml). MS m/z (rel. intensity, 70 eV) 331 (M+, 1), 101 (5), 100 (bp), 98 (4), 56 (5).

Example 44

N-{[5-FLUORO-7-(METHYLSULFONYL)-2,3-DIHYDRO-1,4-BENZODIOXIN-2-YL]METHYL}BUTAN-1-AMINE

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), butan-1-amine (0.5 ml), ACN (2.5 ml). MS m/z (rel. intensity, 70 eV) 317 (M+, 2), 274 (7), 87 (6), 86 (bp), 70 (6).

Example 45

N-{[5-FLUORO-7-(METHYLSULFONYL)-2,3-DIHYDRO-1,4-BENZODIOXIN-2-YL]METHYL}-N-PROPYLPROPAN-1-AMINE

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), N-propylpropan-1-amine (0.5 ml), ACN (2.5 ml). MS m/z (rel. intensity, 70 eV) 345 (M+, 0.5), 316 (21), 115 (8), 114 (bp), 112 (6).

Example 46

1-[5-FLUORO-7-(METHYLSULFONYL)-2,3-DIHYDRO-1,4-BENZODIOXIN-2-YL]-N,N-DIMETHYLMETHANAMINE

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), N-methylmethanamine (0.5 ml, 2.0 M in MeOH), ACN (2.5 ml). MS m/z (rel. intensity, 70 eV) 289 (M+, 1), 84 (2), 69 (2), 59 (3), 58 (bp).

Example 47

N-ETHYL-N-{[5-FLUORO-7-(METHYLSULFONYL)-2,3-DIHYDRO-1,4-BENZODIOXIN-2-YL]METHYL}ETHANAMINE

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), N-ethylethanamine (0.5 ml), ACN (2.5 ml). MS m/z (rel. intensity, 70 eV) 317 (M+, 0.2), 87 (6), 86 (bp), 58 (5), 56 (3).

Example 48

N-{[5-FLUORO-7-(METHYLSULFONYL)-2,3-DIHYDRO-1,4-BENZODIOXIN-2-YL]METHYL}PROPAN-2-AMINE

Preparation according to Example 42 using [5-fluoro-7-(methylsulfonyl)-2,3-dihydro-1,4-benzodioxin-2-yl]methyl- 4-methylbenzenesulfonate (0.005 g, 0.012 mmol), propan-2-amine (0.5 ml), ACN (2.5 ml). MS m/z (rel. intensity, 70 eV) 303 (M+, 2), 288 (17), 84 (6), 72 (bp), 56 (6).

Example 49

N-{[5-FLUORO-7-(METHYLSULFONYL)-2,3-DIHYDRO-1,4-BENZODIOXIN-2-YL]METHYL}-N-METHYLPROPAN-1-AMINE

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), N-methyl-propan-1-amine (0.5 ml), ACN (2.5 ml). MS m/z (rel. intensity, 70 eV) 317 (M+, 0.5), 288 (8), 86 (bp), 84 (6), 58 (8).

Example 50

N-ETHYL-N-{[5-FLUORO-7-(METHYLSULFONYL)-2,3-DIHYDRO-1,4-BENZODIOXIN-2-YL]METHYL}PROPAN-1-AMINE

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), N-ethyl-propan-1-amine (0.5 ml), ACN (2.5 ml). MS m/z (rel. intensity, 70 eV) 331 (M+, 0.5), 101 (7), 100 (bp), 98 (8), 58 (8).

Example 51

2-({[5-FLUORO-7-(METHYLSULFONYL)-2,3-DIHYDRO-1,4-BENZODIOXIN-2-YL]METHYL}AMINO)ETHANOL

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), 2-amino-ethanol (0.5 ml), ACN (2.5 ml). $^1$H-NMR (400 MHz, MeOD): δ 7.36 (2H, m), δ 4.54 (1H, dd, J 12, 2.4), δ 4.44 (1H, m), δ 4.18 (1H, dd, J 12, 7.2), δ 3.71 (2H, t, J 5.6), δ 3.13 (3H, s), δ 2.98 (2H, m), 2.81 (2H, m) ppm (J-values are in Hz and shifts relative to solvent-peak at 3.31 ppm).

Example 52

N-{[5-FLUORO-7-(METHYLSULFONYL)-2,3-DIHYDRO-1,4-BENZODIOXIN-2-YL]METHYL}-N-METHYLETHANAMINE

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), N-methylethanamine (0.5 ml), ACN (1 ml). MS m/z (rel. intensity, 70 eV) 303 (M+, 0.5), 84 (2), 73 (4), 72 (bp), 69 (2).

Example 53

N-{[5-FLUORO-7-(METHYLSULFONYL)-2,3-DIHYDRO-1,4-BENZODIOXIN-2-YL]METHYL}-2-METHOXYETHANAMINE

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), 2-methoxyethanamine (0.5 ml), ACN (2.5 ml). MS m/z (rel. intensity, 70 eV) 319 (M+, 1), 274 (23), 88 (bp), 70 (8), 56 (13).

Example 54

1-{[5-FLUORO-7-(METHYLSULFONYL)-2,3-DIHYDRO-1,4-BENZODIOXIN-2-YL]METHYL}AZETIDINE

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), azetidine (0.1 ml), ACN (2.5 ml). MS m/z (rel. intensity, 70 eV) 301 (M+, 1), 244 (3), 71 (5), 70 (bp), 69 (4).

Example 55

N-{[5-FLUORO-7-(METHYLSULFONYL)-2,3-DIHYDRO-1,4-BENZODIOXIN-2-YL]METHYL}-2-METHYLPROPAN-1-AMINE

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), 2-methyl-propan-1-amine (0.5 ml), ACN (2.5 ml). MS m/z (rel. intensity, 70 eV) 317 (M+, 2), 274 (38), 86 (bp), 70 (8), 57 (8).

Example 56

1-{[5-FLUORO-7-(METHYLSULFONYL)-2,3-DIHYDRO-1,4-BENZODIOXIN-2-YL]METHYL}PYRROLIDINE

Preparation according to Example 42 using [5-fluoro-7-(methylsulfonyl)-2,3-dihydro-1,4-benzodioxin-2-yl]methyl-4-methylbenzenesulfonate (0.005 g, 0.012 mmol), pyrrolidine (0.5 ml), ACN (2.5 ml). MS m/z (rel. intensity, 70 eV) 315 (M+, 0.7), 110 (3), 85 (6), 84 (bp), 55 (4).

Example 57

N-{[(2S)-5-CHLORO-7-(METHYLSULFONYL)-2,3-DIHYDRO-1,4-BENZODIOXIN-2-YL]METHYL}PROP-2-EN-1-AMINE

A mixture of [(2R)-5-chloro-7-(methylsulfonyl)-2,3-dihydro-1,4-benzodioxin-2-yl]methyl 4-methylbenzenesulfonate (0.027 g, 0.062 mmol), prop-2-en-1-amine (0.5 ml) and ACN (3 ml) was heated under microwave radiation at 120° C. for 20 min. MS m/z (rel. intensity, 70 eV) 317 (M+, 2), 113 (3), 71 (5), 70 (bp), 68 (3) 63 (3).

Example 58

N-{[(2S)-5-CHLORO-7-(METHYLSULFONYL)-2,3-DIHYDRO-1,4-BENZODIOXIN-2-YL]METHYL}BUTAN-1-AMINE

Preparation according to Example 57 [(2R)-5-chloro-7-(methylsulfonyl)-2,3-dihydro-1,4-benzodioxin-2-yl]methyl 4-methylbenzenesulfonate (0.027 g, 0.062 mmol), butan-1-

Example 59

N-{[(2S)-5-CHLORO-7-(METHYLSULFONYL)-2,3-DIHYDRO-1,4-BENZODIOXIN-2-YL]METHYL}-N-PROPYLPROPAN-1-AMINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), N-propylpropan-1-amine (0.5 ml), ACN (3 ml). MS m/z (rel. intensity, 70 eV) 361 (M+, 0.2), 332 (6), 115 (9), 114 (bp), 86 (7), 72 (4).

Example 60

1-[(2S)-5-CHLORO-7-(METHYLSULFONYL)-2,3-DIHYDRO-1,4-BENZODIOXIN-2-YL]-N,N-DIMETHYLMETHANAMINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), N-methylmethanamine (0.5 ml, 2.0 M in MeOH), ACN (3 ml). MS m/z (rel. intensity, 70 eV) 305 (M+, 0.4), 85 (2), 84 (3), 63 (2), 59 (4), 58 (bp).

Example 61

N-ETHYL-N-{[(2S)-5-CHLORO-7-(METHYLSULFONYL)-2,3-DIHYDRO-1,4-BENZODIOXIN-2-YL]METHYL}ETHANAMINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), N-ethylethanamine (0.5 ml), ACN (3 ml). MS m/z (rel. intensity, 70 eV) 333 (M+, 0.2), 98 (3), 87 (7), 86 (bp), 58 (6), 56 (3).

Example 62

N-{[(2S)-5-CHLORO-7-(METHYLSULFONYL)-2,3-DIHYDRO-1,4-BENZODIOXIN-2-YL]METHYL}PROPAN-2-AMINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), propan-2-amine (0.5 ml), ACN (3 ml). MS m/z (rel. intensity, 70 eV) 319 (M+, 1), 304 (8), 84 (8), 73 (6), 72 (bp), 56 (7).

Example 63

N-{[(2S)-5-CHLORO-7-(METHYLSULFONYL)-2,3-DIHYDRO-1,4-BENZODIOXIN-2-YL]METHYL}-N-METHYLPROPAN-1-AMINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), N-methyl-propan-1-amine (0.5 ml), ACN (3 ml). MS m/z (rel. intensity, 70 eV) 333 (M+, 0.3), 304 (4), 87 (6), 86 (bp), 84 (7), 58 (10).

Example 64

N-ETHYL-N-{[(2S)-5-CHLORO-7-(METHYLSULFONYL)-2,3-DIHYDRO-1,4-BENZODIOXIN-2-YL]METHYL}PROPAN-1-AMINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), N-ethylpropan-1-amine (0.5 ml), ACN (3 ml). MS m/z (rel. intensity, 70 eV) 347 (M+, 0.2), 101 (7), 100 (bp), 98 (5), 72 (8), 58 (9).

Example 65

2-({[(2S)-5-CHLORO-7-(METHYLSULFONYL)-2,3-DIHYDRO-1,4-BENZODIOXIN-2-YL]METHYL}AMINO)ETHANOL

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), 2-aminoethanol (0.5 ml), ACN (3 ml). $^1$H-NMR (400 MHz, MeOD): δ 7.57 (1H, d, J 2.3), δ 7.46 (1H, d, J 2.3), δ 4.59 (1H, dd, J 11.6, 2.4), δ 4.42 (1H, m), δ 4.21 (1H, dd, J 11.6, 7.4), δ 3.71 (2H, t, J 5.3), δ 3.14 (3H, s), δ 2.97 (2H, d, J 5.8), δ 2.82 (3H, m) ppm (J-values are in Hz and shifts relative to solvent-peak at δ 4.8 ppm).

Example 66

N-{[(2S)-5-CHLORO-7-(METHYLSULFONYL)-2,3-DIHYDRO-1,4-BENZODIOXIN-2-YL]METHYL}-N-METHYLETHANAMINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), N-methylethanamine (0.5 ml), ACN (3 ml). MS m/z (rel. intensity, 70 eV) 319 (M+, 0.3), 85 (3), 84 (3), 73 (5), 72 (bp), 63 (2).

Example 67

N-{[(2S)-5-CHLORO-7-(METHYLSULFONYL)-2,3-DIHYDRO-1,4-BENZODIOXIN-2-YL]METHYL}-2-METHOXYETHANAMINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), 2-methoxyethanamine (0.5 ml), ACN (3 ml). MS m/z (rel. intensity, 70 eV) 335 (M+, 1), 290 (18), 88 (bp), 70 (8), 58 (8), 56 (12).

Example 68

1-{[(2S)-5-CHLORO-7-(METHYLSULFONYL)-2,3-DIHYDRO-1,4-BENZODIOXIN-2-YL]METHYL}AZETIDINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), azetidine (0.1 ml), ACN (3 ml). MS m/z (rel. intensity, 70 eV) 317 (M+, 1), 85 (3), 71 (5), 70 (bp), 68 (2), 63 (3).

(Note: top of page continuation: amine (0.5 ml), ACN (3 ml). MS m/z (rel. intensity, 70 eV) 333 (M+, 2), 290 (6), 87 (7), 86 (bp), 85 (4), 70 (7).)

Example 69

N-{[(2S)-5-CHLORO-7-(METHYLSULFONYL)-2,3-DIHYDRO-1,4-BENZODIOXIN-2-YL]METHYL}-2-METHYLPROPAN-1-AMINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), 2-methylpropan-1-amine (0.5 ml), ACN (3 ml). MS m/z (rel. intensity, 70 eV) 333 (M+, 2), 292 (8), 290 (20), 86 (bp), 70 (8), 57 (9).

Example 70

1-{[(2S)-5-CHLORO-7-(METHYLSULFONYL)-2,3-DIHYDRO-1,4-BENZODIOXIN-2-YL]METHYL}PYRROLIDINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), pyrrolidine (0.5 ml), ACN (3 ml). MS m/z (rel. intensity, 70 eV) 331 (M+, 0.4), 110 (4), 85 (8), 84 (bp), 63 (2), 55 (5).

Example 71

N-{[(2S)-5-CHLORO-7-(METHYLSULFONYL)-2,3-DIHYDRO-1,4-BENZODIOXIN-2-YL]METHYL}-PROPAN-1-AMINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), propan-1-amine (0.5 ml), ACN (3 ml). MS m/z (rel. intensity, 70 eV) 319 (M+, 1), 85 (3), 73 (5), 72 (bp), 70 (7), 63 (3).

Example 72

N-{[(2S)-5-CHLORO-7-(METHYLSULFONYL)-2,3-DIHYDRO-1,4-BENZODIOXIN-2-YL]METHYL}-3-FLUOROPROPAN-1-AMINE

3-Fluoropropan-1-amine HCl-salt (0.178 g, 1.52 mmol) was basified on a SCX-3 ion exchange column (TEA/MeOH). [(2R)-5-chloro-7-(methylsulfonyl)-2,3-dihydro-1,4-benzodioxin-2-yl]methyl 4-methylbenzenesulfonate (0.027 g, 0.062 mmol) and 3-fluoropropan-1-amine (0.15 M in MeOH/TEA:4/1, 5 ml) was heated under microwave radiation at 120° C. for 1 h 20 min. MS m/z (rel. intensity, 70 eV) 337 (M+, 0.4), 91 (5), 90 (bp), 85 (3), 70 (17), 63 (3).

Example 73

N-{[(2S)-5-CHLORO-7-(METHYLSULFONYL)-2,3-DIHYDRO-1,4-BENZODIOXIN-2-YL]METHYL}-2,2-DIMETHYLPROPAN-1-AMINE

Preparation according to Example 57 using [(2R)-5-chloro-7-(methylsulfonyl)-2,3-dihydro-1,4-benzodioxin-2-yl]methyl 4-methylbenzenesulfonate (0.027 g, 0.062 mmol), 2,2-dimethylpropan-1-amine (0.5 ml), ACN (3 ml). MS m/z (rel. intensity, 70 eV) 347 (M+, 2), 332 (20), 292 (30), 290 (78), 100 (bp), 70 (16).

Example 74

1-{[(2S)-5-CHLORO-7-(METHYLSULFONYL)-2,3-DIHYDRO-1,4-BENZODIOXIN-2-YL]METHYL}PIPERIDINE

A mixture of [(2R)-5-chloro-7-(methylsulfonyl)-2,3-dihydro-1,4-benzodioxin-2-yl]methyl 4-methylbenzenesulfonate (0.49 g, 1.1 mmol), piperidine (1 ml, 10.1 mmol) and MeOH (2 ml) was heated under microwave radiation at 120° C. for 25 min. Purification on SCX-3 column (TEA/MeOH) and by flash column chromatography (MeOH/EtOAc) gave the title compound (0.31 g). The amine was converted to the hydrochloric acid salt and crystallized from MeOH/Et$_{2O}$ (0.25 g). MS m/z (rel. intensity, 70 eV) 345 (M+, 0.5), 124 (3), 99 (7), 98 (bp), 96 (2), 55 (4) [α]=−60° (MeOH).

Example 75

1-[(2S)-5-CHLORO-7-(METHYLSULFONYL)-2,3-DIHYDRO-1,4-BENZODIOXIN-2-YL]-N-METHYLMETHANAMINE

A mixture of [(2R)-5-chloro-7-(methylsulfonyl)-2,3-dihydro-1,4-benzodioxin-2-yl]methyl 4-methylbenzenesulfonate (0.48 g, 1.1 mmol), methanamine (1.5 ml, 33% in EtOH, 4 mmol) and ACN (3 ml) was heated under microwave radiation at 120° C. for 20 min. Purification on SCX-3 column (TEA/MeOH) and by flash column chromatography (MeOH/EtOAc) gave the title compound (0.18 g). The amine was converted to the hydrochloric acid salt and crystallized from MeOH/Et2O. M.p. 262° C. MS m/z (rel. intensity, 70 eV) 291 (M+, 43), 113 (57), 85 (80), 70 (bp), 63 (84), 50 (60) [α]=−61° (MeOH).

Example 76

N-{[(2S)-5-FLUORO-7-(METHYLSULFONYL)-2,3-DIHYDRO-1,4-BENZODIOXIN-2-YL]METHYL}-PROPAN-1-AMINE

A mixture of [(2R)-5-fluoro-7-(methylsulfonyl)-2,3-dihydro-1,4-benzodioxin-2-yl]methyl 4-methylbenzenesulfonate (0.2 g, 0.5 mmol), propan-1-amine (1 ml) and ACN (3 ml) was heated under microwave radiation at 120° C. for 20 min. Purification on SCX-3 column (TEA/MeOH) and by flash chromatography (isooctane/EtOAc/MeOH). Yield: 0.12 g, 79%. The amine was converted to the hydrochloric acid salt and crystallized from MeOH/Et$_2$O. M.p. 192° C. MS m/z (rel. intensity, 70 eV) 303 (M+, 2), 73 (5), 72 (bp), 70 (11), 69 (7), 63 (5). [α]=−64° (MeOH).

Example 77

2,2-DIMETHYL-N-{[(2S)-7-(METHYLSULFONYL)-2,3-DIHYDRO-1,4-BENZODIOXIN-2-YL]METHYL}PROPAN-1-AMINE

A mixture of [(2R)-7-(methylsulfonyl)-2,3-dihydro-1,4-benzodioxin-2-yl]methyl 4-methylbenzenesulfonate (0.196 g, 0.5 mmol), 2,2-dimethylpropan-1-amine (1 ml, 8.5 mmol) and ACN (3 ml) was heated under microwave radiation at 120° C. for 20 min. Purification on SCX-3 column (TEA/

MeOH) and by flash chromatography (EtOAc) gave the title compound. Yield: 0.1 g. The amine was converted to the hydrochloric acid salt and crystallized from MeOH/Et$_2$O. M.p. 242° C. MS m/z (rel. intensity, 70 eV) 313 (M+, 6), 298 (32), 257 (14), 256 (bp), 207 (12), 100 (92). [α]=−53° (MeOH).

Example 78

N-METHYL-1-[7-(METHYLSULFONYL)-3,4-DIHYDRO-2H-CHROMEN-2-YL]METHANAMINE

Preparation according to Example 25: [7-(methylsulfonyl)-3,4-dihydro-2H-chromen-2-yl]methyl 4-methylbenzenesulfonate (0.020 g, 0.0504 mmol), methanamine (33% in EtOH, 0.5 ml), ACN (3 ml). MS m/z (rel. intensity, 70 eV) 255 (M+, 92), 132 (52), 131 (bp), 77 (76), 70 (48).

Example 79

N-{[7-(METHYLSULFONYL)-3,4-DIHYDRO-2H-CHROMEN-2-YL]METHYL}ETHANAMINE

Preparation according to Example 25: [7-(methylsulfonyl)-3,4-dihydro-2H-chromen-2-yl]methyl 4-methylbenzenesulfonate (0.020 g, 0.0504 mmol), ethanamine (2.0 M in MeOH, 0.5 ml), ACN (3 ml). MS m/z (rel. intensity, 70 eV) 269 (M+, 5), 131 (6), 77 (6), 58 (bp), 56 (4).

Example 80

N-{[7-(METHYLSULFONYL)-3,4-DIHYDRO-2H-CHROMEN-2-YL]METHYL}PROP-2-EN-1-AMINE

Preparation according to Example 25: [7-(methylsulfonyl)-3,4-dihydro-2H-chromen-2-yl]methyl 4-methylbenzenesulfonate (0.020 g, 0.0504 mmol), prop-2-en-1-amine (0.5 ml), ACN (3 ml). MS m/z (rel. intensity, 70 eV) 281 (M+, 6), 131 (8), 77 (6), 71 (5), 70 (bp).

Example 81

4-{[7-(METHYLSULFONYL)-3,4-DIHYDRO-2H-CHROMEN-2-YL]METHYL}MORPHOLINE

Preparation according to Example 25: [7-(methylsulfonyl)-3,4-dihydro-2H-chromen-2-yl]methyl 4-methylbenzenesulfonate (0.020 g, 0.0504 mmol), morpholine (0.5 ml), ACN (3 ml). MS m/z (rel. intensity, 70 eV) 311 (M+, 2), 132 (3), 131 (5), 101 (6), 100 (bp), 56 (6).

Example 82

N-{[7-(METHYLSULFONYL)-3,4-DIHYDRO-2H-CHROMEN-2-YL]METHYL}BUTAN-1-AMINE

Preparation according to Example 25: [7-(methylsulfonyl)-3,4-dihydro-2H-chromen-2-yl]methyl 4-methylbenzenesulfonate (0.020 g, 0.0504 mmol), butan-1-amine (0.5 ml), ACN (3 ml). MS m/z (rel. intensity, 70 eV) 297 (M+, 6), 254 (9), 131 (8), 87 (7), 86 (bp), 77 (7).

Example 83

N-{[7-(METHYLSULFONYL)-3,4-DIHYDRO-2H-CHROMEN-2-YL]METHYL}-N-PROPYLPROPAN-1-AMINE

Preparation according to Example 25: [7-(methylsulfonyl)-3,4-dihydro-2H-chromen-2-yl]methyl 4-methylbenzenesulfonate (0.020 g, 0.0504 mmol), N-propylpropan-1-amine (0.5 ml), ACN (3 ml). MS m/z (rel. intensity, 70 eV) 325 (M+, 1), 296 (7), 131 (4), 115 (10), 114 (bp), 86 (6).

Example 84

N,N-DIMETHYL-1-[7-(METHYLSULFONYL)-3,4-DIHYDRO-2H-CHROMEN-2-YL]METHANAMINE

Preparation according to Example 25: [7-(methylsulfonyl)-3,4-dihydro-2H-chromen-2-yl]methyl 4-methylbenzenesulfonate (0.020 g, 0.0504 mmol), N-methylmethanamine (2.0 M in MeOH, 0.5 ml), ACN (3 ml). MS m/z (rel. intensity, 70 eV) 269 (M+, 2), 131 (4), 77 (4), 63 (2), 59 (4), 58 (bp).

Example 85

N-ETHYL-N-{[7-(METHYLSULFONYL)-3,4-DIHYDRO-2H-CHROMEN-2-YL]METHYL}ETHANAMINE

Preparation according to Example 25: [7-(methylsulfonyl)-3,4-dihydro-2H-chromen-2-yl]methyl 4-methylbenzenesulfonate (0.020 g, 0.0504 mmol), N-ethylethanamine (0.5 ml), ACN (3 ml). MS m/z (rel. intensity, 70 eV) 297 (M+, 1), 131 (4), 87 (6), 86 (bp), 58 (5), 56 (3).

Example 86

N-{[7-(METHYLSULFONYL)-3,4-DIHYDRO-2H-CHROMEN-2-YL]METHYL}PROPAN-2-AMINE

Preparation according to Example 25: [7-(methylsulfonyl)-3,4-dihydro-2H-chromen-2-yl]methyl 4-methylbenzenesulfonate (0.020 g, 0.0504 mmol), propan-2-amine (0.5 ml), ACN (3 ml). MS m/z (rel. intensity, 70 eV) 283 (M+, 6), 268 (8), 77 (7), 72 (bp), 56 (6).

Example 87

N-METHYL-N-{[7-(METHYLSULFONYL)-3,4-DIHYDRO-2H-CHROMEN-2-YL]METHYL}PROPAN-1-AMINE

Preparation according to Example 25: [7-(methylsulfonyl)-3,4-dihydro-2H-chromen-2-yl]methyl 4-methylbenzenesulfonate (0.020 g, 0.0504 mmol), N-methylpropan-1-amine (N—,N—) (0.5 ml), ACN (3 ml). MS m/z (rel. intensity, 70 eV) 297 (M+, 2), 131 (5), 87 (6), 86 (bp), 77 (5), 58 (7).

Example 88

N-ETHYL-N-{[7-(METHYLSULFONYL)-3,4-DIHYDRO-2H-CHROMEN-2-YL]METHYL}PROPAN-1-AMINE

Preparation according to Example 25: [7-(methylsulfonyl)-3,4-dihydro-2H-chromen-2-yl]methyl 4-methylbenzenesulfonate (0.020 g, 0.0504 mmol), N-ethylpropan-1-amine (0.5 ml), ACN (3 ml). MS m/z (rel. intensity, 70 eV) 311 (M+, 1), 282 (5), 101 (8), 100 (bp), 72 (6), 58 (9).

Example 89

2-({[7-(METHYLSULFONYL)-3,4-DIHYDRO-2H-CHROMEN-2-YL]METHYL}AMINO)ETHANOL

Preparation according to Example 25: [7-(methylsulfonyl)-3,4-dihydro-2H-chromen-2-yl]methyl 4-methylbenzenesulfonate (0.020 g, 0.0504 mmol), 2-aminoethanol (0.5 ml), ACN (3 ml). $^1$H-NMR (400 MHz, CDCl$_3$): δ 7.37-7.39 (2H, m), δ 7.23 (1H, d, J=8 Hz), δ 4.18-4.24 (1H, m), δ 3.63-3.72 (2H), δ 3.02 (3H, s), δ 2.81-3.00 (6H, m), δ 1.97-2.08 (1H, m), δ 1.83-1.87 (1H, m).

Example 90

N-METHYL-N-{[7-(METHYLSULFONYL)-3,4-DIHYDRO-2H-CHROMEN-2-YL]METHYL}ETHANAMINE

Preparation according to Example 25: [7-(methylsulfonyl)-3,4-dihydro-2H-chromen-2-yl]methyl 4-methylbenzenesulfonate (0.020 g, 0.0504 mmol), N-methylethanamine (0.5 ml), ACN (3 ml). MS m/z (rel. intensity, 70 eV) 283 (M+, 2), 131 (4), 77 (4), 73 (5), 72 (bp), 63 (2).

Example 91

2-METHOXY-N-{[7-(METHYLSULFONYL)-3,4-DIHYDRO-2H-CHROMEN-2-YL]METHYL}ETHANAMINE

Preparation according to Example 25: [7-(methylsulfonyl)-3,4-dihydro-2H-chromen-2-yl]methyl 4-methylbenzenesulfonate (0.020 g, 0.0504 mmol), 2-methoxyethanamine (0.5 ml), ACN (3 ml). MS m/z (rel. intensity, 70 eV) 299 (M+, 6), 254 (38), 131 (8), 88 (bp), 58 (8), 56 (12).

Example 92

1-{[7-(METHYLSULFONYL)-3,4-DIHYDRO-2H-CHROMEN-2-YL]METHYL}AZETIDINE

Preparation according to Example 25: [7-(methylsulfonyl)-3,4-dihydro-2H-chromen-2-yl]methyl 4-methylbenzenesulfonate (0.020 g, 0.0504 mmol), azetidine (0.2 ml), ACN (3 ml). MS m/z (rel. intensity, 70 eV) 281 (M+, 3), 131 (6), 77 (5), 71 (5), 70 (bp).

Example 93

2-METHYL-N-{[7-(METHYLSULFONYL)-3,4-DIHYDRO-2H-CHROMEN-2-YL]METHYL}PROPAN-1-AMINE

Preparation according to Example 25: [7-(methylsulfonyl)-3,4-dihydro-2H-chromen-2-yl]methyl 4-methylbenzenesulfonate (0.020 g, 0.0504 mmol), 2-methylpropan-1-amine (0.5 ml), ACN (3 ml). MS m/z (rel. intensity, 70 eV) 297 (M+, 6), 254 (33), 130 (7), 87 (7), 86 (bp), 57 (9).

Example 94

1-{[7-(METHYLSULFONYL)-3,4-DIHYDRO-2H-CHROMEN-2-YL]METHYL}PYRROLIDINE

Preparation according to Example 25: [7-(methylsulfonyl)-3,4-dihydro-2H-chromen-2-yl]methyl 4-methylbenzenesulfonate (0.020 g, 0.0504 mmol), pyrrolidine (0.5 ml), ACN (3 ml). MS m/z (rel. intensity, 70 eV) 295 (M+, 2), 131 (4), 85 (6), 84 (bp), 77 (3), 55 (4).

Example 95

1-{[7-(METHYLSULFONYL)-3,4-DIHYDRO-2H-CHROMEN-2-YL]METHYL}PIPERIDINE

Preparation according to Example 25: [7-(methylsulfonyl)-3,4-dihydro-2H-chromen-2-yl]methyl 4-methylbenzenesulfonate (0.020 g, 0.0504 mmol), piperidine (0.5 ml), ACN (3 ml). MS m/z (rel. intensity, 70 eV) 309 (M+, 1), 131 (4), 99 (7), 98 (bp), 77 (3), 55 (5).

Example 96

3-FLUORO-N-{[7-(METHYLSULFONYL)-3,4-DIHYDRO-2H-CHROMEN-2-YL]METHYL}PROPAN-1-AMINE 3-fluoropropan-1-amine HCl-salt (0.178 g, 1.52 mmol) was basified on a SCX-3 ion exchange column (TEA/MeOH). [7-(methylsulfonyl)-3,4-dihydro-2H-chromen-2-yl]methyl 4-methylbenzenesulfonate (0.020 g, 0.0561 mmol) and 3-fluoropropan-1-amine (0.15 M in MeOH/TEA:4/1, 5 ml) was heated under microwave radiation at 120° C. for 1 h 20 min. MS m/z (rel. intensity, 70 eV) 301 (M+, 3), 131 (8), 91 (9), 90 (bp), 86 (18), 70 (18).

Example 97

4-{[(S)-5-FLUORO-7-(METHYLSULFONYL)-2,3-DIHYDRO-1,4-BENZODIOXIN-2-YL]METHYL}MORPHOLINE

A mixture of [(2R)-5-fluoro-7-(methylsulfonyl)-2,3-dihydro-1,4-benzodioxin-2-yl]methyl 4-methylbenzenesulfonate (0.39 g, 0.95 mmol), morpholine (0.3 ml, 3.4 mmol) and ACN (3 ml) was heated under microwave radiation at 120° C. for 70 min. Purification on SCX-3 column (TEA/MeOH) and by flash column chromatography and (isooctane/EtOAc/MeOH). Yield: 0.17 g. The amine was converted to the hydrochloric acid salt and crystallized from MeOH/Et$_2$O. M.p. 251° C. MS m/z (rel. intensity, 70 eV) 331 (M+, 1), 207 (2), 101 (6), 100 (bp), 69 (2), 56 (5).

Example 98

N-({(2S)-7-[(TRIFLUOROMETHYL)SULFONYL]-2,3-DIHYDRO-1,4-BENZODIOXIN-2-YL}METHYL)PROPAN-2-AMINE

A mixture of {(2R)-7-[(trifluoromethyl)sulfonyl]-2,3-dihydro-1,4-benzodioxin-2-yl}methyl) 4-methylbenzenesulfonate (0.45 g, 1.0 mmol), propan-2-amine (1 ml) and ACN (2 ml) was heated under microwave radiation at 120° C. for 20 min. The reaction mixture was purified on a SCX-3 cation exchange column (MeOH/TEA) and by flash chromatography (isooctane/EtOAc/MeOH). Yield: 0.150 g, 44%. The amine was converted to the hydrochloric acid salt and crystallized from ACN. M.p. 196.2-196.5° C. ESI MS m/z (rel. intensity) 340 (M+1, bp), 341 (16), 381 (14), 102 (8), 342 (6). [α]=−62° (MeOH).

PREPARATIONS

Preparation 1

5-BROMO-2-(OXIRAN-2-YLMETHOXY)BENZALDEHYDE

A mixture of 5-bromo-2-hydroxybenzaldehyde (10 g, 50 mmol), epibromohydrin (13.6 g, 100 mmol) and $K_2CO_3$ (10.3 g, 75 mmol) in DMF (50 ml) was heated at 60° C. for 2 h. The mixture was cooled to ambient temperature and water and EtOAc was added. The phases were separated and the combined organic phases were washed with brine, dried ($Na_2SO_4$), filtered and concentrated. The residue was purified by flash column chromatography (isooctane/EtOAc) to give the title compound (12.3 g). MS m/z (rel. intensity, 70 eV) 256 (M+, 41), 201 (77), 200 (bp), 199 (84), 63 (60).

Preparation 2

5-BROMO-2-(OXIRAN-2-YLMETHOXY)PHENYL FORMATE

To a solution of 5-bromo-2-(oxiran-2-ylmethoxy)benzaldehyde (12.3 g, 47.7 mmol) in DCM (50 ml) was added m-CPBA (12.8 g, 57.2 mmol). The solution was heated at reflux for 3 h and 30 min and then brought to ambient temperature. Aqueous sodium bicarbonate (saturated) and DCM was added and the phases were separated. The organic phase was washed with brine, dried ($Na_2SO_4$), filtered and evaporated to dryness to give the crude title compound. Crude yield: 12.3 g. MS m/z (rel. intensity, 70 eV) 272 (M+, 7), 244 (50), 189 (95), 188 (bp), 57 (93).

Preparation 3

(7-BROMO-2,3-DIHYDRO-1,4-BENZODIOXIN-2-YL)METHANOL 5-bromo-2-(oxiran-2-ylmethoxy)phenyl formate (12.6 g, 46.0 mmol) was dissolved in dioxane (50 ml) and KOH (10%)/NaOH (20%) was added. Water and EtOAc was added and the phases were separated. The combined organic phases were washed with brine and dried to give the title compound (10.3 g). MS m/z (rel. intensity, 70 eV) 245 (M+, 96) 244 (M+, bp), 213 (29), 189 (46), 188 (49).

Preparation 4

[7-(METHYLSULFONYL)-2,3-DIHYDRO-1,4-BENZODIOXIN-2-YL]METHANOL 4 batches of a mixture of (7-bromo-2,3-dihydro-1,4-benzodioxin-2-yl)methanol (0.5 g, 2.0 mmol), sodium methanesulfinate (85%) (0.37 g, 3.1 mmol), CuI (0.039 g, 0.2 mmol), L-proline (0.047 g, 0.4 mmol) and $K_2CO_3$ (0.056 g, 0.4 mmol) in DMSO (4 ml) was heated under microwave radiation to 140° C. for 1 h in a nitrogen-flushed vial. The batches were mixed and diluted with water and HCl (1 N). The resulting solution was extracted with EtOAc. The combined organic phases were washed with brine, dried and purified on flash column chromatography (isooctane/EtOAc/MeOH) to give the title compound (0.89 g). MS m/z (rel. intensity, 70 eV) 244 (M+, bp), 213 (40), 165 (27), 134 (22), 79 (18).

Preparation 5

[7-(METHYLSULFONYL)-2,3-DIHYDRO-1,4-BENZODIOXIN-2-YL]METHYL 4-METHYL-BENZENESULFONATE

A mixture of [7-(methylsulfonyl)-2,3-dihydro-1,4-benzodioxin-2-yl]methanol (0.9 g, 3.7 mmol), p-toluenesulfonyl chloride (1.0 g, 5.5 mmol), TEA (0.76 ml, 5.5 mmol) and 4-DMAP (0.4 g, 3.7 mmol) in DCM (20 ml) was stirred at room temperature for 1 h and 30 min. The solution was diluted with DCM and washed with HCl (1 N), water and brine. The organic phase was dried and concentrated to give the title compound (1.1 g). MS m/z (rel. intensity, 70 eV) 398 (M+, 51), 226 (bp), 225 (23), 213 (30), 91 (62).

Preparation 6

5-BROMO-2-[(2S)-OXIRAN-2-YLMETHOXY]BENZALDEHYDE

Preparation according to Preparation 1 using 5-bromo-2-hydroxybenzaldehyde (6 g, 30 mmol), (S)-glycidyltosylate (8.2 g, 36 mmol), $K_2CO_3$ (4.9 g, 36 mmol) and DMF (12 ml). Water (100 ml) was added and the solution was extracted with EtOAc (3×100 ml). The combined organic phases were washed with LiCl (5%, 100 ml), HCl (1 N, 100 ml), brine, were dried and concentrated to give the crude title compound (8.3 g). MS m/z (rel. intensity, 70 eV) 257 (M+, 38), 256 (M+, 39), 200 (bp), 199 (87), 57 (88).

Preparation 7

5-BROMO-2-[(2S)-OXIRAN-2-YLMETHOXY]PHENYL FORMATE

Preparation according to Preparation 2 using 5-bromo-2-[(2S)-oxiran-2-ylmethoxy]benzaldehyde (8.3 g, 32 mmol), DCM (100 ml) and m-CPBA (77%, 10.9 g, 48.6 mmol). The mixture was heated at reflux for 3 h. Crude yield: 8.5 g. MS m/z (rel. intensity, 70 eV) 274 (M+, 10), 273 (M+, 9), 189 (98), 188 (bp), 57 (77).

Preparation 8

[(2R)-7-BROMO-2,3-DIHYDRO-1,4-BENZODIOXIN-2-YL]METHANOL 5-bromo-2-[(2S)-oxiran-2-ylmethoxy]phenyl formate (8.5 g, 31 mmol) was dissolved in dioxane. At 0° C., KOH (10%) was added. The mixture was stirred in rt for 1 h and 30 min and was then concentrated. Water was added. Aqueous HCl (1 N) was added to neutralize and the solution was then extracted with EtOAc (3×75 ml). The combined organic phases were washed with brine, dried ($Na_2SO_4$) and evaporated to dryness. Purification on flash column chromatography (isooctane/EtOAc) gave the crude title compound (4.4 g). MS m/z (rel. intensity, 70 eV) 245 (M+, 97) 244 (M+, bp), 189 (48), 188 (50) 70 (39).

Preparation 9

[[(2R)-7-(METHYLSULFONYL)-2,3-DIHYDRO-1,4-BENZODIOXIN-2-YL]METHANOL

Two batches of [(2R)-7-bromo-2,3-dihydro-1,4-benzodioxin-2-yl]methanol (2.2 g, 8.9 mmol), sodium methanesulfinate (85%) (1.6 g, 13.3 mmol), CuI (0.2 g, 0.9 mmol), L-proline (0.2 g, 1.8 mmol) and $K_2CO_3$ (0.2 g, 1.8 mmol) in DMSO (20 ml) were heated under microwave radiation at 140° C. for 3 h in nitrogen-flushed vials. Water and EtOAc were added. The water layer was extracted with EtOAc (3×100 ml) and the combined organic phases were washed with LiCl (5%), HCl (1 N) and brine. The resulting solution was dried ($Na_2SO_4$) and evaporated to dryness. The residue was purified by flash column chromatography (isooctane/EtOAc) to give the title compound (1.7 g). MS m/z (rel. intensity, 70 eV) 244 (M+, bp), 213 (39), 165 (26), 134 (22), 79 (23).

Preparation 10

[(2S)-7-(METHYLSULFONYL)-2,3-DIHYDRO-1,4-BENZODIOXIN-2-YL]METHYL 4-METHYL-BENZENESULFONATE

Preparation according to Preparation 5 using [[(2R)-7-(methylsulfonyl)-2,3-dihydro-1,4-benzodioxin-2-yl]methanol (2.1 g, 8.6 mmol), p-toluenesulfonyl chloride (2.5 g, 12.8 mmol), TEA (1.8 ml, 12.8 mmol) and 4-DMAP (1.0 g, 8.6 mmol) and DCM (dry, 20 ml). DCM (50 ml) was added and the solution was washed with HCl (100 ml, 1 N), water (100 ml) and brine (100 ml) and was evaporated to dryness to give the title compound (3.0 g). MS m/z (rel. intensity, 70 eV) 398 (M+, 49), 226 (bp), 225 (24), 213 (30), 91 (68).

Preparation 11

5-BROMO-2-[(2R)-OXIRAN-2-YLMETHOXY]BENZALDEHYDE

Preparation according to Preparation 1 using 5-bromo-2-hydroxybenzaldehyde (6 g, 29 mmol), (R)-glycidyltosylate (6.7 g, 29 mmol), $K_2CO_3$ (4.9 g, 35 mmol) and DMF (12 ml). The combined organic phases were washed with LiCl (5%, 100 ml), HCl (1 N, 100 ml), brine (100 ml) and were evaporated to dryness. The residue was purified by flash column chromatography (isooctane/EtOAc) to give the crude title compound (6.8 g). MS m/z (rel. intensity, 70 eV) 257 (M+, 38), 256 (M+, 39), 200 (bp), 199 (87), 57 (88).

Preparation 12

5-BROMO-2-[(2R)-OXIRAN-2-YLMETHOXY]PHENYL FORMATE

Preparation according to Preparation 2 using 5-bromo-2-[(2R)-oxiran-2-ylmethoxy]benzaldehyde (6.8 g, 26 mmol), DCM (75 ml) and m-CPBA (77%, 8.9 g, 39.5 mmol). Crude yield: 7.0 g. MS m/z (rel. intensity, 70 eV) 274 (M+, 10), 273 (M+, 9), 189 (98), 188 (bp), 57 (77).

Preparation 13

[(2S)-7-BROMO-2,3-DIHYDRO-1,4-BENZODIOXIN-2-YL]METHANOL

Preparation according to Preparation 8 using 5-bromo-2-[(2R)-oxiran-2-ylmethoxy]phenyl formate (7.0 g, 25 mmol), dioxane (30 ml) and KOH (10%, 15 ml), stirred for 1 h. Purification on flash column chromatography (Isooctane/EtOAc). Crude yield: 3.7 g. MS m/z (rel. intensity, 70 eV) 245 (M+, 97) 244 (M+, bp), 189 (48), 188 (50) 79 (39).

Preparation 14

[[(2S)-7-(METHYLSULFONYL)-2,3-DIHYDRO-1,4-BENZODIOXIN-2-YL]METHANOL

A mixture of [(2S)-7-bromo-2,3-dihydro-1,4-benzodioxin-2-yl]methanol (0.6 g, 2.3 mmol), sodium methanesulfinate (85%) (0.4 g, 3.4 mmol), CuI (0.043 g, 0.2 mmol), L-proline (0.052 g, 0.5 mmol) and NaOH (0.018 g, 0.5 mmol) in DMSO (3 ml) was heated under microwave radiation at 140° C. for 2 h 30 min in a nitrogen-flushed vial. The mixture was mixed with 2 other batches and water and EtOAc was added. The solution was extracted with EtOAc (3×50 ml). The combined organic phases were washed with LiCl (5%), HCl (1 N) and brine. The resulting solution was dried ($Na_2SO_4$) and evaporated to dryness. Purification on flash column chromatography (isooctane/EtOAc) gave the title compound (1.2 g). MS m/z (rel. intensity, 70 eV) 244 (M+, bp), 213 (39), 165 (26), 134 (22), 79 (23).

Preparation 15

[(2R)-7-(METHYLSULFONYL)-2,3-DIHYDRO-1,4-BENZODIOXIN-2-YL]METHYL 4-METHYL-BENZENESULFONATE

Preparation according to Preparation 10 using [[(2S)-7-(methylsulfonyl)-2,3-dihydro-1,4-benzodioxin-2-yl]methanol (1.2 g, 5.0 mmol), DCM (25 ml), p-toluenesulfonyl chloride (1.4 g, 7.5 mmol), TEA (1.0 ml, 12.8 mmol) and 4-DMAP (0.6 g, 5.0 mmol). Yield: 1.8 g. MS m/z (rel. intensity, 70 eV) 398 (M+, 49), 226 (bp), 225 (24), 213 (30), 91 (68).

Preparation 16

4-BROMO-2-FLUOROPHENYL ACETATE

A mixture of 4-bromo-2-fluorophenol (5 g, 30 mmol) and acetic anhydride (13.4 g, 130 mmol) in pyridine (10.6 ml, 130 mmol) was heated at 100° C. for 3 h and then brought to ambient temperature and poured into water. HCl (1 N and 6 N) was added and the solution was extracted with EtOAc. The combined organic phases were washed with sodium bicarbonate (saturated, 3×50 ml), dried ($Na_2SO_4$) and evaporated to dryness to give the title compound (5.8 g). MS m/z (rel. intensity, 70 eV) 233 (M+, 11), 232 (M+, 12), 191 (95), 190 (bp), 161 (8).

Preparation 17

1-(5-BROMO-3-FLUORO-2-HYDROXYPHENYL)ETHANONE $AlCl_3$ (5.0 g, 38 mmol) was added in portions to 4-bromo-2-fluorophenyl acetate (5.8 g, 25 mmol). The mixture was heated at 150° C. for 3 h and then brought to ambient temperature. Water (ice-cold) was slowly added and then EtOAc. The resulting mixture was vigorously stirred and then the phases were separated and the water phase extracted with EtOAc. The combined organic phases were washed with brine, dried ($Na_2SO_4$) and evaporated to dryness to give the title compound (5.3 g). MS m/z (rel. intensity, 70 eV) 233 (M+, 55), 232 (M+, 56), 218 (98), 217 (bp), 161 (10).

Preparation 18

1-[5-BROMO-3-FLUORO-2-(OXIRAN-2-YL-METHOXY)PHENYL]ETHANONE

A mixture of 1-(5-bromo-3-fluoro-2-hydroxyphenyl)ethanone (3.7 g, 15.8 mmol), epibromohydrin (2.6 ml, 31.7 mmol) and $K_2CO_3$ (3.3 g, 23.8 mmol) in DMF (20 ml) was heated at 60° C. for 1 h 50 min. The solution was brought to ambient temperature and water and EtOAc was added. The water phase was extracted with EtOAc. The combined organic phases were washed with LiCl (5%), HCl (1 N) and brine and were dried ($Na_2SO_4$) and evaporated to dryness. Purification on flash column chromatography (isooctane/EtOAc) gave the title compound (3.9 g). MS m/z (rel. intensity, 70 eV) 289 (M+, 13), 288 (M+, 14), 218 (91), 217 (bp), 81 (39), 57 (95).

Preparation 19

5-BROMO-3-FLUORO-2-(OXIRAN-2-YLMETHOXY)PHENYL ACETATE

A solution of 1-[5-bromo-3-fluoro-2-(oxiran-2-ylmethoxy)phenyl]ethanone (1.3 g, 4.5 mmol) and m-CPBA (4.0 g, 18 mmol) in DCM (25 ml) was heated at reflux. After 22 h more m-CPBA (2.7 g, 12 mmol) was added and the mixture was heated at reflux for another 22 h and then brought to ambient temperature. The solid was filtered off and rinsed. The resulting filtrate was washed with sodium bicarbonate (saturated), brine and further dried ($Na_2SO_4$) and evaporated to dryness to give the crude title compound (2.6 g). MS m/z (rel. intensity, 70 eV) 305 (M+, 5), 304 (M+, 6), 263 (97), 262 (bp), 206 (49), 57 (65).

Preparation 20

(7-BROMO-5-FLUORO-2,3-DIHYDRO-1,4-BENZODIOXIN-2-YL)METHANOL 5-bromo-3-fluoro-2-(oxiran-2-ylmethoxy)phenyl acetate (2.6 g, 8.7 mmol) was stirred in dioxane at RT. Aqueous KOH (10%) was added until basic pH was reached (1:1 water/KOH (10%)). Water was added and the solution was extracted with EtOAc. The combined organic phases were washed with brine, dried and evaporated to dryness to give the title compound (0.8 g). MS m/z (rel. intensity, 70 eV) 263 (M+, 97), 262 (M+, bp), 218 (39), 207 (50), 206 (51).

Preparation 21

[5-FLUORO-7-(METHYLSULFONYL)-2,3-DIHYDRO-1,4-BENZODIOXIN-2-YL]METHANOL

A mixture of (7-bromo-5-fluoro-2,3-dihydro-1,4-benzodioxin-2-yl)methanol (0.6 g, 2.3 mmol), sodium methanesulfinate (85%) (0.4 g, 3.5 mmol), CuI (0.04 g, 0.2 mmol), L-proline (0.05 g, 0.5 mmol) and $K_2CO_3$ (0.06 g, 0.5 mmol) in DMSO (6 ml) was heated in two batches under microwave radiation at 140° C. for 2 h in nitrogen-flushed vials. After cooling to ambient temperature, the batches were mixed, water and EtOAc were added and the water phase was extracted with EtOAc. The combined organic phases were washed with LiCl (5%), HCl (1 N), brine, dried ($Na_2SO_4$) and evaporated to dryness. The product was mixed with another batch of the same compound. Purification on flash column chromatography (isooctane/EtOAc/MeOH) gave the title compound (0.2 g). MS m/z (rel. intensity, 70 eV) 262 (M+, bp), 231 (32), 206 (12), 183 (17), 152 (14).

Preparation 22

[5-FLUORO-7-(METHYLSULFONYL)-2,3-DIHYDRO-1,4-BENZODIOXIN-2-YL]METHYL 4-METHYLBENZENESULFONATE

A solution of [5-fluoro-7-(methylsulfonyl)-2,3-dihydro-1,4-benzodioxin-2-yl]methanol (0.4 g, 1.7 mmol), toluenesulfonyl chloride (0.5 g, 2.6 mmol), TEA (0.4 ml, 2.6 mmol) and 4-DMAP (0.2 g, 1.7 mmol) in DCM (10 ml) was stirred at rt for 1 h. DCM was added and the resulting mixture was washed with HCl (1 N) and brine. The organic phase was dried ($Na_2SO_4$) and evaporated to dryness to give the title compound (0.7 g). MS m/z (rel. intensity, 70 eV) 416 (M+, 31), 244 (bp), 243 (26), 231 (19), 91 (70).

Preparation 23

1-(5-BROMO-3-FLUORO-2-[(2R)-OXIRAN-2-YLMETHOXY]PHENYL) ETHANONE

Preparation according to Preparation 1 using 1-(5-bromo-3-fluoro-2-hydroxyphenyl)ethanone (16.8 g, 72 mmol), (R)-glycidyltosylate (18.1 g, 79 mmol), $K_2CO_3$ (15.0 g, 108 mmol) and DMF (60 ml). The combined organic phases were washed with LiCl (5%), HCl (1 N). Flash column chromatography (isooctane/EtOAc) yielded the title compound (8.3 g). MS m/z (rel. intensity, 70 eV) 290 (M+, 9), 288 (M+, 9), 217 (bp), 81 (47), 57 (46).

Preparation 24

5-BROMO-3-FLUORO-2-[(2R)-OXIRAN-2-YLMETHOXY]PHENYL ACETATE

Preparation according to Preparation 7 using 1-(5-bromo-3-fluoro-2-[(2R)-oxiran-2-ylmethoxyphenyl)ethanone (19.5 g, 67 mmol), $CHCl_3$ and m-CPBA (77%, 60.5 g, 27 mmol). The mixture was heated at reflux for 24 h. The crude product was further used (Preparation 25). MS m/z (rel. intensity, 70 eV) 306 (M+, 4), 304 (M+, 4) 262 (bp), 69 (69), 57 (99).

Preparation 25

[(2S)-7-BROMO-5-FLUORO-2,3-DIHYDRO-1,4-BENZODIOXIN-2-YL]METHANOL 1-(5-bromo-3-fluoro-2-[(2R)-oxiran-2-ylmethoxy]phenyl acetate (crude, max 67 mmol) was stirred in dioxane at 0° C. NaOH (15%) was added until the mixture reached pH 14. The mixture was stirred for 30 min at RT and then concentrated. Water was added and the mixture extracted with EtOAc. The combined organic phases were washed with brine, dried ($Na_2SO_4$) and evaporated to dryness to give the crude title compound. Yield: 10.3 g. MS m/z (rel. intensity, 70 eV) 262 (M+, bp), 264 (M+, bp), 206 (70), 81 (58), 69 (55), 57 (53).

Preparation 26

[(2S)-5-FLUORO-7-(METHYLSULFONYL)-2,3-DIHYDRO-1,4-BENZODIOXIN-2-YL]METHANOL

Preparation according to Preparation 21 using [(2S)-7-bromo-5-fluoro-2,3-dihydro-1,4-benzodioxin-2-yl]methanol (2.35 g, 8.9 mmol), sodium methanesulfinate (85%) (1.29 g, 107 mmol), CuI (0.34 g, 1.8 mmol), L-proline (0.41 g, 3.6 mmol) and NaOH (0.071 g, 1.8 mmol) in DMSO (6 ml). Yield 0.98 g. MS m/z (rel. intensity, 70 eV) 262 (M+, bp), 231 (35), 183 (22), 152 (23), 57 (30).

Preparation 27

[(2R)-5-FLUORO-7-(METHYLSULFONYL)-2,3-DIHYDRO-1,4-BENZODIOXIN-2-YL]METHYL 4-METHYLBENZENESULFONATE

Preparation according to Preparation 10 using [[(2S)-5-fluoro-7-(methylsulfonyl)-2,3-dihydro-1,4-benzodioxin-2-yl]methanol (0.97 g, 3.7 mmol), DCM (20 ml), p-toluenesulfonyl chloride (1.06 g, 5.6 mmol), TEA (0.78 ml, 5.6 mmol) and 4-DMAP (0.46 g, 3.7 mmol). Yield: 1.47 g. MS m/z (rel. intensity, 70 eV) 416 (M+, 40), 244 (bp), 243 (26), 231 (19), 91 (50).

Preparation 28

4-[(TRIFLUOROMETHYL)SULFONYL]PHENOL

A mixture of 4-[(trifluoromethyl)thio]phenol (4.5 g, 23.2 mmol), $Na_2WO_4 \cdot 2H_2O$ (0.08 g, 0.24 mmol) and hydrogen peroxide (6 ml, 59 mmol) in acetic acid (25 ml) was heated at 65° C. for overnight. $Na_2S_2O_5$ (sat.) and NaOH (20%) was added (until pH 8) and the solution was extracted with EtOAc. The combined organic phases were dried ($Na_2SO_4$) and evaporated to dryness to give the crude title compound (6.0 g). MS m/z (rel. intensity, 70 eV) 226 (M+, 18), 157 (bp), 109 (14), 93 (52), 65 (53).

Preparation 29

4-[(TRIFLUOROMETHYL)SULFONYL]PHENYL ACETATE

Preparation according to Preparation 16 using 4-[(trifluoromethyl)sulfonyl]phenol (4.5 g, 23.2 mmol), acetic anhydride (13.4 g, 130 mmol) and pyridine (10.6 ml, 130 mmol). Crude yield: 6.8 g. MS m/z (rel. intensity, 70 eV) 268 (M+, 6), 157 (bp), 93 (84), 65 (52), 64 (43).

Preparation 30

1-{2-HYDROXY-5-[(TRIFLUOROMETHYL)SULFONYL]PHENYL}ETHANONE

Preparation according to Preparation 17 using $AlCl_3$ (4.66 g, 35 mmol) and 4-[(trifluoromethyl)sulfonyl]phenyl acetate (6.8 g, 23.2 mmol). Yield 3.2 g. MS m/z (rel. intensity, 70 eV) 268 (M+, 37), 253 (32), 199 (bp), 120 (29), 107 (22).

Preparation 31

1-{2-[(2R)-OXIRAN-2-YLMETHOXY]-5-[(TRIFLUOROMETHYL)SULFONYL]PHENYL}ETHANONE

Preparation according to Preparation 23 using 1-{2-hydroxy-5-[(trifluoromethyl)sulfonyl]phenyl}ethanone (3.2 g, 11.9 mmol), (R)-glycidyltosylate (3.2 g, 14 mmol), $K_2CO_3$ (2.0 g, 14.3 mmol) and DMF (30 ml). Yield 2.2 g. MS m/z (rel. intensity, 70 eV) 324 (M+, 4), 277 (83), 255 (69), 253(67), 199 (bp).

Preparation 32

2-[(2R)-OXIRAN-2-YLMETHOXY]-5-[(TRIFLUOROMETHYL)SULFONYL]PHENYL ACETATE

Preparation according to Preparation 19 using 1-{2-[(2R)-oxiran-2-ylmethoxy]-5-[(trifluoromethyl)sulfonyl]phenyl}ethanone (1.2 g, 3.7 mmol) and m-CPBA (4.95 g, 22.5 mmol) in $CHCl_3$ (50 ml). Crude yield 1.0 g. MS m/z (rel. intensity, 70 eV) 298 (34), 229 (77), 165 (bp), 107 (39), 79 (30).

Preparation 33

[(2S)-7-(TRIFLUOROMETHYLSULFONYL)-2,3-DIHYDRO-1,4-BENZODIOXIN-2-YL]METHANOL

Preparation according to Preparation 20 using 2-[(2R)-oxiran-2-ylmethoxy]-5-[(trifluoromethyl)sulfonyl]phenyl acetate (1.0 g, 3.7 mmol), dioxane (10 ml) and KOH (10%, 10 ml), the mixture stirred at RT for 1 h. Yield 1.0 g. MS m/z (rel. intensity, 70 eV) 298 (M+, 29), 229 (72), 165 (bp), 107 (67), 79 (33).

Preparation 34

[(2R)-7-(TRIFLUOROMETHYLSULFONYL)-2,3-DIHYDRO-1,4-BENZODIOXIN-2-YL]METHYL 4-METHYLBENZENESULFONATE

Preparation according to Preparation 22 using [7-(trifluoromethylsulfonyl)-2,3-dihydro-1,4-benzodioxin-2-yl]methanol (0.75 g, 2.5 mmol), toluenesulfonyl chloride (0.72 g, 3.8 mmol), TEA (0.42 ml, 3 mmol) and 4-DMAP (0.37 g, 3.0 mmol) in DCM (40 ml), stirred for 18 h. Yield 0.28 g. MS m/z (rel. intensity, 70 eV) 452 (M+, bp), 383 (41), 280 (82), 211 (80), 91 (84).

Preparation 35

2-(BENZYLOXY)-1-CHLORO-3-FLUOROBENZENE

A mixture of 2-chloro-6-fluorophenol (25 g, 170 mmol), acetone (200 ml), $K_2CO_3$ (47.08 g, 340 mmol) and bensylbromide (22.31 ml, 187 mmol) was heated at 65° C. for 16 h. The solution was filtered and evaporated. Water (100 ml) was added, and the solution was extracted with EtOAc. The combined organic phases were dried ($Na_2SO_4$) and evaporated to dryness to give the title compound (32.3 g). MS m/z (rel. intensity, 70 eV) 236 (M+, 2), 117 (4), 92 (8), 91 (bp), 65 (13).

Preparation 36

2-(BENZYLOXY)-3-FLUOROPHENOL

A mixture of 2-(benzyloxy)-1-chloro-3-fluorobenzene (3 g, 12.71 mmol), dioxane (6 ml), KOH (0.78 g, 14 mmol), water (6 ml), Tris(dibenzylideneacetone)dipalladium (0.12 g, 0.13 mmol) and 2-di-tertbutylphosphine-2,4,6-triisopropyl-biphenyl (0.22 g, 0.51 mmol) was flushed with $N_2$ and heated under microwave radiation at 120° C. for 7 min. HCl (1 N) was added and the solution was extracted with EtOAc. The combined organic phases were dried ($Na_2SO_4$) and evaporated to dryness. Flash column chromatography (isooctane/EtOAc) yielded the title compound (1.86 g). MS m/z (rel. intensity, 70 eV) 218 (M+, 4), 92 (8), 91 (bp), 65 (13), 51 (9).

Preparation 37

2-{[2-(BENZYLOXY)-3-FLUOROPHENOXY]METHYL}OXIRANE

Preparation according to Preparation 23 using 2-(benzyloxy)-3-fluorophenol (8.9 g, 40.8 mmol), $K_2CO_3$ (11.3 g, 81.6 mmol) (R)-glycidyltosylate (10.2 g, 44.9 mmol) and DMF (50 ml), stirred at 60° C. for 16 h. Yield 9.15 g. MS m/z (rel. intensity, 70 eV) 274 (M+, 6), 153 (5), 92 (8), 91 (bp), 65 (10).

Preparation 38

2-FLUORO-6-(OXIRAN-2-YLMETHOXY)PHENOL

To a mixture of 2-{[2-(benzyloxy)-3-fluorophenoxy]methyl}oxirane (8 g, 29.2 mmol), ethanol (65 ml) and Pd/C (0.5 g) under $N_2$, triethylsilane (9.3 ml, 58.2 mmol) was added dropwise. The solution was stirred for 16 h at room temperature and filtered through Celite. The solvent was evaporated, $Na_2CO_3$ (10%) was added and the solution was extracted with EtOAc. The combined organic phases were dried ($Na_2SO_4$) and evaporated to dryness. Flash column chromatography (isooctane/EtOAc) yielded the title compound (3.5 g). MS m/z (rel. intensity, 70 eV) 184 (M+, bp), 153 (44), 139 (31), 128 (99), 57 (23).

Preparation 39

[(2S)-8-FLUORO-2,3-DIHYDRO-1,4-BENZODIOXIN-2-YL]METHANOL

Preparation according to Preparation 20 using 2-fluoro-6-(oxiran-2-ylmethoxy)phenol (3.9 g, 21.2 mmol), dioxane (20 ml) and KOH (10%, 10 ml). The mixture stirred at RT for 1.5 h. Yield 3.8 g. MS m/z (rel. intensity, 70 eV) 338 (50), 166 (bp), 165 (42), 139 (24), 91 (51).

Preparation 40

[(2R)-8-FLUORO-2,3-DIHYDRO-1,4-BENZODIOXIN-2-YL]METHYL 4-METHYLBENZENESULFONATE

Preparation according to Preparation 22 using [(2S)-8-fluoro-2,3-dihydro-1,4-benzodioxin-2-yl]methanol (7.05 g, 38.0 mmol), toluenesulfonyl chloride (10.9 g, 57 mmol), TEA (8.0 ml, 57 mmol) and 4-DMAP (4.7 g, 38.0 mmol) in DCM (75 ml), stirred for 1.5 h. Flash column chromatography yielded 11.9 g of the title compound. MS m/z (rel. intensity, 70 eV) 184 (90), 153 (43), 139 (29), 128 (bp), 57 (25).

Preparation 41

N-{[(2S)-8-FLUORO-2,3-DIHYDRO-1,4-BENZODIOXIN-2-YL]METHYL}ETHANAMINE

Preparation according to Example 5 using [(2R)-8-fluoro-2,3-dihydro-1,4-benzodioxin-2-yl]methyl 4-methylbenzenesulfonate (4.0 g, 11.8 mmol), ethanamine (5 ml, 70% in water) and ACN (10 ml). Flash column chromatography (Isooctane/EtOAc/MeOH) yielded 2.0 g of the title compound. MS m/z (rel. intensity, 70 eV) 211 (M+, 17), 70 (10), 59 (4), 58 (bp), 56 (4).

Preparation 42

N-BENZYL-N-{[(2S)-8-FLUORO-2,3-DIHYDRO-1,4-BENZODIOXIN-2-YL]METHYL}ETHANAMINE

A mixture of N-{[(2S)-8-fluoro-2,3-dihydro-1,4-benzodioxin-2-yl]methyl}ethanamine (1.95 g, 9.2 mmol), $K_2CO_3$ (2.55 g, 18.5 mmol), benzylbromide (1.3 ml, 11.1 mmol), a spatula of NaI (<5 mg) and acetonitrile was heated under microwave radiation at 120° C. for 20 min. The solution was filtered and evaporated, $Na_2CO_3$ (10%) was added and the solution was extracted with EtOAc. The combined organic phases were dried ($Na_2SO_4$) and evaporated to dryness. Purification on flash column chromatography (isooctane/EtOAc) yielded 2.3 g of the title compound. MS m/z (rel. intensity, 70 eV) 149 (10), 148 (86), 92 (8), 91 (bp), 65 (7).

Preparation 43

N-BENZYL-N-{[(2S)-8-FLUORO-7-(METHYLTHIO)-2,3-DIHYDRO-1,4-BENZODIOXIN-2-YL]METHYL}ETHANAMINE

A mixture of N-benzyl-N-{[(2S)-8-fluoro-2,3-dihydro-1,4-benzodioxin-2-yl]methyl}ethanamine (2.2 g, 7.3 mmol) and 2,2-tetramethylpiperidine (2.5 ml, 14.6 mmol) was added dropwise to n-BuLi (10 ml, 25 mmol) in THF (dry, 10 ml) under $N_2$ at −75° C., followed by the addition of dimethylsulfide (1.32 ml, 14.6 mmol) in THF (dry, 10 ml). The mixture was stirred for 30 min at −75° C., and was then warmed to room temperature. $NH_4Cl$ (sat.) was added and the solution was extracted with EtOAc. The combined organic phases were washed with $Na_2SO_3$ (15%), brine, dried ($Na_2SO_4$) and evaporated to dryness. Flash column chromatography (isooctane/EtOAc) yielded the title compound (1.3 g). MS m/z (rel. intensity, 70 eV) 347 (2), 149 (12), 148 (100), 92 (7), 91 (92).

Preparation 44

N-BENZYL-N-{[(2S)-8-FLUORO-7-(METHYLSULFONYL)-2,3-DIHYDRO-1,4-BENZODIOXIN-2-YL]METHYL}ETHANAMINE

Preparation according to Preparation 28 using N-benzyl-N-{[(2S)-8-fluoro-7-(methylthio)-2,3-dihydro-1,4-benzodioxin-2-yl]methyl}ethanamine (1.2 g, 3.5 mmol), $Na_2WO_4.2H_2O$ (0.01 g, 0.035 mmol) and hydrogen peroxide (0.9 ml, 8.6 mmol) in acetic acid (10 ml) was heated at 50° C. for 2 h. The product was purified by flash column chromatography (isooctane/EtOAc) yielding the title compound (1.0 g). MS m/z (rel. intensity, 70 eV) 149 (11), 148 (bp), 92 (6), 91 (72), 65 (4).

Preparation 45

N-{[(2S)-8-FLUORO-2,3-DIHYDRO-1,4-BENZO-DIOXIN-2-YL]METHYL}-N-PROPAN-1-AMINE

Preparation according to Example 5 using [(2R)-8-fluoro-2,3-dihydro-1,4-benzodioxin-2-yl]methyl 4-methylbenzenesulfonate (4.0 g, 11.8 mmol), ethanamine (5 ml, 70% in water) and ACN (10 ml). Flash column chromatography (isooctane/EtOAc) yielded the title compound (2.35 g). MS m/z (rel. intensity, 70 eV) 225 (M+, 25), 98 (8), 73 (5), 72 (bp), 70 (13).

Preparation 46

N-BENZYL-N-{[(2S)-8-FLUORO-2,3-DIHYDRO-1,4-BENZODIOXIN-2-YL]METHYL}-N-PROPAN-1-AMINE

Preparation according to Preparation 42 using N-{[(2S)-8-fluoro-2,3-dihydro-1,4-benzodioxin-2-yl]methyl}-N-propan-1-amine (2.3 g, 10.2 mmol), $K_2CO_3$ (2.82 g, 18.5 mmol), benzylbromide (1.3 ml, 11.1 mmol), a spatula of NaI and acetonitrile (10 ml). Yield 2.2 g. MS m/z (rel. intensity, 70 eV) 163 (10), 162 (77), 92 (8), 91 (bp), 65 (7).

Preparation 47

N-BENZYL-N-{[(2S)-8-FLUORO-7-(METHYLTHIO)-2,3-DIHYDRO-1,4-BENZODIOXIN-2-YL]METHYL}-N-PROPAN-1-AMINE

Preparation according to Preparation 43 using N-benzyl-N-{[(2S)-8-fluoro-2,3-dihydro-1,4-benzodioxin-2-yl]methyl}-N-propan-1-amine (2.2 g, 7.0 mmol), 2,2-tetramethylpiperidine (3.5 ml, 21 mmol), n-BuLi (9.5 ml, 23.8 mmol), dimethylsulfide (1.25 ml, 14 mmol) and THF (dry, 20 ml). Flash column chromatography (isooctane/EtOAc) yielded the title compound (0.8 g). MS m/z (rel. intensity, 70 eV) 361 (3), 163 (12), 162 (bp), 92 (5), 91 (60).

Preparation 48

N-BENZYL-N-{[(2S)-8-FLUORO-7-(METHYLSULFONYL)-2,3-DIHYDRO-1,4-BENZODIOXIN-2-YL]METHYL}-N-PROPAN-1-AMINE

Preparation according to Preparation 44 using N-benzyl-N-{[(2S)-8-fluoro-7-(methylthio)-2,3-dihydro-1,4-benzodioxin-2-yl]methyl}-N-propan-1-amine (0.78 g, 2.15 mmol), $Na_2WO_4.2H_2O$. (0.007 g, 0.025 mmol), hydrogen peroxide (0.55 ml, 5.5 mmol) and acetic acid (10 ml). Yield 0.36 g. MS m/z (rel. intensity, 70 eV) 163 (13), 162 (bp), 92 (7), 91 (88), 65 (5).

Preparation 49

4-BROMO-2-CHLOROPHENYL ACETATE

Preparation according to Preparation 16 using 4-bromo-2-chlorophenol (6 g, 29 mmol) and acetic anhydride (13.4 g, 130 mmol) in pyridine (10.5 ml, 130 mmol). Yield 7.4 g. MS m/z (rel. intensity, 70 eV) 210 (25), 208 (bp), 206 (79), 63 (21), 62 (9), 250 (M+, 8).

Preparation 50

1-(5-BROMO-3-CHLORO-HYDROXYPHENYL)ETHANONE

Preparation according to Preparation 17 using $AlCl_3$ (4.7 g, 36 mmol) and 4-bromo-2-chlorophenyl acetate (5.9 g, 24 mmol). Yield 5.5 g. MS m/z (rel. intensity, 70 eV) 250 (M+, 41), 248 (M+, 31), 235 (bp), 233 (79), 62 (26).

Preparation 51

1-[5-BROMO-3-CHLORO-2-(OXIRAN-2-YL-METHOXY)PHENYL]ETHANONE

A mixture of 1-(5-bromo-3-chloro-2-hydroxyphenyl)ethanone (5.5 g, 21.9 mmol), (2R)-(−)Glycidyltosylate (10 g, 43.8 mmol) and $K_2CO_3$ (4.5 g, 32.9 mmol) in DMF (25 ml) was heated at 60° C. for 25 h. The solution was brought to ambient temperature and water and EtOAc was added. The water phase was extracted with EtOAc. The combined organic phases were washed with LiCl (5%), HCl (1 N) and brine and then dried ($Na_2SO_4$) and evaporated to dryness. Purification on flash column chromatography (isooctane/EtOAc) gave the title compound (5.0 g). MS m/z (rel. intensity, 70 eV) 250 (30), 248 (M+, 26), 235 (bp), 233 (85), 57 (90), 306 (M+, 9).

Preparation 52

5-BROMO-3-CHLORO-2-(OXIRAN-2-YLMETHOXY)PHENYL ACETATE

A solution of 1-[5-bromo-3-chloro-2-(oxiran-2-yl-methoxy)phenyl]ethanone (1.7 g, 5.6 mmol) and m-CPBA (2.4 g, 14 mmol) in DCM (30 ml) was heated to 50° C. After 22 h more m-CPBA (2.4 g, 14 mmol) was added and the mixture was heated at 50° C. for another 44 h and then brought to ambient temperature. The solid was filtered off and rinsed. The resulting filtrate was washed with sodium bicarbonate (saturated), brine and further dried ($Na_2SO_4$) and evaporated to dryness to give the crude title compound (2.7 g). MS m/z (rel. intensity, 70 eV) 280 (bp), 278 (84), 224 (54), 222 (52), 57 (79), 322 (M+, 5).

Preparation 53

(7-BROMO-5-CHLORO-2,3-DIHYDRO-1,4-BENZODIOXIN-2-YL)METHANOL

To a solution of 5-bromo-3-chloro-2-(oxiran-2-yl-methoxy)phenyl acetate (4.4 g, 13.7 mmol) in dioxane (20 ml) was added KOH (10%, 40 ml) at 0° C. The reaction mixture was stirred at room temperature for 2 hours. Water was added and the solution was extracted with EtOAc: The combined organic phases were washed with brine, dried ($Na_2SO_4$) and evaporated to dryness. Purification on flash column chromatography (isooctane/EtOAc) gave the title compound (0.34 g). MS m/z (rel. intensity, 70 eV) 280 (M+, bp), 278 (78), 224 (68), 222 (54), 57 (37).

Preparation 54

[(2S)-5-CHLORO-7-(METHYLSULFONYL)-2,3-DIHYDRO-1,4-BENZODIOXIN-2-YL]METHANOL

Preparation according to Preparation 9 using (7-bromo-5-chloro-2,3-dihydro-1,4-benzodioxin-2-yl)methanol (1.07 g, 3.8 mmol), sodium methanesulfinate (85%) (0.6 g, 5.7 mmol), CuI (0.07 g, 0.4 mmol), L-proline (0.09 g, 0.8 mmol) and $K_2CO_3$ (0.04 g, 0.8 mmol) in DMSO (10 ml). Yield (0.33 g). MS m/z (rel. intensity, 70 eV) 280 (38), 278 (M+, bp), 247 (35), 207 (18), 57 (18).

Preparation 55

[(2R)-5-CHLORO-7-(METHYLSULFONYL)-2,3-DIHYDRO-1,4-BENZODIOXIN-2-YL]METHYL 4-METHYLBENZENESULFONATE

Preparation according to Preparation 22 using [(2S)-5-chloro-7-(methylsulfonyl)-2,3-dihydro-1,4-benzodioxin-2-yl]methanol (0.33 g, 1.2 mmol), DCM (10 ml), p-toluenesulfonyl chloride (0.34 g, 1.8 mmol), TEA (0.18 ml, 1.8 mmol) and 4-DMAP (0.15 g, 1.2 mmol). Yield: 0.47 g. MS m/z (rel. intensity, 70 eV) 344 (28), 342 (bp), 340 (74), 263 (18), 233 (31). Molecular ion not found, however fragmentation consistent with the title compound. Used directly in the next step (Example 38) without further analysis.

Preparation 56

1-[2-METHOXY-4-(METHYLTHIO)PHENYL]ETHANONE

Sodium thiomethoxide (1.3 g, 18.5 mmol) in DMF (15 ml) was added to 1-(4-fluoro-2-methoxyphenyl)ethanone (2.85 g, 16.9 mmol) in DMF (5 ml). The mixture was stirred for overnight at room temperature. HCl (1%) was added, the water phase was extracted with EtOAc, the combined organic phases were washed with LiCl (5%), brine and were concentrated to give the title compound (3.6 g) MS m/z (rel. intensity, 70 eV) 196 (M+, 35), 182 (11), 181 (bp), 166 (8), 136 (10).

Preparation 57

1-[2-HYDROXY-4-(METHYLTHIO)PHENYL]ETHANONE

Boron tribromide (19 ml, 1 N in DCM, 19 mmol) was added to a mixture of crude 1-[2-methoxy-4-(methylthio)phenyl]ethanone (3.6 g, 16.9 mmol) and DCM (25 ml) at 0° C. The mixture was brought to room temperature and stirred for 3 h. Ice/water was added, the organic phase was separated and the water phase was extracted with EtOAc. The combined organic phases were filtered through a short plug of silica (EtOAc) and were concentrated to give the title compound (3.0 g) MS m/z (rel. intensity, 70 eV) 183 (6), 182 (M+, 53), 168 (10), 167 (bp), 152 (6).

Preparation 58

1-[2-HYDROXY-4-(METHYLSULFONYL)PHENYL]ETHANONE

Preparation according to Preparation 28 using 1-[2-hydroxy-4-(methylthio)phenyl]ethanone (3.0 g, 16.6 mmol), $Na_2WO_4.2H_2O$ (0.056 g, 0.17 mmol) and hydrogen peroxide (4.2 ml, 41.3 mmol) in acetic acid (15 ml) heated at 60° C. for overnight. Yield: 3.0 g. MS m/z (rel. intensity, 70 eV) 214 (M+, 18), 200 (12), 199 (bp), 137 (47), 120 (13).

Preparation 59

7-(METHYLSULFONYL)-4-OXO-4H-CHROMENE-2-CARBOXYLATE

A solution of sodium (1.87 g, 81.5 mmol) in EtOH (70 ml) was added to a mixture of 1-[2-hydroxy-4-(methylsulfonyl)phenyl]ethanone (3.52 g, 16.3 mmol), diethyl oxalate (7.14 g, 48.9 mmol) and EtOH (40 ml). The mixture was heated at reflux for 2 h. The mixture was cooled to ambient temperature and HCl (conc.), EtOAc and HCl (10%) was added. The phases were separated and the combined organic phases were washed with brine, dried ($Na_2SO_4$), filtered and concentrated. Purification by flash chromatography (EtOAc/Isooctane/MeOH) gave the title compound. Yield 5.5 g. MS m/z (rel. intensity, 70 eV) 297 (15), 296 (M+, bp), 268 (27), 217 (60), 189 (19).

Preparation 60

ETHYL 7-(METHYLSULFONYL)CHROMANE-2-CARBOXYLATE

A mixture of ethyl 7-(methylsulfonyl)-4-oxo-4H-chromene-2-carboxylate (1.3 g, 4.4 mmol), palladium on carbon (10%, 0.44 g), MeOH (45 ml) and AcOH (5 ml) was hydrogenated at 40 Psi for 64 h at 60° C. Filtration through Celite (EtOAc) and evaporation followed by filtration through a plug of $Al_2O_3$ (EtOAc/ACN) gave the title compound. Yield: 0.6 g. MS m/z (rel. intensity, 70 eV) 307 (64), 302 (91), 286 (14), 285 (M+1, bp), 211 (18).

Preparation 61

[7-(METHYLSULFONYL)-3,4-DIHYDRO-2H-CHROMEN-2-YL]METHANOL

A mixture of ethyl 7-(methylsulfonyl)chromane-2-carboxylate (0.6 g, 2.1 mmol), $LiBH_4$ (0.18 g, 8.5 mmol) and THF (8 ml) was stirred at 0° C. for 15 min and 2 h at room temperature. HCl (10%) and EtOAc was added, the organic phase was dried ($Na_2SO_4$), filtered and concentrated to give the title compound. Yield 0.66 g. MS m/z (rel. intensity, 70 eV) 507 (20), 485 (25), 265 (23), 244 (13), 243 (M+1, bp).

Preparation 62

[7-(METHYLSULFONYL)-3,4-DIHYDRO-2H-CHROMEN-2-YL]METHYL 4-METHYLBENZENESULFONATE

Preparation according to Preparation 22 using [7-(methylsulfonyl)-3,4-dihydro-2H-chromen-2-yl]methanol (0.4 g, 1.65 mmol), DCM (25 ml), p-toluenesulfonyl chloride (0.47 g, 2.5 mmol), TEA (0.28 ml, 2.0 mmol) and 4-DMAP (0.24 g, 2.0 mmol) stirred for overnight at room temperature. Yield: 0.59 g. MS m/z (rel. intensity, 70 eV) 419 (62), 416 (14), 415 (25), 414 (bp), 397 (M+1, 39).

Preparation 63

[(2S)-7-(METHYLSULFONYL)-2,3-DIHYDRO-1,4-BENZODIOXIN-2-YL]METHYLAMINE

A mixture of [(2R)-7-(methylsulfonyl)-2,3-dihydro-1,4-benzodioxin-2-yl]methyl 4-methylbenzenesulfonate (1.1 g, 2.5 mmol), NH₃ (4 ml, 7N in methanol) was heated under microwave radiation at 120° C. for 20 min. The product was evaporated to dryness and was purified by flash column chromatography (EtOAc/MeOH). Yield 0.31 g. MS m/z (rel. intensity, 70 eV) 243 (M+, 35), 214 (bp), 199 (35), 79 (25), 56 (22).

Preparation 64

[(2S)-5-FLUORO-7-(METHYLSULFONYL)-2,3-DIHYDRO-1,4-BENZODIOXIN-2-YL]METHYLAMINE

A mixture of [(2R)-5-fluoro-7-(methylsulfonyl)-2,3-dihydro-1,4-benzodioxin-2-yl]methyl 4-methylbenzenesulfonate (0.7 g, 1.7 mmol), NH₃ (6 ml, 7N in methanol) was heated under microwave radiation at 120° C. for 20 min. The product was evaporated to dryness and was purified on an SCX-3 column (TEA/MeOH) Yield 0.34 g. MS m/z (rel. intensity, 70 eV) 261 (M+, bp), 217 (49), 97 (39), 69 (55), 56 (79).

Preparation 65

ETHYL 7-HYDROXYCHROMANE-2-CARBOXYLATE

A mixture of ethyl 7-hydroxy-4-oxo-4H-chromene-2-carboxylate (10 g, 41 mmol) in MeOH (20 ml) and AcOH (20 ml) was hydrogenated at 50 Psi for 4 days. Filtration and evaporation gave the title compound. Yield: 9.2 g. MS m/z (rel. intensity, 70 eV) 222 (M+, 44), 149 (bp), 148 (22), 147 (46), 121 (25).

Preparation 66

ETHYL 7-{[(TRIFLUOROMETHYL)SULFONYL]OXY}CHROMANE-2-CARBOXYLATE

A mixture of ethyl 7-hydroxychromane-2-carboxylate (9.8 g, 44 mmol) in CH₂Cl₂ (150 ml) was cooled to 0° C., was added pyridine (6.97 g, 88 mmol) and trifluoromethanesulfonic anhydride (8.9 ml, 53 mmol) added in portions during 40 min and then brought to ambient temperature and stirred for 2 h. HCl (aq, 10%) was added and the solution was extracted with CH₂Cl₂. The combined organic phases were washed with Na₂CO₃ (10% in H₂O), Na₂CO₃ (sat.), dried (Na₂SO₄) and evaporated to dryness to give the crude title compound (13.2 g). MS m/z (rel. intensity, 70 eV) 354 (M+, 41), 281 (bp), 280 (16), 147 (42), 103 (19).

Preparation 67

ETHYL 7-[(TRIISOPROPYLSILYL)THIO]CHROMANE-2-CARBOXYLATE

To a suspension of NaH (1.02 g, 25.6 mmol, 60% in mineral oil) in toluene (60 ml) was added triisopropylsilanethiol (4.24 g, 22.3 mmol). After stirring at room temperature for 30 min, to the mixture were added a solution of ethyl 7-{[(trifluoromethyl)sulfonyl]oxy}chromane-2-carboxylate (6.07 g, 17.1 mmol) in THF (60 ml) and tetrakis(triphenylphosphine)palladium (0.39 g, 0.34 mmol), and the mixture was degassed under N₂. After heating at 90° C. for 1.5 h under N₂, the solvents were evaporated and the residue was purified by column chromatography (EtOAc/Isooctane) to afford the title compound. Yield: 6.84 g. MS m/z (rel. intensity, 70 eV) 394 (M+, 27), 277 (52), 352 (26), 351 (bp), 251 (50).

Preparation 68

ETHYL 7-MERCAPTOCHROMANE-2-CARBOXYLATE

To a mixture of ethyl 7-[(triisopropylsilyl)thio]chromane-2-carboxylate (5.6 g, 14.2 mmol) in EtOH (100 ml) was added concentrated HCl (4 ml) and the mixture was stirred at room temperature for 3 h. Evaporation to dryness gave the title compound. Yield: 3.4 g. MS m/z (rel. intensity, 70 eV) 238 (M+, 75), 165 (bp), 163 (56), 132 (50), 131 (43).

Preparation 69

ETHYL 7-(METHYLTHIO)CHROMANE-2-CARBOXYLATE

A mixture of ethyl 7-mercaptochromane-2-carboxylate (3.4 g, 14.3 mmol), Methyliodide (3.03 g, 21.4 mmol) and K₂CO₃ (7.88 g, 57 mmol) in ACN (100 ml) was stirred for 2 h at RT. Filtration and evaporation of solvents gave the title compound (3.28 g). MS m/z (rel. intensity, 70 eV) 252 (M+, bp), 179 (94), 177 (40), 132 (55), 131 (63).

Preparation 70

ETHYL 7-(METHYLSULFONYL)CHROMANE-2-CARBOXYLATE

A mixture of ethyl 7-(methylthio)chromane-2-carboxylate (3.28 g, 13.0 mmol), Na₂WO₄.2H₂O (0.04 g, 0.13 mmol) and hydrogen peroxide (3.3 ml, 32.5 mmol) in acetic acid (40 ml) was heated at 60° C. for 1 h. Na₂S₂O₅ (5%, 150 ml) added and the solution was extracted with EtOAc. The combined organic phases were washed with Na₂CO₃ (10%), dried (MgSO₄) and evaporated to dryness to give the crude title compound (2.44 g). MS m/z (rel. intensity, 70 eV) 284 (M+, 37), 211 (bp), 149 (27), 132 (54), 131 (55).

Biological Activity

The following tests are used for evaluation of the compounds according to the invention.

In Vivo Test: Behaviour

Behavioural activity may be determined using eight Digiscan activity monitors (RXYZM (16) TAO, Omnitech Electronics, Columbus, Ohio, USA), connected to an Omnitech Digiscan analyzer and an Apple Macintosh computer equipped with a digital interface board (NB D10-24, National Instruments, USA). Each activity monitor consists of a quadratic metal frame (W×L=40 cm×40 cm) equipped with photobeam sensors. During measurements of behavioural activity, a rat is put in a transparent acrylic cage (W×L×H, 40×40×30 cm) which in turn is placed in the activity monitor. Each activity monitor is equipped with three rows of infrared photobeam sensors, each row consisting of 16 sensors. Two rows are placed along the front and the side of the floor of the cage, at a 90° angle, and the third row is placed 10 cm above the floor to measure vertical activity. Photobeam sensors are spaced 2.5 cm apart. Each activity monitor is fitted in an identical sound and light attenuating box containing a weak house light and a fan.

The computer software is written using object oriented programming (LabVIEW®, National instruments, Austin, Tex., USA).

Behavioural data from each activity monitor, representing the position (horizontal center of gravity and vertical activity) of the animal at each time, are recorded at a sampling frequency of 25 Hz and collected using a custom written LABView™ application. The data from each recording session are stored and analyzed with respect to distance traveled. Each behavioural recording session lasts 60 min, starting approximately 4 min after the injection of test compound. Similar behavioural recording procedures are applied for drug-naïve and drug pre-treated rats. Rats pre-treated with d-amphetamine are given a dose of 1.5 mg/kg i.p. 10 min before the recording session in the activity monitor. Rats pre-treated with MK-801 are given a dose of 0.7 mg/kg i.p. 90 min before the recording session in the activity monitor. The results are presented as counts/60 minutes, or counts/30 minutes, in arbitrary length units. Statistical comparisons are carried out using Student's t-test against the control group. In MK-801 or amphetamine pre-treated animals, statistical comparisons are made against the MK801 or d-amphetamine controls, respectively.

$ED_{50}$ values for reduction of amphetamine-induced hyperlocomotion are calculated by curve fitting. For most compounds, the evaluation is based on 16 amphetamine pre-treated animals over the dose range 0, 11, 33 and 100 µmol/kg s.c. in one single experiment, with complementary doses in separate experiments. Calculations are based on distance during the last 45 minutes of one hour of measurement. The distances are normalised to amphetamine-control and fitted by least square minimization to the function "End−(End−Control)/(1+(dose/$ED_{50}$)$^{Slope}$)". The four parameters (Control, End, $ED_{50}$ and Slope) are fitted with the restrictions: $ED_{50}$>0, 0.5<Slope<3, End=0% of control. The restriction with locked End is made to focus on potency rather than efficacy. To estimate confidence levels for the parameters, the fit is repeated 100 times with a random evenly distributed squared weight (0 to 1) for every measurement value. Presented $ED_{50}$-ranges cover 95% of these values.

In Vivo Test: Neurochemistry

After the behavioural activity sessions, the rats are decapitated and their brains rapidly taken out and put on an ice-cold petri-dish. The limbic forebrain, the striatum, the frontal cortex and the remaining hemispheral parts of each rat are dissected and frozen. Each brain part is subsequently analyzed with respect to its content of monoamines and their metabolites.

The monoamine transmitter substances (NA (noradrenaline), DA (dopamine), 5-HT (serotonin)) as well as their amine (NM (normethanephrine), 3-MT (3-methoxytyramine)) and acid (DOPAC (3,4-dihydroxyphenylacetic acid), 5-HIAA (5-hydroxyindoleacetic acid), HVA (homovanillic acid)) metabolites are quantified in brain tissue homogenates by HPLC separations and electrochemical detection.

The analytical method is based on two chromatographic separations dedicated for amines or acids. Two chromatographic systems share a common auto injector with a 10-port valve and two sample loops for simultaneous injection on the two systems. Both systems are equipped with a reverse phase column (Luna C18(2), dp 3 µm, 50*2 mm i.d., Phenomenex) and electrochemical detection is accomplished at two potentials on glassy carbon electrodes (MF-1000, Bioanalytical Systems, Inc.). The column effluent is passed via a T-connection to the detection cell or to a waste outlet. This is accomplished by two solenoid valves, which block either the waste or detector outlet. By preventing the chromatographic front from reaching the detector, better detection conditions are achieved. The aqueous mobile phase (0.4 ml/min) for the acid system contains citric acid 14 mM, sodium citrate 10 mM, MeOH 15% (v/v) and EDTA 0.1 mM. Detection potentials relative to Ag/AgCl reference are 0.45 and 0.60V. The aqueous ion pairing mobile phase (0.5 ml/min) for the amine system contains citric acid 5 mM, sodium citrate 10 mM, MeOH 9% (v/v), MeCN 10.5% v/v), decane sulfonic acid 0.45 mM, and EDTA 0.1 mM. Detection potentials relative to Ag/AgCl reference are 0.45 and 0.65V.

$ED_{50}$ values for the increase of DOPAC in striatum are calculated by curve fitting. For most compounds, the evaluation is based on 20 animals over the dose range 0, 3.7, 11, 33 and 100 µmol/kg s.c. in one single experiment, with complementary doses in separate experiments. The DOPAC levels are normalised to control and fitted by least square minimization to the function "End−(End−Control)/(1+(dose/$ED_{50}$)$^{Slope}$)". The four parameters (Control, End, $ED_{50}$ and Slope) are fitted with the restrictions: $ED_{50}$>0, 0.5<Slope<3, 350<End<400% of control. To estimate confidence levels for the parameters, the fit is repeated 100 times with a random evenly distributed squared weight (0 to 1) for every measurement value. Presented $ED_{50}$-ranges cover 95% of these values.

In Vivo Test: Oral Bioavailability

Experiments are performed 24 hours after implantation of arterial and venous catheters. Test compound is administered orally at 12.5 µmol/kg or intravenously at 5 µmol/kg using the venous catheters, n=3 per group. Arterial blood samples are then taken during six hours at 0, 3, 9, 27, 60, 120, 180, 240, 300 and, 360 minutes after administration of the test compound. The oral bioavailability is calculated as the ratio of the AUC (Area under curve) obtained after oral administration over the AUC obtained after intravenous administration for each rat. The parameter AUC is calculated according to the following:

AUC: the area under the plasma concentration versus time curve from time zero to the last concentration measured (Clast), calculated by the log/linear trapezoidal method.

The levels of test compound are measured by means of liquid chromatography-mass spectrometry (LC-MS) (Hewlett-Packard 1100MSD Series). The LC-MS module includes a quaternary pump system, vacuum degasser, thermostatted autosampler, thermostatted column compartment, diode array detector and API-ES spray chamber. Data handling is performed with a HP ChemStation rev.A.06.03. system. Instrument settings: MSD mode: Selected ion monitoring (SIM) MSD polarity: Positiv Gas temp: 350° C. Drying gas: 13.0 l/min Nebulizer gas: 50 psig Capillary voltage: 5000 V Fragmentor voltage: 70 V Analytical column: Zorbax eclipse XDB-C8 (4.6*150 mm, 5 µm) at 20° C. The mobile phase is acetic acid (0.03%) (solvent A) and acetonitrile (solvent B). The flow rate of the mobile phase is 0.8 ml/min. The elution is starting at 12% of solvent β isocratic for 4.5 min, then increasing linearity to 60% over 4.5 min.

Extractions procedure: Plasma samples (0.25-0.5 ml) are diluted with water to 1 ml, and 60 µmol (100 µl) internal standard (−)-OSU6241 is added. The pH is adjusted to 11 by the addition of 25 µl saturated $Na_2CO_3$. After mixing, the samples are extracted with 4 ml dichloromethane by shaking for 20 min. The organic layer is after centrifugation transferred to a smaller tube and evaporated to dryness under a stream of nitrogen. The residue is then dissolved in 120 µl mobile phase (acetic acid (0.03%): acetonitrile, 95:5) for LC-MS analysis (10 µl injected). The selective ion (MH$^+$) is monitored for each Example, and MH$^+$ 296 for (−)-OSU6241 ((3-[3-(ethylsulfonyl)phenyl]-1-propylpiperidine).

A standard curve over the range of 1-500 pmol is prepared by adding appropriate amounts of test compound to blank plasma samples.

In Vitro Test: Metabolic Stability in Rat Liver Microsomes

Rat liver microsomes are isolated as described by Förlin [Förlin L: Effects of Clophen A50, 3-methylcholantrene, pregnenolone-16aq-carbonitrile and Phenobarbital on the hepatic microsomal cytochrome P-450-dependent monooxygenaser system in rainbow trout, salmo gairdneri, of different age and sex; *Tox. Appl. Pharm.* 1980 54 (3) 420-430] with minor modifications, e.g. 3 mL/g liver of a 0.1 M Na/K*$PO_4$ buffer with 0.15M KCl, pH 7.4, (buffer 1) is added before homogenisation, the homogenate is centrifuged for 20 minutes instead of 15, the supernatant is ultracentrifuged at 100.000 g instead of 105.000 g and the pellet from the ultracentrifugation is resuspended in 1 mL/g liver of 20% v/v 87% glycerol in buffer 1.

1 μL, 0.2 or 1 mM test substance diluted in water, and 10 μL 20 mg/mL rat liver microsome are mixed with 149 μL 37° C. buffer 1 and the reaction is started by addition of 40 μL 4.1 mg/mL NADPH. After 0 or 15 minutes incubation at 37° C. in a heating block (LAB-LINE, MULTI-BLOK Heater or lab4you, TS-100 Thermo shaker at 700 rpm) the reaction is stopped by addition of 100 μL pure acetonitrile. The protein precipitation is then removed by rejecting the pellet after centrifugation at 10.000 g for 10 minutes (Heraeus, Biofuge fresco) in 4° C. The test compound is analysed using HPLC-MS (Hewlett-Packard 1100MSD Series) with a Zorbax SB-C18 column (2.1*150 mm, 5 μm) using 0.03% formic acid and acetonitrile as mobile phase (gradient) or a Zorbax Eclipse XDB-C18 (3*75 mm, 3.5 μm) using 0.03% acetic acid and acetonitrile as mobile phase (gradient). The 15 min turnover is calculated as the fraction of test compound eliminated after 15 minutes, expressed in percent of 0 min levels, i.e. 100*[conc test compound at 0 min−concentration at 15 min]/conc at 0 min.

Preparation of liver microsomes is performed as described by Förlin [Förlin L: Effects of Clophen A50, 3-methylcholantrene, pregnenolone-16aq-carbonitrile and Phenobarbital on the hepatic microsomal cytochrome P-450-dependent monooxygenaser system in rainbow trout, salmo gairdneri, of different age and sex; *Tox. Appl. Pharm.* 1980 54 (3) 420-430].

Protocols for incubation with liver microsomes are described by Crespi & Stresser [Crespi C L, D M Stresser: Fluorometric screening for metabolism based drug-drug interactions; *J. Pharm. Tox. Meth.* 2000 44 325-331] and Renwick et al. [Renwick et al.: Metabolism of 2,5-bis(trifluoromethyl)-7-benzyloxy-4-trifluoromethylcoumarin by human hepatic CYP isoforms: evidence for selectivity towards CYP3A4; *Xenobiotica* 2001 31 (4) 187-204].

Microdialysis

Male Sprague-Dawley rats weighing 220-320 g are used throughout the experiments. Before the experiment the animals are group housed, five animals in each cage, with free access to water and food. The animals are housed at least one week after arrival prior to surgery and use in the experiments. Each rat is used only once for microdialysis.

We use a modified version according to Waters et al. [Waters N, Lofberg L, Haadsma-Svensson S, Svensson K, Sonesson C and Carlsson A: Differential effects of dopamine D2 and D3 receptor antagonists in regard to dopamine release, in vivo receptor displacement and behaviour." *J. Neural. Transm. Gen. Sect.* 1994 98 (1) 39-55] of the I-shaped probe according to Santiago & Westerink [Santiago M, Westerink BHC: Characterization of the in vivo release of dopamine as recorded by different types of intracerebral microdialysis probes; *Naunyn-Schmiedeberg's Arch. Pharmacol.* 1990 342 407-414]. The dialysis membrane we use is the AN69 polyacrylonitrile/35 sodiummethalylsulfonate copolymer (HOSPAL; o.d./i.d. 310/220 μm: Gambro, Lund, Sweden). In the dorsal striatum we use probes with an exposed length of 3 mm of dialysis membrane and in the prefrontal cortex the corresponding length is 2.5 mm. The rats are operated under isoflurane inhalationanesthesia while mounted into a Kopf stereotaxic instrument. Co-ordinates are calculated relative to bregma; dorsal striatum AP +1, ML ±2.6, DV −6.3; Pf cortex, AP +3.2, 8° ML ±1.2, DV −4.0 according to Paxinos & Watson [Paxinos G, Watson C: The Rat Brain in Stereotaxic Coordinates; Academic Press, New York 1986]. The dialysis probe is positioned in a burr hole under stereotaxic guidance and cemented with phosphatine dental cement.

The rats are housed individually in cages for 48 h before the dialysis experiments, allowing them to recover from surgery and minimizing the risk of drug interactions with the anaesthetic during the following experiments. During this period the rats have free access to food and water. On the day of experiment the rats are connected to a micro perfusion pump via a swiwel and are replaced in the cage where they can move freely within its confinements. The perfusion medium is a Ringer's solution containing in mmol/l: NaCl; 140, $CaCl_2$; 1.2, KCl; 3.0, $MgCl_2$; 1.0 and ascorbic acid; 0.04 according to Moghaddam & Bunney [Moghaddam B, Bunney B S: Ionic Composition of Microdialysis Perfusing Solution Alters the Pharmacological Responsiveness and Basal Outflow of Striatal Dopamine; *J. Neurochem.* 1989 53 652-654]. The pump is set to a perfusion speed of 2 μl/min and 40 μl samples are collected every 20 min.

Each sample is analyzed at two HPLC systems. On an autoinjector (CMA 200) with a 10-port valve (Valco C10WE), holding two sample loops in series (4 μl and 20 μl), each brain dialysate sample is loaded in both loops simultaneously. At injection the 20 μl sample is introduced into a column switching system (reverse-phase combined with reverse-phase ion-pairing) for dopamine (DA), noradrenaline (NA), normetanephrine (NM), 3-methoxytyramine (3-MT) and serotonin (5-hydroxytryptamine, 5-HT) determination, while the 4 μl sample is introduced on a reverse-phase column for the chromatography of the acidic monoamine metabolites 3,4-di-hydroxyphenylacetic acid (DOPAC), homovanillic acid (HVA) and 5-hydroxyindoleacetic acid (5-HIAA). The currents generated by the two EC detectors are converted to digital data and evaluated using Chromeleon software (Dionex) on a PC. The method sample turn over time is 4.5 min and two parallel experiments are normally analyzed simultaneously on the system.

After the experiment the rats are uncoupled from the perfusion pump and decapitated. Their brains are rapidly taken out and fixed in Neo-fix solution (Kebo-lab, Sweden) for subsequent inspection of probe localisation. The Animal Ethics Committee in Göteborg, Sweden approved the procedures applied in these experiments.

The invention claimed is:

1. A compound of Formula 1:

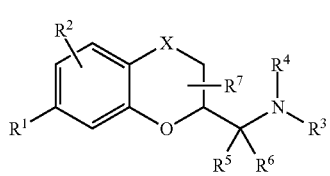

(1)

any of its stereoisomers or any mixture of its stereoisomers, or an N-oxide thereof, or a pharmaceutically acceptable salt thereof; wherein:

X is O;

$R^1$ is selected from the group consisting of $SOR^8$, $SO_2R^8$, $SO_2NH_2$ and $SO_2NH(CH_3)$;

R² is selected from the group consisting of H, CN, F, Cl, Br, I and CH₃;

R³ is selected from the group consisting of C₁-C₅ alkyl, allyl, CH₂CH₂OCH₃, CH₂CH₂CH₂F, CH₂CH₂CHF₂, CH₂CH₂F, 3,3,3-trifluoropropyl, 4,4,4-trifluorobutyl, CH₂CH₂OH, CH₂CH₂CH₂OH, CH₂CH(OH)CH₃, CH₂CH₂COCH₃, C₃-C₆ cycloalkyl,

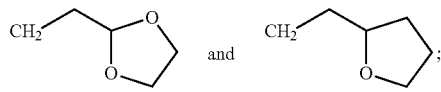

and

R⁴ is selected from the group consisting of H, C₁-C₅ alkyl, allyl, CH₂CH₂OCH₃, CH₂CH₂CH₂F, CH₂CH₂CHF₂, CH₂CH₂F, 3,3,3-trifluoropropyl, 4,4,4-trifluorobutyl, CH₂CH₂OH, CH₂CH₂CH₂OH, CH₂CH(OH)CH₃, CH₂CH₂COCH₃,

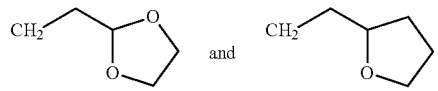

R⁵, R⁶ and R⁷ are selected from the group consisting of H and CH₃; and

R⁸ is selected from the group consisting of C₁-C₃ alkyl, CF₃, CHF₂, CH₂F and CN.

2. The compound according to claim 1, any of its stereoisomers or any mixture of its stereoisomers, or an N-oxide thereof, or a pharmaceutically acceptable salt thereof, wherein
R¹ is selected from the group consisting of SO₂R⁸; and
R⁸ is selected from the group consisting of C₁-C₃ alkyl and CF₃.

3. The compound according to claim 1, any of its stereoisomers or any mixture of its stereoisomers, or an N-oxide thereof, or a pharmaceutically acceptable salt thereof, wherein R² is selected from the group consisting of H, F and Cl.

4. The compound according to claim 1, any of its stereoisomers or any mixture of its stereoisomers, or an N-oxide thereof, or a pharmaceutically acceptable salt thereof, wherein R³ is selected from the group consisting of C₁-C₅ alkyl, allyl, 3,3,3-trifluoropropyl, CH₂CH₂OH, and CH₂CH₂COCH₃.

5. The compound according to claim 1, any of its stereoisomers or any mixture of its stereoisomers, or an N-oxide thereof, or a pharmaceutically acceptable salt thereof, wherein R⁴ is selected from the group consisting of H and C₁-C₅ alkyl.

6. The compound according to claim 1, any of its stereoisomers or any mixture of its stereoisomers, or an N-oxide thereof, or a pharmaceutically acceptable salt thereof, wherein R⁵, R⁶ and R⁷ all represent H.

7. The compound according to claim 1, any of its stereoisomers or any mixture of its stereoisomers, or an N-oxide thereof, or a pharmaceutically acceptable salt thereof, wherein
X represents O;
R¹ represents SO₂R⁸;
R² represents H, F or Cl;
R³ represents C₁-C₅ alkyl, allyl, CH₂CH₂OCH₃, 3,3,3-trifluoropropyl or CH₂CH₂OH; and R⁴ represents H or C₁-C₅ alkyl;
R⁵, R⁶ and R⁷ all represent H; and
R⁸ represents C₁-C₃ alkyl or CF₃.

8. The compound according to claim 1, which is
N-{[7-(METHYLSULFONYL)-2,3-DIHYDRO-1,4-BENZODIOXIN-2-YL]METHYL}-PROPAN-1-AMINE;
N-{[(2R)-7-(METHYLSULFONYL)-2,3-DIHYDRO-1,4-BENZODIOXIN-2-YL]METHYL}-PROPAN-1-AMINE;
N-{[(2S)-7-(METHYLSULFONYL)-2,3-DIHYDRO-1,4-BENZODIOXIN-2-YL]METHYL}-PROPAN-1-AMINE;
N-{[7-(METHYLSULFONYL)-2,3-DIHYDRO-1,4-BENZODIOXIN-2-YL]METHYL}ETHANAMINE;
N-{[(2S)-7-(METHYLSULFONYL)-2,3-DIHYDRO-1,4-BENZODIOXIN-2-YL]METHYL}ETHANAMINE;
N-METHYL-1-[7-(METHYLSULFONYL)-2,3-DIHYDRO-1,4-BENZODIOXIN-2-YL]METHANAMINE;
N-METHYL-1-[(2S)-7-(METHYLSULFONYL)-2,3-DIHYDRO-1,4-BENZODIOXIN-2-YL]METHANAMINE;
2-METHYL-N-{[(2R)-7-(METHYLSULFONYL)-2,3-DIHYDRO-1,4-BENZODIOXIN-2-YL]METHYL}PROPAN-1-AMINE;
2-METHYL-N-{[(2S)-7-(METHYLSULFONYL)-2,3-DIHYDRO-1,4-BENZODIOXIN-2-YL]METHYL}PROPAN-1-AMINE;
N-METHYL-N-{[7-(METHYLSULFONYL)-2,3-DIHYDRO-1,4-BENZODIOXIN-2-YL]METHYL}PROPAN-1-AMINE;
N-{[7-(METHYLSULFONYL)-2,3-DIHYDRO-1,4-BENZODIOXIN-2-YL]METHYL}-N-PROPYLPROPAN-1-AMINE;
N-{[5-FLUORO-7-(METHYLSULFONYL)-2,3-DIHYDRO-1,4-BENZODIOXIN-2-YL]METHYL}-N-PROPAN-1-AMINE;
N-{[5-FLUORO-7-(METHYLSULFONYL)-2,3-DIHYDRO-1,4-BENZODIOXIN-2-YL]METHYL}ETHANAMINE;
N-{[(2S)-5-FLUORO-7-(METHYLSULFONYL)-2,3-DIHYDRO-1,4-BENZODIOXIN-2-YL]METHYL}ETHANAMINE;
1-[5-FLUORO-7-(METHYLSULFONYL)-2,3-DIHYDRO-1,4-BENZODIOXIN-2-YL]-N-METHYLMETHANAMINE;
N-{[(2S)-5-FLUORO-7-(METHYLSULFONYL)-2,3-DIHYDRO-1,4-BENZODIOXIN-2-YL]METHYL}PROPAN-1-AMINE;
N-{[(2S)-7-(TRIFLUOROMETHYLSULFONYL)-2,3-DIHYDRO-1,4-BENZODIOXIN-2-YL]METHYL}ETHANAMINE;
N-{[(2S)-7-(TRIFLUOROMETHYLSULFONYL)-2,3-DIHYDRO-1,4-BENZODIOXIN-2-YL]METHYL}PROPAN-1-AMINE;
N-{[7-(METHYLSULFONYL)-2,3-DIHYDRO-1,4-BENZODIOXIN-2-YL]METHYL}PROP-2-EN-1-AMINE;
N-{[7-(METHYLSULFONYL)-2,3-DIHYDRO-1,4-BENZODIOXIN-2-YL]METHYL}BUTAN-1-AMINE;
N,N-DIMETHYL-N-{[7-(METHYLSULFONYL)-2,3-DIHYDRO-1,4-BENZODIOXIN-2-YL]METHANAMINE;

N-ETHYL-N-{[7-(METHYLSULFONYL)-2,3-DIHYDRO-1,4-BENZODIOXIN-2-YL]METHYL}ETHANAMINE;
N-{[7-(METHYLSULFONYL)-2,3-DIHYDRO-1,4-BENZODIOXIN-2-YL]METHYL}PROPAN-2-AMINE;
N-ETHYL-N-{[7-(METHYLSULFONYL)-2,3-DIHYDRO-1,4-BENZODIOXIN-2-YL]METHYL}-N-PROPAN-1-AMINE;
2-({[7-(METHYLSULFONYL)-2,3-DIHYDRO-1,4-BENZODIOXIN-2-YL]METHYL}AMINO)ETHANOL;
N-METHYL-N-{[7-(METHYLSULFONYL)-2,3-DIHYDRO-1,4-BENZODIOXIN-2-YL]METHYL}ETHANAMINE;
2-METHOXY-N-{[7-(METHYLSULFONYL)-2,3-DIHYDRO-1,4-BENZODIOXIN-2-YL]METHYL}ETHANAMINE;
2-METHYL-N-{[7-(METHYLSULFONYL)-2,3-DIHYDRO-1,4-BENZODIOXIN-2-YL]METHYL}PROPAN-1-AMINE;
N-{[(2S)-8-FLUORO-7-(METHYLSULFONYL)-2,3-DIHYDRO-1,4-BENZODIOXIN-2-YL]METHYL}ETHANAMINE;
N-{[(2S)-5-CHLORO-7-(METHYLSULFONYL)-2,3-DIHYDRO-1,4-BENZODIOXIN-2-YL]METHYL}ETHANAMINE;
N-{[(2S)-7-(METHYLSULFONYL)-2,3-DIHYDRO-1,4-BENZODIOXIN-2-YL]METHYL}-N-(3,3,3-TRIFLUOROPROPYL)AMINE;
N-{[(2S)-5-FLUORO-7-(METHYLSULFONYL)-2,3-DIHYDRO-1,4-BENZODIOXIN-2-YL]METHYL}-N-(3,3,3-TRIFLUOROPROPYL)AMINE;
1-[(2S)-5-FLUORO-7-(METHYLSULFONYL)-2,3-DIHYDRO-1,4-BENZODIOXIN-2-YL]-N-METHYLMETHANAMINE;
N-{[5-FLUORO-7-(METHYLSULFONYL)-2,3-DIHYDRO-1,4-BENZODIOXIN-2-YL]METHYL}PROP-2-EN-1-AMINE;
—N-{[5-FLUORO-7-(METHYLSULFONYL)-2,3-DIHYDRO-1,4-BENZODIOXIN-2-YL]METHYL}BUTAN-1-AMINE;
N-{[5-FLUORO-7-(METHYLSULFONYL)-2,3-DIHYDRO-1,4-BENZODIOXIN-2-YL]METHYL}-N-PROPYLPROPAN-1-AMINE;
1-[5-FLUORO-7-(METHYLSULFONYL)-2,3-DIHYDRO-1,4-BENZODIOXIN-2-YL]-N,N-DIMETHYLMETHANAMINE;
N-ETHYL-N-{[5-FLUORO-7-(METHYLSULFONYL)-2,3-DIHYDRO-1,4-BENZODIOXIN-2-YL]METHYL}ETHANAMINE;
N-{[5-FLUORO-7-(METHYLSULFONYL)-2,3-DIHYDRO-1,4-BENZODIOXIN-2-YL]METHYL}PROPAN-2-AMINE;
N-{[5-FLUORO-7-(METHYLSULFONYL)-2,3-DIHYDRO-1,4-BENZODIOXIN-2-YL]METHYL}-N-METHYLPROPAN-1-AMINE;
N-ETHYL-N-{[5-FLUORO-7-(METHYLSULFONYL)-2,3-DIHYDRO-1,4-BENZODIOXIN-2-YL]METHYL}PROPAN-1-AMINE;
2-({[5-FLUORO-7-(METHYLSULFONYL)-2,3-DIHYDRO-1,4-BENZODIOXIN-2-YL]METHYL}AMINO)ETHANOL;
N-{[5-FLUORO-7-(METHYLSULFONYL)-2,3-DIHYDRO-1,4-BENZODIOXIN-2-YL]METHYL}-N-METHYLETHANAMINE;
N-{[5-FLUORO-7-(METHYLSULFONYL)-2,3-DIHYDRO-1,4-BENZODIOXIN-2-YL]METHYL}-2-METHOXYETHANAMINE;
N-{[5-FLUORO-7-(METHYLSULFONYL)-2,3-DIHYDRO-1,4-BENZODIOXIN-2-YL]METHYL}-2-METHYLPROPAN-1-AMINE;
N-{[(2S)-5-CHLORO-7-(METHYLSULFONYL)-2,3-DIHYDRO-1,4-BENZODIOXIN-2-YL]METHYL}PROP-2-EN-1-AMINE;
N-{[(2S)-5-CHLORO-7-(METHYLSULFONYL)-2,3-DIHYDRO-1,4-BENZODIOXIN-2-YL]METHYL}BUTAN-1-AMINE;
N-{[(2S)-5-CHLORO-7-(METHYLSULFONYL)-2,3-DIHYDRO-1,4-BENZODIOXIN-2-YL]METHYL}-N-PROPYLPROPAN-1-AMINE;
1-[(2S)-5-CHLORO-7-(METHYLSULFONYL)-2,3-DIHYDRO-1,4-BENZODIOXIN-2-YL]-N,N-DIMETHYLMETHANAMINE;
N-ETHYL-N-{[(2S)-5-CHLORO-7-(METHYLSULFONYL)-2,3-DIHYDRO-1,4-BENZODIOXIN-2-YL]METHYL}ETHANAMINE;
N-{[(2S)-5-CHLORO-7-(METHYLSULFONYL)-2,3-DIHYDRO-1,4-BENZODIOXIN-2-YL]METHYL}PROPAN-2-AMINE;
N-{[(2S)-5-CHLORO-7-(METHYLSULFONYL)-2,3-DIHYDRO-1,4-BENZODIOXIN-2-YL]METHYL}-N-METHYLPROPAN-1-AMINE;
N-ETHYL-N-{[(2S)-5-CHLORO-7-(METHYLSULFONYL)-2,3-DIHYDRO-1,4-BENZODIOXIN-2-YL]METHYL}PROPAN-1-AMINE;
2-({[(2S)-5-CHLORO-7-(METHYLSULFONYL)-2,3-DIHYDRO-1,4-BENZODIOXIN-2-YL]METHYL}AMINO)ETHANOL;
N-{[(2S)-5-CHLORO-7-(METHYLSULFONYL)-2,3-DIHYDRO-1,4-BENZODIOXIN-2-YL]METHYL}-N-METHYLETHANAMINE;
N-{[(2S)-5-CHLORO-7-(METHYLSULFONYL)-2,3-DIHYDRO-1,4-BENZODIOXIN-2-YL]METHYL}-2-METHOXYETHANAMINE;
N-{[(2S)-5-CHLORO-7-(METHYL SULFONYL)-2,3-DIHYDRO-1,4-BENZODIOXIN-2-YL]METHYL}-2-METHYLPROPAN-1-AMINE;
N-{[(2S)-5-CHLORO-7-(METHYLSULFONYL)-2,3-DIHYDRO-1,4-BENZODIOXIN-2-YL]METHYL}-PROPAN-1-AMINE;
N-{[(2S)-5-CHLORO-7-(METHYLSULFONYL)-2,3-DIHYDRO-1,4-BENZODIOXIN-2-YL]METHYL}-3-FLUOROPROPAN-1-AMINE;
N-{[(2S)-5-CHLORO-7-(METHYLSULFONYL)-2,3-DIHYDRO-1,4-BENZODIOXIN-2-YL]METHYL}-2,2-DIMETHYLPROPAN-1-AMINE;
1-[(2S)-5-CHLORO-7-(METHYLSULFONYL)-2,3-DIHYDRO-1,4-BENZODIOXIN-2-YL]-N-METHYLMETHANAMINE;
N-{[(2S)-5-FLUORO-7-(METHYLSULFONYL)-2,3-DIHYDRO-1,4-BENZODIOXIN-2-YL]METHYL}-PROPAN-1-AMINE;
2,2-DIMETHYL-N-{[(2S)-7-(METHYLSULFONYL)-2,3-DIHYDRO-1,4-BENZODIOXIN-2-YL]METHYL}PROPAN-1-AMINE;
N-({(2S)-7-[(TRIFLUOROMETHYL)SULFONYL]-2,3-DIHYDRO-1,4-BENZODIOXIN-2-YL}METHYL)PROPAN-2-AMINE;

any of its stereoisomers or any mixture of its stereoisomers, or an N-oxide thereof, or a pharmaceutically acceptable salt thereof.

9. A pharmaceutical composition, comprising a therapeutically effective amount of a compound of claim 1, any of its stereoisomers or any mixture of its stereoisomers, or an N-oxide thereof, or a pharmaceutically acceptable salt thereof, together with at least one pharmaceutically acceptable carrier, excipient or diluent.

* * * * *

UNITED STATES PATENT AND TRADEMARK OFFICE
CERTIFICATE OF CORRECTION

PATENT NO. : 8,524,766 B2
APPLICATION NO. : 12/990048
DATED : September 3, 2013
INVENTOR(S) : Clas Sonesson et al.

Page 1 of 1

It is certified that error appears in the above-identified patent and that said Letters Patent is hereby corrected as shown below:

ON THE TITLE PAGE:

At item (73), Assignee, change:

"(73) Assignee:   NSAB, Filial af Neurosearch Sweden AB, Sverige, Ballerup (DK)"

to

--(73) Assignees:   Integrative Research Laboratories Sweden AB, Göteborg (SE)--.

Signed and Sealed this
Twenty-fourth Day of December, 2013

Margaret A. Focarino
*Commissioner for Patents of the United States Patent and Trademark Office*